United States Patent
Geerdink et al.

(10) Patent No.: US 11,992,012 B2
(45) Date of Patent: May 28, 2024

(54) DIAMINOTRIAZINE COMPOUNDS

(71) Applicant: BASF SE, Ludwigshafen (DE)

(72) Inventors: Danny Geerdink, Ludwigshafen (DE); Florian Vogt, Ludwigshafen (DE); Thomas Zierke, Ludwigshafen (DE); Martin Hartmueller, Limburgerhof (DE); Trevor William Newton, Limburgerhof (DE); Klaus Reinhard, Limburgerhof (DE); Thomas Seitz, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 628 days.

(21) Appl. No.: 17/270,884

(22) PCT Filed: Sep. 9, 2019

(86) PCT No.: PCT/EP2019/073915
§ 371 (c)(1),
(2) Date: Feb. 24, 2021

(87) PCT Pub. No.: WO2020/058009
PCT Pub. Date: Mar. 26, 2020

(65) Prior Publication Data
US 2021/0186021 A1    Jun. 24, 2021

(30) Foreign Application Priority Data

Sep. 18, 2018   (EP) .................................... 18195151

(51) Int. Cl.
| | | |
|---|---|---|
| *A01N 43/68* | (2006.01) | |
| *A01N 43/76* | (2006.01) | |
| *A01N 43/78* | (2006.01) | |
| *A01N 43/80* | (2006.01) | |
| *A01N 43/82* | (2006.01) | |
| *C07D 251/18* | (2006.01) | |
| *C07D 401/12* | (2006.01) | |
| *C07D 403/12* | (2006.01) | |
| *C07D 409/12* | (2006.01) | |
| *C07D 413/12* | (2006.01) | |
| *C07D 417/12* | (2006.01) | |

(52) U.S. Cl.
CPC .............. *A01N 43/68* (2013.01); *A01N 43/76* (2013.01); *A01N 43/78* (2013.01); *A01N 43/80* (2013.01); *A01N 43/82* (2013.01); *C07D 251/18* (2013.01); *C07D 401/12* (2013.01); *C07D 403/12* (2013.01); *C07D 409/12* (2013.01); *C07D 413/12* (2013.01); *C07D 417/12* (2013.01)

(58) Field of Classification Search
None
See application file for complete search history.

(56) References Cited

FOREIGN PATENT DOCUMENTS

| | | |
|---|---|---|
| CN | 106164057 A | 11/2016 |
| WO | WO-2015/155272 A1 | 10/2015 |
| WO | WO-2015/155273 A1 | 10/2015 |
| WO | WO-2015/162166 A1 | 10/2015 |

OTHER PUBLICATIONS

Chemcats, Accession No. 0339289328, vol. 1446, p. 71413987, May 12, 2017.
International Application No. PCT/EP2019/073915, International Search Report and Written Opinion, dated Oct. 14, 2019.
European Search Report for EP Patent Application No. 18195151.8, dated Nov. 21, 2018, 3 pages.
"Rn 1999820-07-3", Registry Copyright 2023 ACS on STN, Sep. 26, 2016, 1 Page.

*Primary Examiner* — Brian J Davis
(74) *Attorney, Agent, or Firm* — MARSHALL, GERSTEIN & BORUN LLP

(57) ABSTRACT

The present invention relates to diaminotriazine compounds and to their use as herbicides. It also relates to agrochemical compositions for crop protection and to a method for controlling unwanted vegetation.

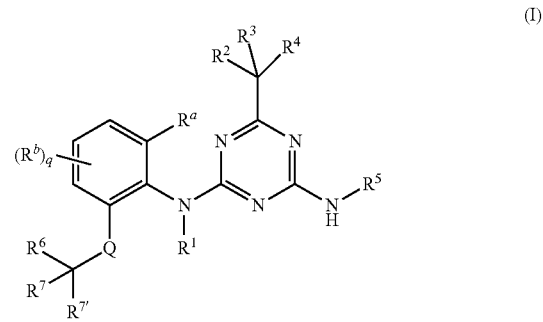

9 Claims, No Drawings

DIAMINOTRIAZINE COMPOUNDS

CROSS-REFERENCE TO RELATED APPLICATIONS

This is the U.S. national phase of International Application No. PCT/EP2019/073915, filed Sep. 9, 2019, which claims the benefit of European Patent Application No. 18195151.8, filed on Sep. 18, 2018.

The present invention relates to diaminotriazine compounds and to their use as herbicides. The present invention also relates to agrochemical compositions for crop protection and to a method for controlling unwanted vegetation.

Diaminotriazines and their use as herbicides are known from, for example, WO 2015/155272 and WO 2015/162166.

Nevertheless, there is still room for improvement, e.g. regarding activity, scope of activity and compatibility with useful plants of the known herbicidal compounds.

It is therefore an object of the present invention to provide compounds having improved herbicidal action, in particular good herbicide activity at low application rates. Moreover, the herbicides should be sufficiently compatible with crop plants for commercial utilization.

These and further objects are achieved by diaminotriazine compounds of formula (I), defined below, and by their agriculturally suitable salts.

Accordingly, the present invention relates to diaminotriazine compounds of formula (I)

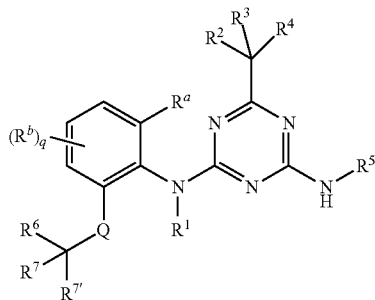

wherein
q is 0, 1, 2 or 3
Q is a O, $S(O)_m$, $CR^{q1}R^{q2}$, $NR^{q3}$, C(O), $S(O)_m NR^{q3}$ or, wherein
m is 0, 1 or 2;
$R^{q1}$, $R^{q2}$ are hydrogen, halogen, $C_1$-$C_4$-alkyl, $C_1$-$C_4$-halogenalkyl;
$R^{q3}$ is H, CN, $C_1$-$C_6$-alkyl, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, where the aliphatic parts of the radicals are unsubstituted, partly or completely halogenated;
$R^a$ is selected from the group consisting of hydrogen, halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, where the aliphatic and cycloaliphatic parts of the radicals are unsubstituted, partly or completely halogenated;
$R^b$ is selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_1$-$C_6$-cycloalkyl, $C_1$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the radicals are unsubstituted, partly or completely halogenated and where the cycloaliphatic parts of the last 4 mentioned radicals may carry 1, 2, 3, 4, 5 or 6 methyl groups,
for q=2 or 3 it being possible that $R^b$ are identical or different;
$R^1$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_3$-$C_6$-cycloalkyl)-carbonyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the radicals are unsubstituted, partly or completely halogenated,
phenyl, phenyl-$C_1$-$C_6$-alkyl, phenylsulfonyl, phenylaminosulfonyl, phenylaminocarbonyl, phenyl($C_1$-$C_6$-alkyl)aminocarbonyl, phenylcarbonyl and phenoxycarbonyl,
wherein phenyl in the last 8 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;
$R^2$ is selected from the group consisting of H, halogen, OH, CN, $C_1$-$C_6$-alkyl, ($C_1$-$C_6$-alkoxy)-$C_1$-$C_6$-alkyl, $C_1$-$C_6$-cycloalkyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_1$-$C_6$-cycloalkoxy, ($C_1$-$C_6$-cycloalkyl)-$C_1$-$C_4$-alkoxy, where the aliphatic and cycloaliphatic parts of the radicals are unsubstituted, partly or completely halogenated;
$R^3$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy;
$R^4$ is selected from the group consisting of halogen, CN, $C_1$-$C_6$-alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the radicals are unsubstituted, partly or completely halogenated;
$R^3$ and $R^4$ together with the carbon atom to which they are attached form a moiety selected from the group consisting of carbonyl, $C_1$-$C_6$-cycloalkyl, $C_1$-$C_6$-cycloalkenyl, three- to six-membered saturated or partially unsaturated heterocyclyl, and the moiety >C=$CR^xR^y$, where $R^x$ and $R^y$ are hydrogen, $C_1$-$C_4$-alkyl, $C_1$-$C_4$-haloalkyl, $C_3$-$C_6$-cycloalkyl or $CR^xR^y$ form a 3- to 6-membered cycloalkyl;
$R^5$ is selected from the group consisting of H, OH, $S(O)_2NH_2$, CN, $C_1$-$C_6$-alkyl,
$C_2$-$C_6$-alkenyl, $C_2$-$C_6$-alkynyl, ($C_3$-$C_6$-cycloalkyl)-$C_1$-$C_4$-alkyl, $C_3$-$C_6$-cycloalkyl)-carbonyl $C_1$-$C_6$-alkoxy, ($C_1$-$C_6$-alkoxy)-$C_1$-$C_6$-alkyl, ($C_1$-$C_6$-alkyl)carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the radicals are unsubstituted, partly or completely halogenated, phenyl, phenylsulfonyl, phenylaminosulfonyl, phenylaminocarbonyl, phenyl($C_1$-$C_6$-alkyl)aminocarbonyl, phenyl-$C_1$-$C_6$ alkyl, phenoxy, phenylcarbonyl and phenoxycarbonyl, wherein phenyl in the last 9 mentioned radicals is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^6$ is phenyl or a 5- to 6-membered heteroaryl, which is unsubstituted or carries 1, 2, 3, 4 or 5 radicals $R^{6A}$ which are selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-2-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_1$-$C_6$-cycloalkoxy, ($C_1$-$C_6$-cycloalkyl)-$C_1$-$C_4$-alkyl, ($C_1$-$C_6$-cycloalkyl)-$C_1$-$C_4$-alkoxy, where the aliphatic and cycloaliphatic parts of the radicals are unsubstituted, partly or completely halogenated and where the cycloaliphatic parts of the radicals may carry 1, 2, 3, 4, 5 or 6 methyl groups, it being possible that $R^{6A}$ are identical or different;

$R^7$ and $R^{7'}$ are independently selected from the group consisting of hydrogen, halogen, OH, CN, $NO_2$, SH, $NH_2$, NH($C_1$-$C_4$-alkyl), N($C_1$-$C_4$-alkyl)$_2$, NH—$SO_2$—$C_1$-$C_4$-alkyl, $C_1$-$C_6$-alkyl, $C_2$-$C_6$-alkenyl, $C_2$-$C_6$-alkynyl, $C_1$-$C_6$-alkoxy, $C_1$-$C_6$-halogenoalkoxy, $C_3$-$C_6$-cycloalkyl; and wherein the aliphatic moieties of $R^7$ and $R^{7'}$ are not further substituted or carry one, two, three or up to the maximum possible number of identical or different groups $R^7$ or $R^{7'}$ a which independently of one another are selected from:

$R^{7a}$, $R^{7'a}$ halogen, OH, CN, $C_1$-$C_6$-alkoxy, $C_3$-$C_6$-cycloalkyl, $C_3$-$C_6$-halogencycloalkyl, $C_1$-$C_4$-halogenoalkoxy and $C_1$-$C_6$-alkylthio wherein the cycloalkyl moieties of $R^7$ and $R^{7'}$ are not further substituted or carry one, two, three, four, five or up to the maximum number of identical or different groups $R^{7b}$ or $R^{7'b}$ which independently of one another are selected from:

$R^{7b}$, $R^{7'b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenoalkoxy and $C_1$-$C_6$-alkylthio;

including their agriculturally acceptable salts or derivatives.

The present invention also relates to agrochemical compositions comprising at least one diaminotriazine compound of formula (I) and at least one auxiliary customary for formulating crop protection agents.

The present invention also relates to the use of diaminotriazine compound of formula (I) as herbicides, i.e. for controlling unwanted and/or harmful vegetation or plants.

The present invention furthermore provides a method for controlling unwanted plants. The method includes allowing a herbicidally effective amount of at least one diaminotriazine compound of the formula (I) to act on the unwanted plants or vegetation, their seeds and/or their habitat. Application can be done before, during and/or after, preferably during and/or after, the emergence of the unwanted plants.

Moreover, the invention relates to processes for preparing diaminotriazine compound of formula (I) and to intermediates.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms.

As used herein, the terms "undesirable vegetation", "unwanted vegetation", unwanted plants" and "harmful plants" are synonyms.

In the context of substituents, the term "one or more substituents" means that the number of substituents is e.g. from 1 to 10, in particular 1, 2, 3, 4, 5, 6, 7 or 8.

If the diaminotriazine compounds of formula (I) as described herein is capable of forming geometrical isomers, for example E/Z isomers, the invention relates to both the pure isomers and mixtures thereof. Likewise, the invention relates to the use of the pure isomers and to the use of their mixtures and to compositions containing the pure isomers or mixtures thereof.

If the diaminotriazine compounds of formula (I) as described herein have one or more centres of chirality and, as a consequence, are present as enantiomers or diastereomers, the invention relates to both the pure enantiomers or diastereomers, and mixtures thereof. Likewise, the invention relates to the use of the pure enantiomers or diasteromers and to the use of the mixtures thereof and to compositions containing the pure enantiomers or diastereomers or mixtures thereof.

If the diaminotriazine compounds of formula (I) as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, ($C_1$-$C_4$-alkoxy)-$C_1$-$C_4$-alkyl, hydroxy-($C_1$-$C_4$-alkoxy)-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethyl-ammonium (oleamine salt), 2-(2-hydroxyeth-1-oxy)eth-1-ylammonium (diglycolamine salt), di(2-hydroxyeth-1-yl)-ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

The organic moieties mentioned in the definition of the variables, e.g. Q, q, $R^{q1}$, $R^{q2}$, $R^a$, $R^b$, $R^1$, $R^2$, $R^3$, $R^4$, $R^5$, $R^6$, $R^7$, $R^{7'}$ are—like the term halogen—collective terms for individual enumerations of the individual group members. The term halogen denotes in each case fluorine, chlorine, bromine or iodine. All hydrocarbon chains, i.e. all alkyl, haloalkyl, alkenyl, alkynyl, alkoxy, alkenyloxy, alkynyloxy, alkylthio, alkylsulfinyl, alkylsulfonyl, (alkyl)amino, di(alkyl)amino, alkoxyalkyl, alkoxyalkoxy, (alky)carbonyl, (alkoxy)carbonyl chains can be straight-chain or branched, the prefix $C_n$-$C_m$ denoting in each case the possible number of carbon atoms in the group. The same applies to composed radicals, such as cycloalkylalkyl and phenylalkyl.

Examples of Such Meanings are:

$C_1$-$C_4$-alkyl and also the $C_1$-$C_4$-alkyl moieties of $C_1$-$C_4$-alkoxy, $C_1$-$C_4$-alkylthio, $C_1$-$C_4$-alkylsulfonyl, ($C_1$-$C_4$-alkyl)carbonyl, ($C_1$-$C_4$-alkyl)carbonyl, ($C_1$-$C_4$-alkoxy) carbonyl, ($C_1$-$C_4$-alkyl)carbonyloxy, $C_1$-$C_4$-alkyloxy-$C_1$-$C_4$-alkyl, $C_3$-$C_6$-cycloalkyl-$C_1$-$C_4$-alkyl, ($C_1$-$C_4$-alkylamino)carbonyl, di($C_1$-$C_4$-alkyl)aminocarbonyl, ($C_1$-$C_4$-alkylamino)sulfonyl, di($C_1$-$C_4$-alkyl)aminosulfonyl or phenyl-$C_1$-$C_4$-alkyl: for example $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-alkoxy, $C_1$-$C_6$-alkylthio, $C_1$-$C_6$-alkylsulfonyl, ($C_1$-$C_6$-alkyl)carbonyl, ($C_1$-$C_6$-alkyl)carbonyl, ($C_1$-$C_6$-alkoxy) carbonyl, ($C_1$-$C_6$-alkyl)carbonyloxy, $C_1$-$C_6$-alkyloxy-$C_1$-$C_6$-alkyl, $C_3$-$C_6$-cycloalkyl-$C_1$-$C_6$-alkyl, phenyl ($C_1$-$C_6$-alkyl)aminocarbonyl, ($C_1$-$C_6$-alkylamino) carbonyl, di($C_1$-$C_6$-alkyl)aminocarbonyl, ($C_1$-$C_6$-alkylamino)sulfonyl, di($C_1$-$C_6$-alkyl)aminosulfonyl or phenyl-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_2$-$C_6$-alkenyl and also the $C_2$-$C_6$-alkenyl moieties of ($C_1$-$C_6$-alkoxy)-$C_2$-$C_6$-alkenyl: a linear or branched ethylenically unsaturated hydrocarbon group having 2 to 6 carbon atoms and a C═C-double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkynyl and also the $C_2$-$C_6$-alkynyl moieties of ($C_1$-$C_6$-alkoxy)-$C_2$-$C_6$-alkynyl: linear or branched unsaturated hydrocarbon group having 2 to 6 carbon atoms and containing at least one $C_1$-$C_6$-triple bond, such as ethynyl, 1-propynyl, 2-propynyl (propargyl), 1-butynyl, 2-butynyl, 3-butynyl, 1-methyl-2-propynyl and the like;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$-$C_6$-cycloalkyl: monocyclic saturated hydrocarbons having 3 to 6 ring members, such as cyclopropyl, cyclobutyl, cyclopentyl and cyclohexyl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of ($C_1$-$C_6$-alkoxy)carbonyl, ($C_1$-$C_6$-alkoxy)sulfonyl, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_4$-haloalkoxy: a $C_1$-$C_4$-alkoxy radical as mentioned above which is partially or fully substituted by fluorine, chlorine, bromine and/or iodine, for example, chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy2-fluoroethoxy, 2-chloroethoxy, 2-bromoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 4-fluorobutoxy, nonafluorobutoxy, 1,1,2,2,-tetrafluoroethoxy and 1-trifluoromethyl-1,2,2,2-tetrafluoroethoxy;

$C_1$-$C_6$-haloalkoxy-$C_1$-$C_4$-alkoxy as mentioned above: $C_1$-$C_4$-haloalkoxy as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_2$-$C_6$-alkenyloxy: $C_2$-$C_6$-alkenyl as defined above, which is bound via an oxygen atom, such as ethenyloxy (vinyloxy), 1-propenyloxy, 2-propenyloxy (allyloxy), 1-butenyloxy, 2-butenyloxy, 3-butenyloxy 1-methyl-2-propenyloxy and the like;

$C_2$-$C_6$-alkynyloxy: $C_2$-$C_6$-alkynyl as defined above, which is bound via an oxygen atom, such as ethynyloxy, 1-propynyl, 2-propynyloxy (propargyloxy), 1-butynyloxy, 2-butynyloxy, 3-butynyloxy 1-methyl-2-propynyloxy and the like;

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylsulfinyl ($C_1$-$C_6$-alkyl-S(=O)—): z.B. methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethypropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentyl-sulfinyl, 1,1-dimethylbutylsulfinyl, 1,2-dimethylbutylsulfinyl, 1,3-dimethylbutyl-sulfinyl, 2,2-dimethylbutylsulfinyl, 2,3-dimethylbutylsulfinyl, 3,3-dimethylbutyl-sulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-alkylsulfonyl ($C_1$-$C_6$-alkyl-S(O)$_2$—): for example methysulfonyl, ethylsulfonyl, propylsulfonyl, 1-methylethylsulfonyl, butylsulfonyl, 1-methylpropylsulfonyl, 2-methylpropylsulfonyl, 1,1-dimethyethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethyl-propylsulfonyl, 1,2,2-trimethylpropylsulfonyl, 1-ethyl-1-methylpropylsulfonyl and 1-ethyl-2-methylpropylsulfonyl;

($C_1$-$C_4$-alkyl)amino and also the ($C_1$-$C_4$-alkylamino) moieties of ($C_1$-$C_4$-alkylamino)carbonyl or ($C_1$-$C_4$-alkylamino)sulfonyl: for example methylamino, ethylamino, propylamino, 1-methylethylamino, butylamino, 1-methylpropylamino, 2-methylpropylamino or 1,1-dimethylethylamino;

($C_1$-$C_6$-alkyl)amino and also the ($C_1$-$C_6$-alkylamino) moieties of ($C_1$-$C_6$-alkylamino)carbonyl, phenyl($C_1$-$C_6$-alkyl)aminocarbonyl or ($C_1$-$C_6$-alkylamino)sulfonyl: ($C_1$-$C_4$-alky)amino as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutyamino, 2,3-dimethylbutylamino 3,3-dimethylbutylamino, 1-ethylbutylamino, 2-ethylbutylamino, 1,1,2-trimethylpropyamino, 1,2,2-trimethyl-propylamino, 1-ethyl-1-methylpropyamino or 1-ethyl-2-methylpropyamino;

di($C_1$-$C_4$-alkyl)amino and also the di($C_1$-$C_4$-alkylamino) moieties of di($C_1$-$C_4$-alkylamino)carbonyl or di($C_1$-$C_4$-alkylamino)sulfonyl: for example N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$-$C_6$-alkyl)amino and also the di($C_1$-$C_6$-alkylamino) moieties of di($C_1$-$C_6$-alkylamino)carbonyl or di($C_1$-$C_6$-alkylamino)sulfonyl: di($C_1$-$C_4$-alkyl)amino as mentioned above, and also, for example, N-methyl-N-pentylamino, N-methyl-N-(1-methylbutyl)amino, N-methyl-N-(2-methylbutyl)amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl)amino, N-ethyl-N-(3-methylpentyl)amino, N-ethyl-N-(4-methylpentyl)amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl)amino, N-ethyl-N-(1-ethylbutyl)amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

$C_3$-$C_6$-cycloalkyl and also the $C_3$-$C_6$-cyclolalkyl moieties of ($C_3$-$C_6$-cycloalkyl)-carbonyl, ($C_3$-$C_6$-cyclolalkyl)-$C_1$-$C_6$-alkyl, ($C_3$-$C_6$-cycloalkyl)carbonyl and ($C_1$-$C_6$-cyclolalkyl)-$C_1$-$C_6$-alkoxy: a cycloaliphatic radical having 3 to 6 carbon atoms, such as cyclopropyl, cyclobutyl, cyclopentyl and cyclohexyl;

$C_3$-$C_6$-cycloalkoxy: a cycloaliphatic radical having 3 to 6 carbon atoms and bound via an oxygen atom, such as cyclopropyloxy, cyclobutyloxy, cyclopentyloxy and cyclohexyloxy;

($C_3$-$C_6$-cyclolalkyl)-$C_1$-$C_6$-alkyl: $C_1$-$C_6$-alkyl, in particular $C_1$-$C_4$-alkyl as defined above, such as methyl or ethyl, wherein 1 hydrogen atom is replaced by $C_3$-$C_6$-cyclolalkyl as defined above, examples including cyclopropylmethyl ($CH_2$-cyclopropyl), cyclobutylmethyl, cyclopentylmethyl, cycloexylmethyl, 1-cyclopropylethyl ($CH(CH_3)$-cyclopropyl), 1-cyclobutylethyl, 1-cyclopentylethyl, 1-cycloexylethyl, 2-cyclopropylethyl ($CH_2CH_2$-cyclopropyl), 2-cyclobutylethyl, 2-cyclopentylethyl or 2-cycloexylethyl;

($C_3$-$C_6$-cyclolalkyl)-$C_1$-$C_6$-alkoxy: $C_1$-$C_6$-alkoxy, in particular $C_1$-$C_4$-alkoxy as defined above, such as methoxy or ethoxy, wherein 1 hydrogen atom is replaced by $C_3$-$C_6$-cyclolalkyl as defined above, examples including cyclopropylmethoxy ($OCH_2$-cyclopropyl), cyclobutylmethoxy, cyclopentylmethoxy, cycloexylmethoxy, 1-cyclopropylethoxy (O—CH($CH_3$)-cyclopropyl), 1-cyclobutylethoxy, 1-cyclopentylethoxy, 1-cycloexylethoxy, 2-cyclopropylethoxy ($OCH_2CH_2$-cyclopropyl), 2-cyclobutylethoxy, 2-cyclopentylethoxy and 2-cycloexylethoxy;

($C_1$-$C_6$-alkoxy)-$C_1$-$C_6$-alkyl: $C_1$-$C_6$-alkyl, in particular $C_1$-$C_4$-alkyl as defined above, such as methyl, ethyl or isopropyl, wherein 1 hydrogen atom is replaced by $C_1$-$C_6$-alkoxy as defined above, examples including methoxymethyl, ethoxymethyl, n-propoxymethyl, butoxymethyl, 1-methoxyethyl, 1-ethoxyethyl, 1-(n-propoxy)ethyl, 1-butoxyethyl, 2-methoxyethyl, 2-ethoxyethyl, 2-(n-propoxy)ethyl, 2-butoxyethyl, 2-methoxypropyl, 2-ethoxypropyl, 2-(n-propoxy)propyl, 2-butoxypropyl;

($C_1$-$C_6$-alkoxy)-$C_1$-$C_6$-alkoxy: $C_1$-$C_6$-alkoxy, in particular $C_1$-$C_4$-alkoxy as defined above, such as methoxy or ethoxy, wherein 1 hydrogen atom is replaced by $C_1$-$C_6$-alkoxy as defined above, examples including methoxymethoxy, ethoxymethoxy, n-propoxymethoxy, butoxymethoxy, 2-methoxyethoxy, 2-ethoxyethoxy, 2-(n-propoxy)ethoxy and 2-butoxyethoxy;

($C_1$-$C_6$-alkoxy)-$C_2$-$C_6$-alkenyl: $C_2$-$C_4$-alkenyl, in particular $C_2$-$C_4$-alkenyl as defined above, such as ethenyl, propenyl, 1-butenyl or 2-butenyl, wherein 1 hydrogen atom is replaced by $C_1$-$C_6$-alkoxy as defined above;

($C_1$-$C_6$-alkoxy)-$C_2$-$C_6$-alkynyl: $C_2$-$C_4$-alkynyl, in particular $C_2$-$C_4$-alkynyl as defined above, such as ethynyl, propynyl or 2-butynyl, wherein 1 hydrogen atom is replaced by $C_1$-$C_6$-alkoxy as defined above;

($C_1$-$C_6$-alkyl)carbonyl: $C_1$-$C_6$-alkyl as mentioned above, which is bound to the remainder of the molecule by a carbonyl group;

($C_1$-$C_6$-alkoxy)carbonyl: $C_1$-$C_6$-alkyloxy as mentioned above, which is bound to the remainder of the molecule by a carbonyl group;

($C_1$-$C_6$-alkylamino)carbonyl: ($C_1$-$C_6$-alkyl)amino as mentioned above, which is bound to the remainder of the molecule by a carbonyl group;

($C_1$-$C_6$-alkylamino)sulfonyl: ($C_1$-$C_6$-alkyl)amino as mentioned above, which is bound to the remainder of the molecule by a sulfonyl group;

di($C_1$-$C_6$-alkylamino)carbonyl: di($C_1$-$C_6$-alkyl)amino as mentioned above, which is bound to the remainder of the molecule by a carbonyl group;

di($C_1$-$C_6$-alkylamino)sulfonyl: di($C_1$-$C_6$-alkyl)amino as mentioned above, which is bound to the remainder of the molecule by a sulfonyl group;

phenyl-$C_1$-$C_6$-alkyl: $C_1$-$C_6$-alkyl, in particular $C_1$-$C_4$-alkyl as defined above, such as methyl or ethyl, wherein 1 hydrogen atom is replaced by phenyl, examples including benzyl, 1-phenylethyl, 2-phenylethyl, 1-phenylpropyl, 2-phenylpropyl, 1-phenyl-1-methylethyl etc.;

three- to six-membered heterocyclyl: monocyclic saturated or partially unsaturated hydrocarbon having three to six ring members as mentioned above which, in addition to carbon atoms, contains one or two heteroatoms selected from O, S and N; for example saturated heterocycles such as 2-oxiranyl, 2-oxetanyl, 3-oxetanyl, 2-azirdinyl, 3-thietanyl, 1-azetidinyl, 2-azetidinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-piperidinyl, 3-piperidinyl, 4-piperidinyl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,4-dithian-2-yl, 1,3-dithian-5-yl, 2-tetrahydropyranyl, 3-tetrahydropyranyl, 4-tetrahydropyranyl, 2-tetrahydrothiopyranyl, 3-tetrahydrothiopyranyl, 4-tetrahydro-thiopyranyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, tetrahydro-1,3-oxazin-2-yl, tetrahydro-1,3-oxazin-6-yl, 2-morpholinyl, 3-morpholinyl or 4-morpholinyl, for example 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl;

partially unsaturated heterocycles such as 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 4,5-dihydropyrrol-2-yl, 4,5-dihydropyrrol-3-yl, 2,5-dihydropyrrol-2-yl, 2,5-dihydropyrrol-3-yl, 4,5-dihydroisoxazol-3-yl, 2,5-dihydroisoxazol-3-yl, 2,3-dihydroisoxazol-3-yl, 4,5-dihydroisoxazol-4-yl, 2,5-dihydroisoxazol-4-yl, 2,3-dihydroisoxazol-4-yl, 4,5-dihydroisoxazol-5-yl, 2,5-dihydroisoxazol-5-yl, 2,3-dihydroisoxazol-5-yl, 4,5-dihydroisothiazol-3-yl, 2,5-dihydroisothiazol-3-yl, 2,3-dihydroisothiazol-3-yl, 4,5-dihydroisothiazol-4-yl, 2,5-dihydroisothiazol-4-yl, 2,3-dihydroisothiazol-4-yl, 4,5-dihydroisothiazol-5-yl, 2,5-dihydroisothiazol-5-yl, 2,3-dihydroisothiazol-5-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-3-yl, 3,4-dihydropyrazol-4-yl, 3,4-dihydropyrazol-5-yl, 4,5-dihydropyrazol-3-yl, 4,5-dihydropyrazol-4-yl, 4,5-dihydropyrazol-5-yl, 2,3-dihydroimidazol-2-yl, 2,3-dihydroimidazol-3-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-5-yl, 2,3-dihydrooxazol-3-yl, 2,3-dihydrooxazol-4-yl, 2,3-dihydrooxazol-5-yl, 3,4-dihydrooxazol-3-yl, 3,4-dihydrooxazol-4-yl, 3,4-dihydrooxazol-5-yl, 2,3-dihydrothiazol-3-yl, 2,3-dihydrothiazol-4-yl, 2,3-dihydrothiazol-5-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, 3,4-dihydrothiazol-4-yl, 3,6-dihydro-2H-pyran-2-yl, 3,6-dihydro-2H-pyran-3-yl, 3,6-dihydro-2H-pyran-4-yl, 3,6-dihydro-2H-pyran-5-yl, 3,6-dihydro-2H-pyran-6-yl, 3,4-dihydro-2H-pyran-3-yl, 3,4-dihydro-2H-pyran-4-yl, 3,4-dihydro-2H-pyran-6-yl, 5,6-dihydro-4H-1,3-oxazin-2-yl;

5- and 6-membered heteroaryl which contains 1, 2 or 3 heteroatoms selected from O, S and N:

5-membered or 6-membered heteroaromatic radical, which besides carbon atoms contains 1, 2 or 3 heteroatoms as ring members, which are selected from O, S and N e.g. 1, 2 or 3 nitrogen atoms or 1 oxygen or sulfur atom and optionally 1 or 2 nitrogen atoms: in particular five-membered monocyclic heteroaryl which contains one to three heteroatoms selected from O, S and N:

for example 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl etc.;

six-membered monocyclic heteroaryl contains one to three nitrogen atoms as ring members:

for example 2-pyridinyl (2-pyridyl), 3-pyridinyl (3-pyridyl), 4-pyridinyl (4-pyridyl), 1-oxopyridin-2-yl, 1-oxopyridin-3-yl, 1-oxopyridin-4-yl,3-pyridazinyl, 4-pyridazinyl, 2-pyrimidinyl, 4-pyrimidinyl, 5-pyrimidinyl, 2-pyrazinyl and 1,2,3-triazinyl, 1,2,4-triazinyl and 1,3,5-triazinyl.

The preferred embodiments of the invention mentioned herein below have to be understood as being preferred either independently from each other or in combination with one another. Particular groups of embodiments of the invention relate to those diaminotriazines of formula (I), wherein the variables Q, q, m, $R^{q1}$, $R^{q2}$, $R^{q3}$, $R^a$, $R^b$, $R^1$, $R^2$, $R^3$, $R^4$, $R^5$, $R^6$, $R^7$, $R^7$ either independently of one another or in combination with one another, have the following meanings:

Particular groups of embodiments relate to the diaminotriazine compounds of formula (I), wherein Q has the meaning as defined above.

In particular

Q is O, $CR^{q1}R^{q2}$, C(O) or $S(O)_2$, wherein $R^{q1}$ and $R^{q2}$ are identical or different selected from the group of hydrogen, halogen, $C_1$-$C_4$-alkyl and $C_1$-$C_4$-halogenalkyl.

Especially preferred

Q is a O, $CH_2$, C(O),

Most preferred Q is O.

Further particular groups of embodiment relate to the diaminotriazine compound of formula (I), wherein $R^a$ is defined above.

In particular $R^a$ is selected from the group consisting of halogen, CN, $C_1$-$C_4$-alkyl, $C_2$-$C_4$-alkenyl, $C_2$-$C_4$-alkynyl, $C_1$-$C_4$-alkoxy, $C_2$-$C_4$-alkenyloxy, $C_2$-$C_4$-alkynyloxy, where the aliphatic parts of the 6 aforementioned radicals are unsubstituted, partly or completely halogenated and for q=2 or 3 it being possible that $R^a$ are identical or different.

More particular $R^a$ is selected halogen, CN, $C_1$-$C_4$-alkyl, $C_1$-$C_4$-haloalkyl, $C_2$-$C_4$-alkenyl, $C_2$-$C_4$-alkynyl, $C_1$-$C_4$-alkoxy, $C_1$-$C_4$-haloalkoxy, $C_2$-$C_4$-alkenyloxy, $C_2$-$C_4$-alkynyloxy.

Even more particular $R^a$ is selected F, $C_1$, Br, CN.

Further particular groups of embodiment relate to the diaminotriazine compound of formula (I), wherein $R^b$ is defined above.

In particular $R^b$ is selected from the group consisting of halogen, CN, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_3$-$C_6$-cycloalkyl, where the aliphatic parts of the 6 aforementioned radicals are unsubstituted, partly or completely halogenated and for q=2 or 3 it being possible that $R^b$ are identical or different.

More particular $R^b$ is selected halogen, CN, $C_1$-$C_4$-alkyl, $C_1$-$C_4$-haloalkyl, $C_2$-$C_4$-alkenyl, $C_2$-$C_4$-alkynyl, $C_1$-$C_4$-alkoxy, $C_1$-$C_4$-haloalkoxy, $C_2$-$C_4$-alkenyloxy, $C_2$-$C_4$-alkynyloxy, $C_3$-$C_6$-cycloalkyl.

Even more particular $R^b$ is selected F, C, Br, CN, methyl, cyclopropyl, cyclobutyl.

Further particular groups of embodiment relate to the diaminotriazine compound of formula (I), wherein:

$R^1$ is H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_3$-$C_6$-cycloalkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 15 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy; preferably, H, CN, $C_1$-$C_6$-alkyl, ($C_1$-$C_6$-alkoxy)-$C_1$-$C_6$-alkyl, ($C_1$-$C_6$-alkyl)carbonyl ($C_3$-$C_6$-cycloalkyl)-carbonyl or ($C_1$-$C_6$-alkyl)sulfonyl, where the aliphatic parts of the 5 aforementioned radicals unsubstituted partly or completely halogenated, phenyl and phenyl-$C_1$-$C_6$ alkyl, wherein phenyl in the last 2 mentioned radical is unsubstituted or substituted by 1, 2, 3, 4, or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy; in particular H, CN, $C_1$-$C_6$-alkyl, $C_1$-$C_6$-haloalkyl, ($C_1$-$C_6$-alkoxy)-$C_1$-$C_6$-alkyl, $C_1$-$C_6$-alkoxy, ($C_1$-$C_6$-alkyl)carbonyl, ($C_3$-$C_6$-cycloalkyl)-carbonyl, ($C_1$-$C_6$-haloalkyl)carbonyl, ($C_1$-$C_6$-alkyl)sulfonyl or ($C_1$-$C_6$-haloalkyl)sulfonyl;

more particularly H, CN, $C_1$-$C_4$-alkyl, ($C_1$-$C_4$-alkoxy)-$C_1$-$C_4$-alkyl, $C_1$-$C_4$-alkoxy, ($C_1$-$C_4$-alkyl)carbonyl, ($C_3$-$C_6$-cycloalkyl)-carbonyl, or ($C_1$-$C_4$-alkyl)sulfonyl; even more particularly H, CN, $CH_3$, $CH_2OCH_3$, $OCH_3$, $C(O)CH_3$, C(O)cyclopropyl or $SO_2CH_3$; especially hydrogen.

Further particular groups of embodiments relate to the diaminotriazine compounds of formula (I), wherein;

Also preferred are diaminotriazine compounds of formula (I), wherein $R^2$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy, in particular from the group consisting of hydrogen, fluorine, $C_1$-$C_4$-alkyl, such as methyl, ethyl, n-propyl, 2-propyl, n-butyl, 2-butyl, isobutyl or tert.-butyl, $C_1$-$C_4$-haloalkyl, such as difluoromethyl, trifluoromethyl, 2,2,2-trifluoroethyl, 1,1-difluoroethyl, 1,1,2,2-tetrafluoroethyl or pentafluoroethyl, $C_1$-$C_4$-alkoxy, such as methoxy or ethoxy and $C_1$-$C_4$-haloalkoxy, such as difluoromethoxy or trifluoromethoxy.

Further particular groups (1) of embodiments relate to the diaminotriazine compounds of formula (I), wherein $R^3$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy, in particular from the group consisting of hydrogen, fluorine and $C_1$-$C_4$-alkyl, more particularly from hydrogen, fluorine and methyl, especially from fluorine and methyl.

In groups (1) of embodiments, $R^4$ is as defined above.

Preferably $R^4$ is selected from the group consisting of $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, $C_1$-$C_6$-alkoxy and $C_1$-$C_6$-alkoxy-$C_1$-$C_6$-alkyl or from $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, $C_1$-$C_6$-alkoxy and $C_1$-$C_6$-alkoxy-$C_1$-$C_6$-alkyl.

Further particular groups (2) of embodiments relate to the diaminotriazine compounds of formula (I), wherein $R^3$ and $R^4$ together with the carbon atom to which they are attached form a moiety selected from the group consisting of carbonyl, $C_3$-$C_6$-cycloalkan-1,1-diyl, ipso-$C_3$-$C_6$-cycloalkenediyl, three- to six-membered saturated or partially unsaturated ipso-heterocyclodiyl, where the carbocycle and the heterocycle are unsubstituted, partly or completely halogenated or carry from 1 to 6 $C_1$-$C_6$-alkyl groups, and the moiety >C=$CR^xR^y$, where $R^x$ and $R^y$ are hydrogen, $C_1$-$C_4$-alkyl, $C_1$-$C_4$-haloalkyl, $C_3$-$C_6$-cycloalkyl or $CR^xR^y$ form a 3 to 6 membered cycloalkyl.

In groups (2) of embodiments, $R^3$ and $R^4$ together with the carbon atom to which they are attached form in particular a moiety selected from the group consisting of $C_3$-$C_6$-cycloalkan-1,1-diyl, ipso-$C_3$-$C_6$-cycloalkenediyl, three- to six-membered saturated or partially unsaturated ipso-heterocyclodiyl, where the carbocycle and the heterocycle are unsubstituted, partly or completely halogenated or carry from 1 to 6 $C_1$-$C_6$-alkyl groups and where the heterocycle preferably has 1 or 2 oxygen atoms as ring members.

In groups (2) of embodiments, $R^3$ and $R^4$ together with the carbon atom to which they are attached more particularly form a moiety selected from the group consisting of $C_3$-$C_6$-cycloalkan-1,1-diyl or three- to six-membered saturated ipso-heterocyclodiyl, where the carbocycle and the heterocycle are unsubstituted, partly or completely halogenated or carry from 1 to 6 $C_1$-$C_6$-alkyl groups, and where heterocyclyl preferably has 1 or 2 oxygen atoms as ring members.

Further particular groups (2a) of embodiments relate to the diaminotriazine compounds of formula (I), wherein $R^3$ and $R^4$ together with the carbon atom to which they are attached form $C_3$-$C_6$-cycloalkan-1,1-diyl, in particular cyclopropan-1,1-diyl, cyclobutan-1,1-diyl, cyclopentan-1,1-diyl or cyclohexan-1,1-diyl, said $C_3$-$C_6$-cycloalkan-1,1-diyl being unsubstituted, partly or completely halogenated or carrying from 1 to 6 $C_1$-$C_6$-alkyl groups, in particular methyl groups. In groups (2a) of embodiments $R^3$ and $R^4$ together with the carbon atom to which they are attached form in particular $C_3$-$C_6$-cycloalkan-1,1-diyl which is unsubstituted.

Further particular groups (2b) of embodiments relate to the diaminotriazine compounds of formula (I), wherein $R^3$ and $R^4$ together with the carbon atom to which they are attached form three- to six-membered saturated ipso-heterocyclodiyl, in particular oxiran-1,1-diyl, oxetan-1,1-diyl, oxan-1,1-diyl, oxan-1,1-diyl or oxan-4,4-diyl, said heterocycle being unsubstituted, partly or completely halogenated or carrying from 1 to 6 $C_1$-$C_6$-alkyl groups, in particular groups, and where said heterocycle preferably has 1 or 2 oxygen atoms as ring members. In groups (2b) of embodiments $R^3$ and $R^4$ together with the carbon atom to which they are attached form three- to six-membered saturated ipso-heterocyclodiyl, in particular oxiran-1,1-diyl, oxetan-1,1-diyl, oxan-1,1-diyl, oxan-1,1-diyl or oxan-4,4-diyl, said heterocycle being unsubstituted.

Especially preferred examples of $CR^2R^3R^4$ are those radicals, where $R^2$, $R^3$ and $R^4$ are given in rows 1 to 64 of table 1a.

TABLE 1a

| no. | $R^2$ | $R^3$ | $R^4$ |
|---|---|---|---|
| 1. | H | $CH_3$ | $CH_3$ |
| 2. | F | F | $CH_3$ |
| 3. | F | H | $CH_3$ |
| 4. | F | $CH_3$ | $CH_3$ |
| 5. | $CH_3$ | $CH_3$ | $CH_3$ |
| 6. | F | H | $C_2H_5$ |
| 7. | H | $CH_3$ | $C_2H_5$ |
| 8. | F | $CH_3$ | $C_2H_5$ |
| 9. | H | $OCH_3$ | $CH_3$ |
| 10. | H | $OCH_3$ | $C_2H_5$ |
| 11. | F | $C_2H_5$ | $C_2H_5$ |
| 12. | H | $OCH_3$ | $C_2H_5$ |
| 13. | H | H | $CH(CH_3)_2$ |
| 14. | H | F | $CH(CH_3)_2$ |
| 15. | F | F | $CH(CH_3)_2$ |
| 16. | H | $CH_3$ | $CH(CH_3)_2$ |
| 17. | H | $OCH_3$ | $CH(CH_3)_2$ |
| 18. | F | $CH_3$ | $CH(CH_3)_2$ |
| 19. | H | H | $CH_2CH_2CH_3$ |
| 20. | H | F | $CH_2CH_2CH_3$ |
| 21. | F | F | $CH_2CH_2CH_3$ |
| 22. | H | $CH_3$ | $CH_2CH_2CH_3$ |
| 23. | H | $OCH_3$ | $CH_2CH_2CH_3$ |
| 24. | F | $CH_3$ | $CH_2CH_2CH_3$ |
| 25. | H | H | $C(CH_3)_3$ |
| 26. | H | F | $C(CH_3)_3$ |
| 27. | F | F | $C(CH_3)_3$ |
| 28. | H | $CH_3$ | $C(CH_3)_3$ |
| 29. | H | $OCH_3$ | $C(CH_3)_3$ |
| 30. | F | $CH_3$ | $C(CH_3)_3$ |
| 31. | H | H | Cyclopropyl |
| 32. | H | F | Cyclopropyl |
| 33. | F | F | Cyclopropyl |
| 34. | H | $CH_3$ | Cyclopropyl |
| 35. | H | $OCH_3$ | Cyclopropyl |
| 36. | F | $CH_3$ | Cyclopropyl |
| 37. | H | $CH_3$ | $CF_3$ |
| 38. | F | $CH_3$ | $CF_3$ |
| 39. | H | | $CH_2$—$CH_2$ |
| 40. | $CH_3$ | | $CH_2$—$CH_2$ |
| 41. | $OCH_3$ | | $CH_2$—$CH_2$ |
| 42. | F | | $CH_2$—$CH_2$ |
| 43. | Cl | | $CH_2$—$CH_2$ |
| 44. | H | | $CH_2$—$CH_2$—$CH_2$ |
| 45. | $CH_3$ | | $CH_2$—$CH_2$—$CH_2$ |
| 46. | $OCH_3$ | | $CH_2$—$CH_2$—$CH_2$ |
| 47. | F | | $CH_2$—$CH_2$—$CH_2$ |
| 48. | Cl | | $CH_2$—$CH_2$—$CH_2$ |
| 49. | H | | $CH_2$—$CH_2$—$CH_2$—$CH_2$ |
| 50. | $CH_3$ | | $CH_2$—$CH_2$—$CH_2$—$CH_2$ |
| 51. | $OCH_3$ | | $CH_2$—$CH_2$—$CH_2$—$CH_2$ |
| 52. | F | | $CH_2$—$CH_2$—$CH_2$—$CH_2$ |
| 53. | Cl | | $CH_2$—$CH_2$—$CH_2$—$CH_2$ |
| 54. | H | | $CH_2$—$CH_2$—$CH_2$—$CH_2$—$CH_2$ |
| 55. | $CH_3$ | | $CH_2$—$CH_2$—$CH_2$—$CH_2$—$CH_2$ |
| 56. | $OCH_3$ | | $CH_2$—$CH_2$—$CH_2$—$CH_2$—$CH_2$ |
| 57. | F | | $CH_2$—$CH_2$—$CH_2$—$CH_2$—$CH_2$ |
| 58. | Cl | | $CH_2$—$CH_2$—$CH_2$—$CH_2$—$CH_2$ |
| 59. | H | | O—$CH_2$—$CH_2$—$CH_2$ |
| 60. | $CH_3$ | | O—$CH_2$—$CH_2$—$CH_2$ |
| 61. | $OCH_3$ | | O—$CH_2$—$CH_2$—$CH_2$ |
| 62. | H | | O—$CH_2$—$CH_2$—$CH_2$—$CH_2$ |
| 63. | $CH_3$ | | O—$CH_2$—$CH_2$—$CH_2$—$CH_2$ |
| 64. | $OCH_3$ | | O—$CH_2$—$CH_2$—$CH_2$—$CH_2$ |

$R^5$ is H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)carbonyl, ($C_1$-$C_6$-alkoxy)carbonyl, ($C_3$-$C_6$-cycloalkyl)-carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 15 aforementioned radicals are unsubstituted, partly or completely halogenated, phenyl, phenylsulfonyl, phenylaminosulfonyl, phenyl-$C_1$-$C_6$ alkyl, phenoxy, phenylcarbonyl and phenoxycarbonyl, wherein phenyl in the last 6 mentioned radicals is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy; preferably, H, CN, $C_1$-$C_6$-alkyl, ($C_1$-$C_6$-alkoxy)-$C_1$-$C_6$-alkyl, ($C_1$-$C_6$-alkyl)carbonyl, ($C_3$-$C_6$-cycloalkyl)-carbonyl or ($C_1$-$C_6$-alkyl)sulfonyl, where the aliphatic parts of the 4 aforementioned radicals unsubstituted partly or completely halogenated; phenyl and phenyl-$C_1$-$C_6$ alkyl, wherein phenyl in the last 2 mentioned radical is unsubstituted or substituted by 1, 2, 3, 4, or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy; in particular H, CN, $C_1$-$C_6$-alkyl, ($C_1$-$C_6$-alkoxy)-$C_1$-$C_6$-alkyl, ($C_1$-$C_6$-alkyl)carbonyl, ($C_3$-$C_6$-cycloalkyl)-carbonyl, or ($C_1$-$C_6$-alkyl)sulfonyl;

more particularly H, CN, $C_1$-$C_4$-alkyl, ($C_1$-$C_4$-alkoxy)-$C_1$-$C_4$-alkyl, ($C_1$-$C_4$-alkyl)carbonyl, ($C_3$-$C_6$-cycloalkyl)-carbonyl, or ($C_1$-$C_4$-alkyl)sulfonyl;

even more particularly H, CN, $CH_3$, $CH_2CH_3$, $C(O)CH_3$, $C(O)$cyclopropyl or $SO_2CH_3$; especially hydrogen.

Further particular groups of embodiments relate to the diaminotriazine compounds of formula (I), wherein $R^6$ is phenyl or a 5- to 6-membered heteroaryl, which is unsubstituted or carries 1, 2, 3, 4 or 5 radicals $R^{6A}$ which are selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the radicals are unsubstituted, partly or completely halogenated and where the cycloaliphatic parts of the radicals may carry 1, 2, 3, 4, 5 or 6 methyl groups, it being possible that $R^{6A}$ are identical or different.

According to one preferred embodiment $R^6$ is phenyl, which is unsubstituted or carries 1 to 5 radicals $R^{6A}$ selected from the group consisting of halogen, CN, $C_1$-$C_4$-alkyl, $C_1$-$C_4$-haloalkyl, $C_1$-$C_4$-alkoxy, $C_1$-$C_4$-haloalkoxy and $C_3$-$C_6$-cycloalkyl.

According to one preferred embodiment $R^6$ is 5- to 6-membered heteroaryl, which is unsubstituted or carries 1 or 5 radicals $R^{6A}$ selected from the group consisting of halogen, CN, $C_1$-$C_4$-alkyl, $C_{1-4}$-haloalkyl, $C_{1-4}$-alkoxy, $C_1$-$C_4$-haloalkoxy and $C_3$-$C_6$-cycloalkyl.

Especially preferred examples for $R^6$ are given in rows 1 to 148 of table 2a.

TABLE 2a

| no. | $R^6$ |
|---|---|
| 1. | $C_6H_5$ |
| 2. | 2-F—$C_6H_4$ |
| 3. | 3-F—$C_6H_4$ |
| 4. | 4-F—$C_6H_4$ |
| 5. | 2-Cl—$C_6H_4$ |
| 6. | 3-Cl—$C_6H_4$ |
| 7. | 4-Cl—$C_6H_4$ |
| 8. | 2-Br—$C_6H_4$ |
| 9. | 3-Br—$C_6H_4$ |
| 10. | 4-Br—$C_6H_4$ |
| 11. | 2-I—$C_6H_4$ |
| 12. | 3-I—$C_6H_4$ |
| 13. | 4-I—$C_6H_4$ |
| 14. | 2-CN—$C_6H_4$ |
| 15. | 3-CN—$C_6H_4$ |
| 16. | 4-CN—$C_6H_4$ |
| 17. | 2-$OCH_3$—$C_6H_4$ |
| 18. | 3-$OCH_3$—$C_6H_4$ |
| 19. | 4-$OCH_3$—$C_6H_4$ |
| 20. | 2-$CH_3$—$C_6H_4$ |
| 21. | 3-$CH_3$—$C_6H_4$ |
| 22. | 4-$CH_3$—$C_6H_4$ |
| 23. | 2-$CH_2$—$CH_3$—$C_6H_4$ |
| 24. | 3-$CH_2$—$CH_3$—$C_6H_4$ |
| 25. | 4-$CH_2$—$CH_3$—$C_6H_4$ |
| 26. | 2,3-$F_2$—$C_6H_3$ |
| 27. | 2,4-$F_2$—$C_6H_3$ |
| 28. | 2,5-$F_2$—$C_6H_3$ |
| 29. | 2,6-$F_2$—$C_6H_3$ |
| 30. | 3,4-$F_2$—$C_6H_3$ |
| 31. | 3,5-$F_2$—$C_6H_3$ |
| 32. | 2,3-$Cl_2$—$C_6H_3$ |
| 33. | 2,4-$Cl_2$—$C_6H_3$ |
| 34. | 2,5-$Cl_2$—$C_6H_3$ |
| 35. | 2,6-$Cl_2$—$C_6H_3$ |
| 36. | 3,4-$Cl_2$—$C_6H_3$ |
| 37. | 3,5-$Cl_2$—$C_6H_3$ |
| 38. | 2-F-3-Cl—$C_6H_3$ |
| 39. | 2-F-4-Cl—$C_6H_3$ |
| 40. | 2-F-5-Cl—$C_6H_3$ |
| 41. | 2-F-6-Cl—$C_6H_3$ |
| 42. | 3-F-2-Cl—$C_6H_3$ |
| 43. | 3-F-4-Cl—$C_6H_3$ |
| 44. | 3-F-5-Cl—$C_6H_3$ |
| 45. | 3-F-6-Cl—$C_6H_3$ |
| 46. | 4-F-2-Cl—$C_6H_3$ |
| 47. | 4-F-3-Cl—$C_6H_3$ |
| 48. | 4-F-5-Cl—$C_6H_3$ |
| 49. | 4-F-6-Cl—$C_6H_3$ |
| 50. | 2-F-3-$OCH_3$—$C_6H_3$ |
| 51. | 2-F-4-$OCH_3$—$C_6H_3$ |
| 52. | 2-F-5-$OCH_3$—$C_6H_3$ |
| 53. | 2-F-6-$OCH_3$—$C_6H_3$ |
| 54. | 3-F-2-$OCH_3$—$C_6H_3$ |
| 55. | 2-Cl-3-F—$C_6H_3$ |
| 56. | 2-Cl-4-F—$C_6H_3$ |
| 57. | 2-Cl-5-F—$C_6H_3$ |
| 58. | 2-Cl-6-F—$C_6H_3$ |
| 59. | 3-Cl-2-F—$C_6H_3$ |
| 60. | 3-Cl-4-F—$C_6H_3$ |
| 61. | 3-Cl-5-F—$C_6H_3$ |
| 62. | 3-Cl-6-F—$C_6H_3$ |
| 63. | 4-Cl-2-F—$C_6H_3$ |
| 64. | 4-Cl-3-F—$C_6H_3$ |
| 65. | 4-Cl-5-F—$C_6H_3$ |
| 66. | 4-Cl-6-F—$C_6H_3$ |
| 67. | 2-Cl-3-$OCH_3$—$C_6H_3$ |
| 68. | 2-Cl-4-$OCH_3$—$C_6H_3$ |
| 69. | 2-Cl-5-$OCH_3$—$C_6H_3$ |
| 70. | 2-Cl-6-$OCH_3$—$C_6H_3$ |
| 71. | 3-Cl-2-$OCH_3$—$C_6H_3$ |
| 72. | 3-Cl-4-$OCH_3$—$C_6H_3$ |
| 73. | 3-Cl-5-$OCH_3$—$C_6H_3$ |
| 74. | 3-Cl-6-$OCH_3$—$C_6H_3$ |
| 75. | 4-Cl-2-$OCH_3$—$C_6H_3$ |
| 76. | 4-Cl-3-$OCH_3$—$C_6H_3$ |
| 77. | 4-Cl-5-$OCH_3$—$C_6H_3$ |
| 78. | 4-Cl-6-$OCH_3$—$C_6H_3$ |
| 79. | 2,3,4-$F_3$—$C_6H_2$ |
| 80. | 2,3,5-$F_3$—$C_6H_2$ |
| 81. | 2,3,6-$F_3$—$C_6H_2$ |
| 82. | 2,4,5-$F_3$—$C_6H_2$ |
| 83. | 2,4,6-$F_3$—$C_6H_2$ |
| 84. | 3,4,5-$F_3$—$C_6H_2$ |
| 85. | 2,3,4-$Cl_3$—$C_6H_2$ |
| 86. | 2,3,5-$Cl_3$—$C_6H_2$ |
| 87. | 2,3,6-$Cl_3$—$C_6H_2$ |
| 88. | 2,4,5-$Cl_3$—$C_6H_2$ |
| 89. | 2,4,6-$Cl_3$—$C_6H_2$ |
| 90. | 3,4,5-$Cl_3$—$C_6H_2$ |
| 91. | 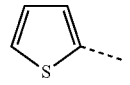 |
| 92. | 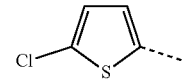 |
| 93. | 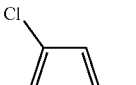 |
| 94. | 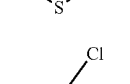 |
| 95. | 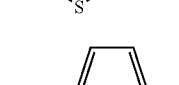 |
| 96. | 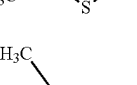 |
| 97. | 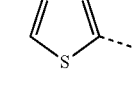 |
| 98. | 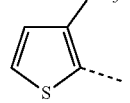 |

TABLE 2a-continued
| no. | R⁶ |
|---|---|
| 99. | 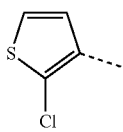 |
| 100. | 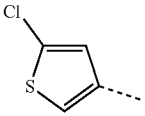 |
| 101. | 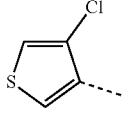 |
| 102. | 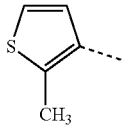 |
| 103. | 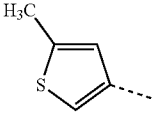 |
| 104. | 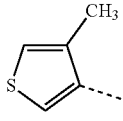 |
| 105. | 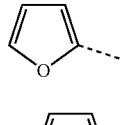 |
| 106. | 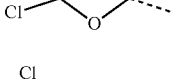 |
| 107. | 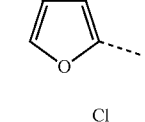 |
| 108. | 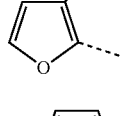 |
| 109. | 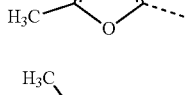 |
| 110. | 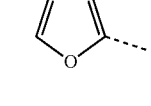 |
TABLE 2a-continued
| no. | R⁶ |
|---|---|
| 111. | 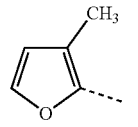 |
| 112. | 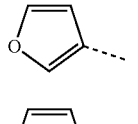 |
| 113. | 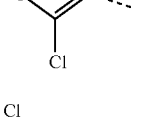 |
| 114. | 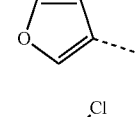 |
| 115. | 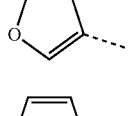 |
| 116. | 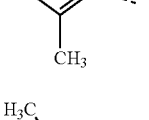 |
| 117. | 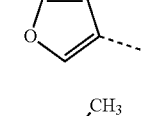 |
| 118. | 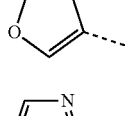 |
| 119. | 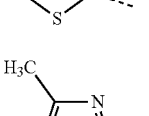 |
| 120. | 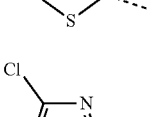 |
| 121. | 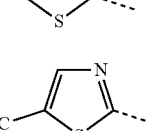 |
| 122. |  |

TABLE 2a-continued
| no. | R⁶ |
|---|---|
| 123. | 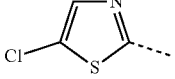 |
| 124. | 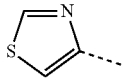 |
| 125. | 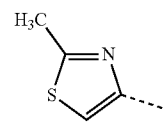 |
| 126. | 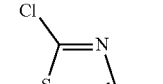 |
| 127. | 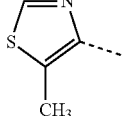 |
| 128. | 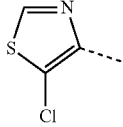 |
| 129. | 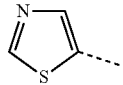 |
| 130. | 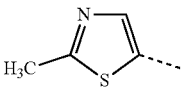 |
| 131. | 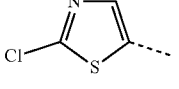 |
| 132. | 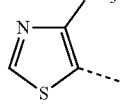 |
| 133. | 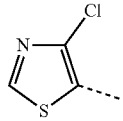 |
| 134. | 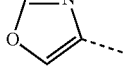 |
| 135. | 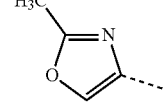 |
| 136. | 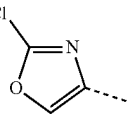 |
| 137. | 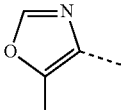 |
| 138. | 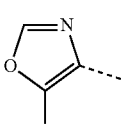 |
| 139. | 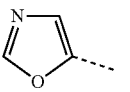 |
| 140. | 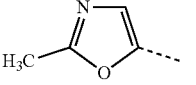 |
| 141. | 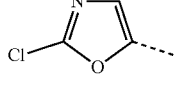 |
| 142. | 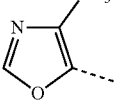 |
| 143. | 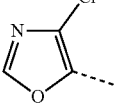 |
| 144. | 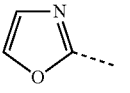 |
| 145. | 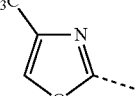 |
| 146. | 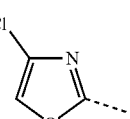 |
| 147. | 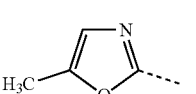 |

TABLE 2a-continued

| no. | R⁶ |
|---|---|
| 148. |  |

Further particular groups of embodiments relate to the diaminotriazine compounds of formula (I), wherein
$R^7$ and $R^{7'}$ is selected from the group consisting of hydrogen, halogen, $C_1$-$C_4$-alkyl, $C_2$-$C_6$-alkenyl, $C_2$-$C_6$-alkynyl, $C_1$-$C_6$-alkoxy, $C_1$-$C_6$-halogenoalkoxy, $C_3$-$C_6$-cycloalkyl, preferred H and F.

Preference is given to diaminotriazine compounds of formula (I.a), which corresponds to diaminotriazines of formula (I) wherein $R^1$ and $R^2$ is hydrogen Q is O, $R^a$ is F, $R^4$ is $CH_3$ and $R^{b1}$, $R^{b2}$, $R^{b3}$, $R^6$, $R^7$, $R^{7'}$ independently as defined in claim 1 or preferably defined below

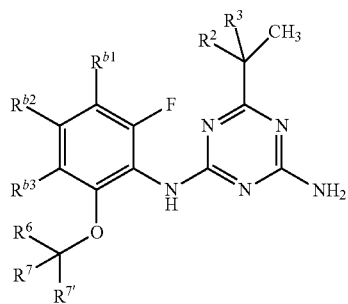

Particular embodiments of the compounds I are the following compounds: I-A, I-B, I-C, I-D, I-E, I-F. In these formulae, the substituents wherein $R^1$ and $R^2$ is hydrogen Q is O, $R^a$ is F, $R^4$ is $CH_3$, $R^7R^{7'}$ are H, H or F, F and $R^{b1}$, $R^{b2}$, $R^{b3}$ and $R^6$ as defined in claim in Table A:

I-A

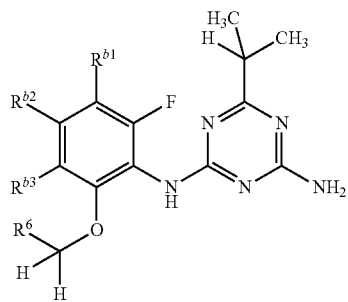

I-B

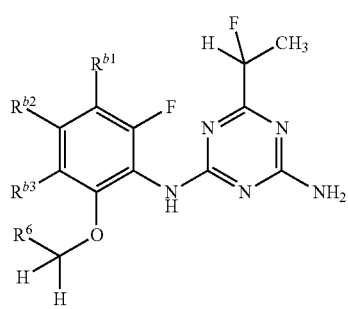

I-C

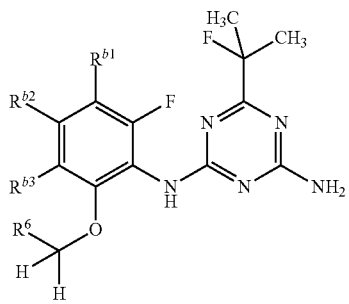

I-D

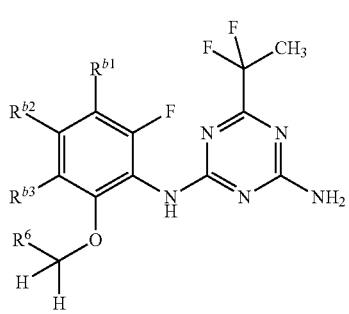

I-E

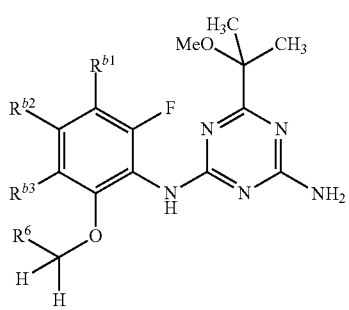

I-F

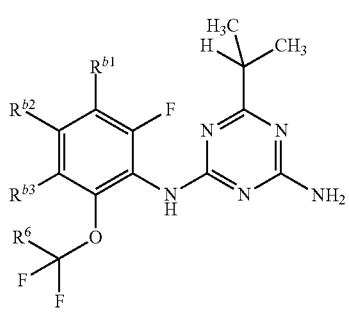

I-G

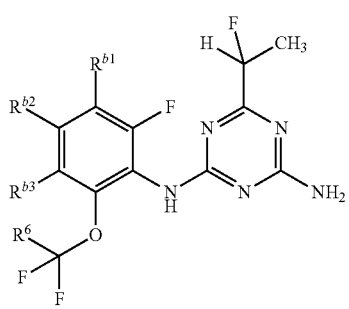

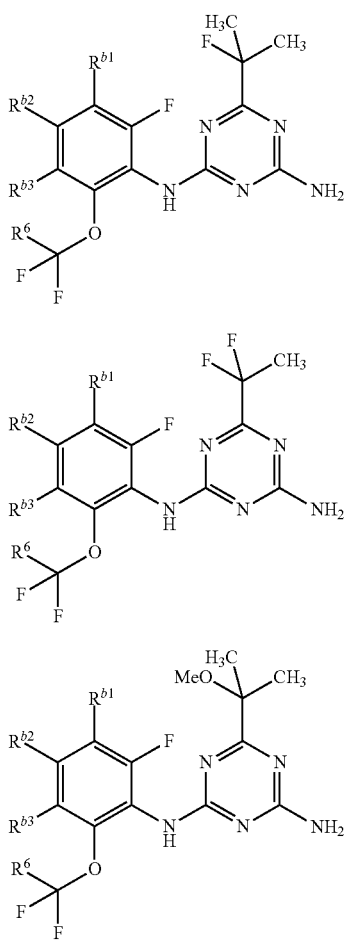

Table 1-1 Compounds of the formula I-A, I-B, I-C, I-D, I-E, I-F, I-G, I-H, I-I, I-J in which the meaning for the combination of $R^{b1}$, $R^{b2}$, $R^{b3}$ and $R^6$ for each individual compound corresponds in each case to one line of Table A (compounds I-A.1-1.A-1 to I-A.1-1.A-384, I-B.1-1.A-1 to I-B.1-1.A-384, I-C.1-1.A-1 to I-C.1-1.A-384, I-D.1-1.A-1 to I-D.1-1.A-384, I-E.1-1.A-1 to I-E.1-1.A-384, I-F.1-1.A-1 to I-F.1-1.A-384, I-G.1-1.A-1 to I-G.1-1.A-384, I-H.1-1.A-1 to I-H.1-1.A-384, I-I.1-1.A-1 to I-I.1-1.A-384, I-J.1-1.A-1 to I-J.1-1.A-384).

TABLE A

| No. | $R^{b1}$ | $R^{b2}$ | $R^{b3}$ | $R^6$ |
|---|---|---|---|---|
| A-1 | H | H | H | phenyl |
| A-2 | F | H | H | phenyl |
| A-3 | Cl | H | H | phenyl |
| A-4 | Br | H | H | phenyl |
| A-5 | H | F | H | phenyl |
| A-6 | F | F | H | phenyl |
| A-7 | Cl | F | H | phenyl |
| A-8 | Br | F | H | phenyl |
| A-9 | H | H | F | phenyl |
| A-10 | F | H | F | phenyl |
| A-11 | Cl | H | F | phenyl |
| A-12 | Br | H | F | phenyl |
| A-13 | H | F | F | phenyl |
| A-14 | F | F | F | phenyl |
| A-15 | Cl | F | F | phenyl |
| A-16 | Br | F | F | phenyl |
| A-17 | H | H | Cl | phenyl |
| A-18 | F | H | Cl | phenyl |
| A-19 | Cl | H | Cl | phenyl |
| A-20 | Br | H | Cl | phenyl |
| A-21 | H | F | Cl | phenyl |
| A-22 | F | F | Cl | phenyl |
| A-23 | Cl | F | Cl | phenyl |
| A-24 | Br | F | Cl | phenyl |
| A-25 | H | H | H | 2-fluorophenyl |
| A-26 | F | H | H | 2-fluorophenyl |
| A-27 | Cl | H | H | 2-fluorophenyl |
| A-28 | Br | H | H | 2-fluorophenyl |
| A-29 | H | F | H | 2-fluorophenyl |
| A-30 | F | F | H | 2-fluorophenyl |
| A-31 | Cl | F | H | 2-fluorophenyl |
| A-32 | Br | F | H | 2-fluorophenyl |
| A-33 | H | H | F | 2-fluorophenyl |
| A-34 | F | H | F | 2-fluorophenyl |
| A-35 | Cl | H | F | 2-fluorophenyl |
| A-36 | Br | H | F | 2-fluorophenyl |
| A-37 | H | F | F | 2-fluorophenyl |
| A-38 | F | F | F | 2-fluorophenyl |
| A-39 | Cl | F | F | 2-fluorophenyl |
| A-40 | Br | F | F | 2-fluorophenyl |
| A-41 | H | H | Cl | 2-fluorophenyl |
| A-42 | F | H | Cl | 2-fluorophenyl |
| A-43 | Cl | H | Cl | 2-fluorophenyl |
| A-44 | Br | H | Cl | 2-fluorophenyl |
| A-45 | H | F | Cl | 2-fluorophenyl |
| A-46 | F | F | Cl | 2-fluorophenyl |
| A-47 | Cl | F | Cl | 2-fluorophenyl |
| A-48 | Br | F | Cl | 2-fluorophenyl |
| A-49 | H | H | H | 3-fluorophenyl, |
| A-50 | F | H | H | 3-fluorophenyl, |
| A-51 | Cl | H | H | 3-fluorophenyl, |
| A-52 | Br | H | H | 3-fluorophenyl, |
| A-53 | H | F | H | 3-fluorophenyl, |
| A-54 | F | F | H | 3-fluorophenyl, |
| A-55 | Cl | F | H | 3-fluorophenyl, |
| A-56 | Br | F | H | 3-fluorophenyl, |
| A-57 | H | H | F | 3-fluorophenyl, |
| A-58 | F | H | F | 3-fluorophenyl, |
| A-59 | Cl | H | F | 3-fluorophenyl, |
| A-60 | Br | H | F | 3-fluorophenyl, |
| A-61 | H | F | F | 3-fluorophenyl, |
| A-62 | F | F | F | 3-fluorophenyl, |
| A-63 | Cl | F | F | 3-fluorophenyl, |
| A-64 | Br | F | F | 3-fluorophenyl, |
| A-65 | H | H | Cl | 3-fluorophenyl, |
| A-66 | F | H | Cl | 3-fluorophenyl, |
| A-67 | Cl | H | Cl | 3-fluorophenyl, |
| A-68 | Br | H | Cl | 3-fluorophenyl, |
| A-69 | H | F | Cl | 3-fluorophenyl, |
| A-70 | F | F | Cl | 3-fluorophenyl, |
| A-71 | Cl | F | Cl | 3-fluorophenyl, |
| A-72 | Br | F | Cl | 3-fluorophenyl, |
| A-73 | H | H | H | 2-chlorophenyl |
| A-74 | F | H | H | 2-chlorophenyl |
| A-75 | Cl | H | H | 2-chlorophenyl |
| A-76 | Br | H | H | 2-chlorophenyl |
| A-77 | H | F | H | 2-chlorophenyl |
| A-78 | F | F | H | 2-chlorophenyl |
| A-79 | Cl | F | H | 2-chlorophenyl |
| A-80 | Br | F | H | 2-chlorophenyl |
| A-81 | H | H | F | 2-chlorophenyl |
| A-82 | F | H | F | 2-chlorophenyl |
| A-83 | Cl | H | F | 2-chlorophenyl |
| A-84 | Br | H | F | 2-chlorophenyl |
| A-85 | H | F | F | 2-chlorophenyl |
| A-86 | F | F | F | 2-chlorophenyl |
| A-87 | Cl | F | F | 2-chlorophenyl |
| A-88 | Br | F | F | 2-chlorophenyl |
| A-89 | H | H | Cl | 2-chlorophenyl |
| A-90 | F | H | Cl | 2-chlorophenyl |
| A-91 | Cl | H | Cl | 2-chlorophenyl |
| A-92 | Br | H | Cl | 2-chlorophenyl |
| A-93 | H | F | Cl | 2-chlorophenyl |
| A-94 | F | F | Cl | 2-chlorophenyl |

TABLE A-continued

| No. | $R^{b1}$ | $R^{b2}$ | $R^{b3}$ | $R^6$ |
|---|---|---|---|---|
| A-95 | Cl | F | Cl | 2-chlorophenyl |
| A-96 | Br | F | Cl | 2-chlorophenyl |
| A-97 | H | H | H | 3-chlorophenyl |
| A-98 | F | H | H | 3-chlorophenyl |
| A-99 | Cl | H | H | 3-chlorophenyl |
| A-100 | Br | H | H | 3-chlorophenyl |
| A-101 | H | F | H | 3-chlorophenyl |
| A-102 | F | F | H | 3-chlorophenyl |
| A-103 | Cl | F | H | 3-chlorophenyl |
| A-104 | Br | F | H | 3-chlorophenyl |
| A-105 | H | H | F | 3-chlorophenyl |
| A-106 | F | H | F | 3-chlorophenyl |
| A-107 | Cl | H | F | 3-chlorophenyl |
| A-108 | Br | H | F | 3-chlorophenyl |
| A-109 | H | F | F | 3-chlorophenyl |
| A-110 | F | F | F | 3-chlorophenyl |
| A-111 | Cl | F | F | 3-chlorophenyl |
| A-112 | Br | F | F | 3-chlorophenyl |
| A-113 | H | H | Cl | 3-chlorophenyl |
| A-114 | F | H | Cl | 3-chlorophenyl |
| A-115 | Cl | H | Cl | 3-chlorophenyl |
| A-116 | Br | H | Cl | 3-chlorophenyl |
| A-117 | H | F | Cl | 3-chlorophenyl |
| A-118 | F | F | Cl | 3-chlorophenyl |
| A-119 | Cl | F | Cl | 3-chlorophenyl |
| A-120 | Br | F | Cl | 3-chlorophenyl |
| A-121 | H | H | H | 2,6-difluorophenyl |
| A-122 | F | H | H | 2,6-difluorophenyl |
| A-123 | Cl | H | H | 2,6-difluorophenyl |
| A-124 | Br | H | H | 2,6-difluorophenyl |
| A-125 | H | F | H | 2,6-difluorophenyl |
| A-126 | F | F | H | 2,6-difluorophenyl |
| A-127 | Cl | F | H | 2,6-difluorophenyl |
| A-128 | Br | F | H | 2,6-difluorophenyl |
| A-129 | H | H | F | 2,6-difluorophenyl |
| A-130 | F | H | F | 2,6-difluorophenyl |
| A-131 | Cl | H | F | 2,6-difluorophenyl |
| A-132 | Br | H | F | 2,6-difluorophenyl |
| A-133 | H | F | F | 2,6-difluorophenyl |
| A-134 | F | F | F | 2,6-difluorophenyl |
| A-135 | Cl | F | F | 2,6-difluorophenyl |
| A-136 | Br | F | F | 2,6-difluorophenyl |
| A-137 | H | H | Cl | 2,6-difluorophenyl |
| A-138 | F | H | Cl | 2,6-difluorophenyl |
| A-139 | Cl | H | Cl | 2,6-difluorophenyl |
| A-140 | Br | H | Cl | 2,6-difluorophenyl |
| A-141 | H | F | Cl | 2,6-difluorophenyl |
| A-142 | F | F | Cl | 2,6-difluorophenyl |
| A-143 | Cl | F | Cl | 2,6-difluorophenyl |
| A-144 | Br | F | Cl | 2,6-difluorophenyl |
| A-145 | H | H | H | 2,6-dichlorophenyl |
| A-146 | F | H | H | 2,6-dichlorophenyl |
| A-147 | Cl | H | H | 2,6-dichlorophenyl |
| A-148 | Br | H | H | 2,6-dichlorophenyl |
| A-149 | H | F | H | 2,6-dichlorophenyl |
| A-150 | F | F | H | 2,6-dichlorophenyl |
| A-151 | Cl | F | H | 2,6-dichlorophenyl |
| A-152 | Br | F | H | 2,6-dichlorophenyl |
| A-153 | H | H | F | 2,6-dichlorophenyl |
| A-154 | F | H | F | 2,6-dichlorophenyl |
| A-155 | Cl | H | F | 2,6-dichlorophenyl |
| A-156 | Br | H | F | 2,6-dichlorophenyl |
| A-157 | H | F | F | 2,6-dichlorophenyl |
| A-158 | F | F | F | 2,6-dichlorophenyl |
| A-159 | Cl | F | F | 2,6-dichlorophenyl |
| A-160 | Br | F | F | 2,6-dichlorophenyl |
| A-161 | H | H | Cl | 2,6-dichlorophenyl |
| A-162 | F | H | Cl | 2,6-dichlorophenyl |
| A-163 | Cl | H | Cl | 2,6-dichlorophenyl |
| A-164 | Br | H | Cl | 2,6-dichlorophenyl |
| A-165 | H | F | Cl | 2,6-dichlorophenyl |
| A-166 | F | F | Cl | 2,6-dichlorophenyl |
| A-167 | Cl | F | Cl | 2,6-dichlorophenyl |
| A-168 | Br | F | Cl | 2,6-dichlorophenyl |
| A-169 | H | H | H | 2-chloro-6-fluorophenyl |
| A-170 | F | H | H | 2-chloro-6-fluorophenyl |
| A-171 | Cl | H | H | 2-chloro-6-fluorophenyl |
| A-172 | Br | H | H | 2-chloro-6-fluorophenyl |
| A-173 | H | F | H | 2-chloro-6-fluorophenyl |
| A-174 | F | F | H | 2-chloro-6-fluorophenyl |
| A-175 | Cl | F | H | 2-chloro-6-fluorophenyl |
| A-176 | Br | F | H | 2-chloro-6-fluorophenyl |
| A-177 | H | H | F | 2-chloro-6-fluorophenyl |
| A-178 | F | H | F | 2-chloro-6-fluorophenyl |
| A-179 | Cl | H | F | 2-chloro-6-fluorophenyl |
| A-180 | Br | H | F | 2-chloro-6-fluorophenyl |
| A-181 | H | F | F | 2-chloro-6-fluorophenyl |
| A-182 | F | F | F | 2-chloro-6-fluorophenyl |
| A-183 | Cl | F | F | 2-chloro-6-fluorophenyl |
| A-184 | Br | F | F | 2-chloro-6-fluorophenyl |
| A-185 | H | H | Cl | 2-chloro-6-fluorophenyl |
| A-186 | F | H | Cl | 2-chloro-6-fluorophenyl |
| A-187 | Cl | H | Cl | 2-chloro-6-fluorophenyl |
| A-188 | Br | H | Cl | 2-chloro-6-fluorophenyl |
| A-189 | H | F | Cl | 2-chloro-6-fluorophenyl |
| A-190 | F | F | Cl | 2-chloro-6-fluorophenyl |
| A-191 | Cl | F | Cl | 2-chloro-6-fluorophenyl |
| A-192 | Br | F | Cl | 2-chloro-6-fluorophenyl |
| A-193 | H | H | H | 2-methoxyphenyl |
| A-194 | F | H | H | 2-methoxyphenyl |
| A-195 | Cl | H | H | 2-methoxyphenyl |
| A-196 | Br | H | H | 2-methoxyphenyl |
| A-197 | H | F | H | 2-methoxyphenyl |
| A-198 | F | F | H | 2-methoxyphenyl |
| A-199 | Cl | F | H | 2-methoxyphenyl |
| A-200 | Br | F | H | 2-methoxyphenyl |
| A-201 | H | H | F | 2-methoxyphenyl |
| A-202 | F | H | F | 2-methoxyphenyl |
| A-203 | Cl | H | F | 2-methoxyphenyl |
| A-204 | Br | H | F | 2-methoxyphenyl |
| A-205 | H | F | F | 2-methoxyphenyl |
| A-206 | F | F | F | 2-methoxyphenyl |
| A-207 | Cl | F | F | 2-methoxyphenyl |
| A-208 | Br | F | F | 2-methoxyphenyl |
| A-209 | H | H | Cl | 2-methoxyphenyl |
| A-210 | F | H | Cl | 2-methoxyphenyl |
| A-211 | Cl | H | Cl | 2-methoxyphenyl |
| A-212 | Br | H | Cl | 2-methoxyphenyl |
| A-213 | H | F | Cl | 2-methoxyphenyl |
| A-214 | F | F | Cl | 2-methoxyphenyl |
| A-215 | Cl | F | Cl | 2-methoxyphenyl |
| A-216 | Br | F | Cl | 2-methoxyphenyl |
| A-217 | H | H | H | 3-methoxyphenyl |
| A-218 | F | H | H | 3-methoxyphenyl |
| A-219 | Cl | H | H | 3-methoxyphenyl |
| A-220 | Br | H | H | 3-methoxyphenyl |
| A-221 | H | F | H | 3-methoxyphenyl |
| A-222 | F | F | H | 3-methoxyphenyl |
| A-223 | Cl | F | H | 3-methoxyphenyl |
| A-224 | Br | F | H | 3-methoxyphenyl |
| A-225 | H | H | F | 3-methoxyphenyl |
| A-226 | F | H | F | 3-methoxyphenyl |
| A-227 | Cl | H | F | 3-methoxyphenyl |
| A-228 | Br | H | F | 3-methoxyphenyl |
| A-229 | H | F | F | 3-methoxyphenyl |
| A-230 | F | F | F | 3-methoxyphenyl |
| A-231 | Cl | F | F | 3-methoxyphenyl |
| A-232 | Br | F | F | 3-methoxyphenyl |
| A-233 | H | H | Cl | 3-methoxyphenyl |
| A-234 | F | H | Cl | 3-methoxyphenyl |
| A-235 | Cl | H | Cl | 3-methoxyphenyl |
| A-236 | Br | H | Cl | 3-methoxyphenyl |
| A-237 | H | F | Cl | 3-methoxyphenyl |
| A-238 | F | F | Cl | 3-methoxyphenyl |
| A-239 | Cl | F | Cl | 3-methoxyphenyl |
| A-240 | Br | F | Cl | 3-methoxyphenyl |
| A-241 | H | H | H | 4-methoxyphenyl |
| A-242 | F | H | H | 4-methoxyphenyl |
| A-243 | Cl | H | H | 4-methoxyphenyl |
| A-244 | Br | H | H | 4-methoxyphenyl |
| A-245 | H | F | H | 4-methoxyphenyl |
| A-246 | F | F | H | 4-methoxyphenyl |
| A-247 | Cl | F | H | 4-methoxyphenyl |
| A-248 | Br | F | H | 4-methoxyphenyl |
| A-249 | H | H | F | 4-methoxyphenyl |
| A-250 | F | H | F | 4-methoxyphenyl |

TABLE A-continued

| No. | $R^{b1}$ | $R^{b2}$ | $R^{b3}$ | $R^6$ |
|---|---|---|---|---|
| A-251 | Cl | H | F | 4-methoxyphenyl |
| A-252 | Br | H | F | 4-methoxyphenyl |
| A-253 | H | F | F | 4-methoxyphenyl |
| A-254 | F | F | F | 4-methoxyphenyl |
| A-255 | Cl | F | F | 4-methoxyphenyl |
| A-256 | Br | F | F | 4-methoxyphenyl |
| A-257 | H | H | Cl | 4-methoxyphenyl |
| A-258 | F | H | Cl | 4-methoxyphenyl |
| A-259 | Cl | H | Cl | 4-methoxyphenyl |
| A-260 | Br | H | Cl | 4-methoxyphenyl |
| A-261 | H | F | Cl | 4-methoxyphenyl |
| A-262 | F | F | Cl | 4-methoxyphenyl |
| A-263 | Cl | F | Cl | 4-methoxyphenyl |
| A-264 | Br | F | Cl | 4-methoxyphenyl |
| A-265 | H | H | H | 2-methylphenyl |
| A-266 | F | H | H | 2-methylphenyl |
| A-267 | Cl | H | H | 2-methylphenyl |
| A-268 | Br | H | H | 2-methylphenyl |
| A-269 | H | F | H | 2-methylphenyl |
| A-270 | F | F | H | 2-methylphenyl |
| A-271 | Cl | F | H | 2-methylphenyl |
| A-272 | Br | F | H | 2-methylphenyl |
| A-273 | H | H | F | 2-methylphenyl |
| A-274 | F | H | F | 2-methylphenyl |
| A-275 | Cl | H | F | 2-methylphenyl |
| A-276 | Br | H | F | 2-methylphenyl |
| A-277 | H | F | F | 2-methylphenyl |
| A-278 | F | F | F | 2-methylphenyl |
| A-279 | Cl | F | F | 2-methylphenyl |
| A-280 | Br | F | F | 2-methylphenyl |
| A-281 | H | H | Cl | 2-methylphenyl |
| A-282 | F | H | Cl | 2-methylphenyl |
| A-283 | Cl | H | Cl | 2-methylphenyl |
| A-284 | Br | H | Cl | 2-methylphenyl |
| A-285 | H | F | Cl | 2-methylphenyl |
| A-286 | F | F | Cl | 2-methylphenyl |
| A-287 | Cl | F | Cl | 2-methylphenyl |
| A-288 | Br | F | Cl | 2-methylphenyl |
| A-289 | H | H | H | 3-methylphenyl |
| A-290 | F | H | H | 3-methylphenyl |
| A-291 | Cl | H | H | 3-methylphenyl |
| A-292 | Br | H | H | 3-methylphenyl |
| A-293 | H | F | H | 3-methylphenyl |
| A-294 | F | F | H | 3-methylphenyl |
| A-295 | Cl | F | H | 3-methylphenyl |
| A-296 | Br | F | H | 3-methylphenyl |
| A-297 | H | H | F | 3-methylphenyl |
| A-298 | F | H | F | 3-methylphenyl |
| A-299 | Cl | H | F | 3-methylphenyl |
| A-300 | Br | H | F | 3-methylphenyl |
| A-301 | H | F | F | 3-methylphenyl |
| A-302 | F | F | F | 3-methylphenyl |
| A-303 | Cl | F | F | 3-methylphenyl |
| A-304 | Br | F | F | 3-methylphenyl |
| A-305 | H | H | Cl | 3-methylphenyl |
| A-306 | F | H | Cl | 3-methylphenyl |
| A-307 | Cl | H | Cl | 3-methylphenyl |
| A-308 | Br | H | Cl | 3-methylphenyl |
| A-309 | H | F | Cl | 3-methylphenyl |
| A-310 | F | F | Cl | 3-methylphenyl |
| A-311 | Cl | F | Cl | 3-methylphenyl |
| A-312 | Br | F | Cl | 3-methylphenyl |
| A-313 | H | H | H | 4-methylphenyl |
| A-314 | F | H | H | 4-methylphenyl |
| A-315 | Cl | H | H | 4-methylphenyl |
| A-316 | Br | H | H | 4-methylphenyl |
| A-317 | H | F | H | 4-methylphenyl |
| A-318 | F | F | H | 4-methylphenyl |
| A-319 | Cl | F | H | 4-methylphenyl |
| A-320 | Br | F | H | 4-methylphenyl |
| A-321 | H | H | F | 4-methylphenyl |
| A-322 | F | H | F | 4-methylphenyl |
| A-323 | Cl | H | F | 4-methylphenyl |
| A-324 | Br | H | F | 4-methylphenyl |
| A-325 | H | F | F | 4-methylphenyl |
| A-326 | F | F | F | 4-methylphenyl |
| A-327 | Cl | F | F | 4-methylphenyl |
| A-328 | Br | F | F | 4-methylphenyl |
| A-329 | H | H | Cl | 4-methylphenyl |
| A-330 | F | H | Cl | 4-methylphenyl |
| A-331 | Cl | H | Cl | 4-methylphenyl |
| A-332 | Br | H | Cl | 4-methylphenyl |
| A-333 | H | F | Cl | 4-methylphenyl |
| A-334 | F | F | Cl | 4-methylphenyl |
| A-335 | Cl | F | Cl | 4-methylphenyl |
| A-336 | Br | F | Cl | 4-methylphenyl |
| A-337 | H | H | H | 2-thiophene |
| A-338 | F | H | H | 2-thiophene |
| A-339 | Cl | H | H | 2-thiophene |
| A-340 | Br | H | H | 2-thiophene |
| A-341 | H | F | H | 2-thiophene |
| A-342 | F | F | H | 2-thiophene |
| A-343 | Cl | F | H | 2-thiophene |
| A-344 | Br | F | H | 2-thiophene |
| A-345 | H | H | F | 2-thiophene |
| A-346 | F | H | F | 2-thiophene |
| A-347 | Cl | H | F | 2-thiophene |
| A-348 | Br | H | F | 2-thiophene |
| A-349 | H | F | F | 2-thiophene |
| A-350 | F | F | F | 2-thiophene |
| A-351 | Cl | F | F | 2-thiophene |
| A-352 | Br | F | F | 2-thiophene |
| A-353 | H | H | Cl | 2-thiophene |
| A-354 | F | H | Cl | 2-thiophene |
| A-355 | Cl | H | Cl | 2-thiophene |
| A-356 | Br | H | Cl | 2-thiophene |
| A-357 | H | F | Cl | 2-thiophene |
| A-358 | F | F | Cl | 2-thiophene |
| A-359 | Cl | F | Cl | 2-thiophene |
| A-360 | Br | F | Cl | 2-thiophene |
| A-361 | H | H | H | 3-thiophene |
| A-362 | F | H | H | 3-thiophene |
| A-363 | Cl | H | H | 3-thiophene |
| A-364 | Br | H | H | 3-thiophene |
| A-365 | H | F | H | 3-thiophene |
| A-366 | F | F | H | 3-thiophene |
| A-367 | Cl | F | H | 3-thiophene |
| A-368 | Br | F | H | 3-thiophene |
| A-369 | H | H | F | 3-thiophene |
| A-370 | F | H | F | 3-thiophene |
| A-371 | Cl | H | F | 3-thiophene |
| A-372 | Br | H | F | 3-thiophene |
| A-373 | H | F | F | 3-thiophene |
| A-374 | F | F | F | 3-thiophene |
| A-375 | Cl | F | F | 3-thiophene |
| A-376 | Br | F | F | 3-thiophene |
| A-377 | H | H | Cl | 3-thiophene |
| A-378 | F | H | Cl | 3-thiophene |
| A-379 | Cl | H | Cl | 3-thiophene |
| A-380 | Br | H | Cl | 3-thiophene |
| A-381 | H | F | Cl | 3-thiophene |
| A-382 | F | F | Cl | 3-thiophene |
| A-383 | Cl | F | Cl | 3-thiophene |
| A-384 | Br | F | Cl | 3-thiophene |

The diaminotriazine compounds of formula (I) according to the invention can be prepared by standard processes of organic chemistry, for example by the following process Process A)

The Azines of formula (I), wherein $R^1$ is H, $C_1$-$C_6$-alkyl, $C_1$-$C_6$-alkoxy-$C_1$-$C_6$-alkyl, $C_1$-$C_6$-alkoxy and $R^5$ is H, $C_1$-$C_6$-alkyl, $C_1$-$C_6$-alkoxy-$C_1$-$C_6$-alkyl, $C_1$-$C_6$-alkoxy, ($C_1$-$C_6$-alkyl)-carbonyl, can be prepared by reaction halotriazines of formula (II) with amines of formula (III) in the presence of a base and/or a catalyst, or in the presence of an acid as depicted in the following scheme 1:

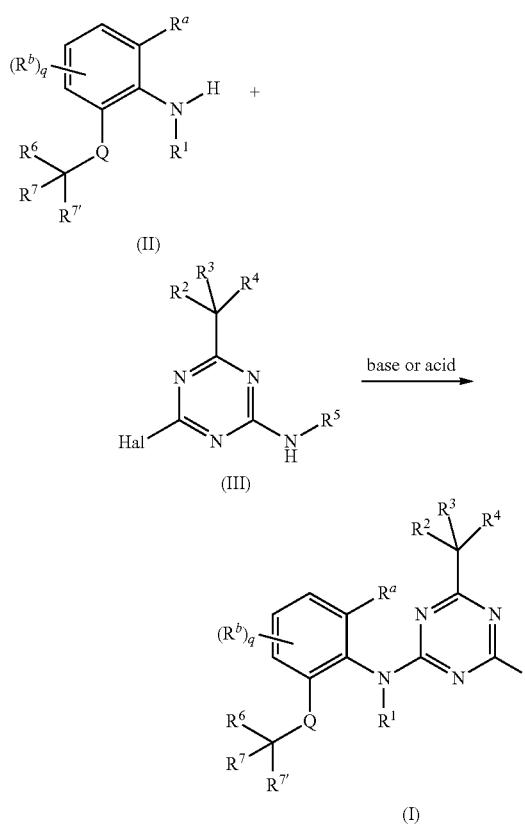

The variables Q, $R^a$, $R^b$, $R^2$, $R^3$ and $R^4$, $R^6$, $R^7$ and $R^{7'}$ have the meanings, in particular the preferred meanings, as in formula (I) mentioned above and Hal is halogen;
preferably Cl or Br;
particularly preferred Cl;
$R^1$ is H, $C_1$-$C_6$-alkyl, $C_1$-$C_6$-alkoxy-$C_1$-$C_6$-alkyl or $C_1$-$C_6$-alkoxy;
preferably $R^1$ is H or $C_1$-$C_6$-alkyl;
particularly preferred $R^1$ is H; and
$R^5$ is H, $C_1$-$C_6$-alkyl, $C_1$-$C_6$-alkoxy-$C_1$-$C_6$-alkyl, $C_1$-$C_6$-alkoxy or ($C_1$-$C_6$-alkyl)-carbonyl;
preferably $R^5$ is H, $C_1$-$C_6$-alkyl or ($C_1$-$C_6$-alkyl)-carbonyl;
particularly preferred $R^5$ is H or ($C_1$-$C_6$-alkyl)-carbonyl;
also particularly preferred $R^5$ is H;
also particularly preferred $R^5$ is ($C_1$-$C_6$-alkyl)-carbonyl;
especially preferred $R^5$ is H.

The reaction of the halotriazines of formula (III) with the amine compound of formula (II) is usually carried out from 50° C. to the boiling point of the reaction mixture, preferably from 50° C. to 150° C., particularly preferably from 60° C. to 100° C., in an inert organic solvent (e.g. P. Dao et al., Tetrahedron 2012, 68, 3856-3860).

The reaction can be carried out at atmospheric pressure or under elevated pressure, if appropriate, under an inert gas, continuously or batchwise.

The halotriazines of formula (III) and the compounds of formula (II) are used in equimolar amounts or the compounds of formula (II) are used in excess with regard to the halotriazines of formula (III). Preferably the molar ratio of the compounds of formula (II) to the halotriazines of formula (III) is in the range from 2:1 to 1:1, preferably 1.5:1 to 1:1, especially preferred 1.2:1. The reaction of the halotriazines of formula (III) with the compounds of formula (II) is carried out in an organic solvent.

Suitable in principle are all solvents which can dissolve the halotriazines of formula (III) and the amines of compounds (II) at least partly and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers as defined above.

The term solvent as used herein also includes mixtures of two or more of the above compounds.

The reaction of the halotriazines of formula (III) with the compounds of formula (II) is carried out in the presence of a base or an acid.

Examples of suitable bases include metal-containing bases and nitrogen-containing bases.

Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal and alkaline earth metal formates, acetates and other metal salts of carboxylic acids, such as sodium formate, sodium benzoate, lithium acetate, sodium acetate, potassium acetate, magnesium acetate, and calcium acetate; alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; alkali metal and alkaline earth metal alkoxides such as sodium methoxide, sodium ethoxide, potassium ethoxide, potassium tert-butoxide, potassium tert-pentoxide and dimethoxymagnesium; and furthermore organic bases, such as tertiary amines such as tri-$C_1$-$C_6$-alkylamines, for example triethylamine, trimethylamine, N-ethyldiisopropylamine, and N-methylpiperidine, pyridine, substituted pyridines such as collidine, lutidine, N-methylmorpholine and also bicyclic amines such as 1,8-diazabicyclo[5.4.0]undec-7-ene (DBU) or 1,5-diazabicyclo-[4.3.0]non-5-ene (DBN).

Preferred bases are alkali metal and alkaline earth metal alkoxides as defined above.

The term base as used herein also includes mixtures of two or more, preferably two of the above compounds. Particular preference is given to the use of one base.

The bases can be used in excess, preferably from 1 to 10, especially preferred from 2 to 4 base equivalents based on the halotriazines of formula (VI), and they may also be used as the solvent.

Example of suitable acids are inorganic acids like hydrofluoric acid, hydrochloric acid, hydrobromic acid, hydroiodic acid, phosphoric acid, sulfuric acid, p-toluenesulfonic acid; Lewis acids like boron trifluoride, aluminium chloride, ferric-III-chloride, tin-IV-chloride, titanium-IV-chloride and zinc-I-chloride, as well as organic acids like formic acid, acetic acid, propionic acid, oxalic acid, methylbenzenesulfonic acid, benzenesulfonic acid, camphorsulfonic acid, citric acid, trifluoroacetic acid, can be used.

Preferred bases are inorganic acids.

The acids are generally employed in excess or, if appropriate, can be used as a solvent.

The end of the reaction can easily be determined by the skilled worker by means of routine methods.

The reaction mixtures are worked up in a customary manner, for example by mixing with water, separation of the phases and, if appropriate, purification of the crude product.

The amine compounds of formula (II) required for the preparation of compounds of formula (I), are commercially available or can be prepared by analogy to known literature procedures (e.g. Barnes et al., WO/2007/067612).

The halo-triazines of formula (VI) required for the preparation of azines of formula (I), wherein $R^5$ is H, $C_1$-$C_6$-alkyl, $C_1$-$C_6$-alkoxy-$C_1$-$C_6$-alkyl or $C_1$-$C_6$-alkoxy, are known from the literature, are commercially available and/or can be prepared by analogy (e.g. J. K. Chakrabarti et al., Tetrahedron 1975, 31, 1879-1882) by reacting thiotriazines of formula (IV) with a halogen source (e.g. $Cl_2$) or other suitable halogenating agents (e.g. $SOCl_2$):

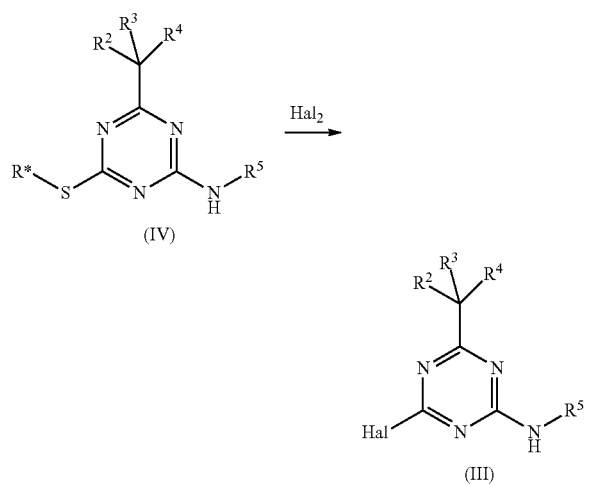

The variables $R^2$, $R^3$, and $R^4$ have the meanings, in particular the preferred meanings, as defined in formula (I) mentioned above;

Hal is halogen;
preferably $C_1$ or Br;
particularly preferred Cl;

$R^*$ is $C_1$-$C_6$-alkyl, $C_2$-$C_6$-haloalkyl or phenyl;
preferably $C_1$-$C_6$-alkyl or $C_2$-$C_6$-haloalkyl;
particularly preferred $C_1$-$C_6$-alkyl;
especially preferred $CH_3$; and $R^5$ is H, $C_1$-$C_6$-alkyl, $C_1$-$C_6$-alkoxy-$C_1$-$C_6$-alkyl, $C_1$-$C_6$-alkoxy;
particularly preferred H, $C_1$-$C_6$-alkoxy-$C_1$-$C_6$-alkyl or $C_1$-$C_6$-alkoxy;
especially preferred H, $CH_2OCH_3$ or $OCH_3$;
more preferred hydrogen.

The reaction of the thiotriazines of formula (IV) with the halogen (or halogenating agent) is usually carried out from 0° C. to the boiling point of the reaction mixture, preferably from 15° C. to the boiling point of the reaction mixture, particularly preferably from 15° C. to 40° C., in an inert organic solvent (e.g. J. K. Chakrabarti et al., Tetrahedron 1975, 31, 1879-1882).

The reaction can be carried out at atmospheric pressure or under elevated pressure, if appropriate under an inert gas, continuously or batch wise.

In the process according to the invention, the halogen is used in excess with regard to the thiotriazines of formula (IV).

The reaction of the thiotriazines of formula (IV) with the halogen is carried out in an organic solvent.

Suitable in principle are all solvents which are capable of dissolving the thiotriazines of formula (IV) and the halogen at least partly and preferably fully under reaction conditions.

Examples of suitable solvents are aliphatic hydrocarbons such as pentane, hexane, cyclohexane and mixtures of $C_5$-$C_8$-alkanes, halogenated hydrocarbons such as dichloromethane, 1,2-dichloroethane, chloroform and carbon tetrachloride; ethers such as diethyl ether, diisopropyl ether, tert.-butyl methylether (TBME), dioxane, anisole and tetrahydrofuran (THF), alcohols such as methanol, ethanol, n-propanol, isopropanol, n-butanol and tert.-butanol, as well as organic acids like formic acid, acetic acid, propionic acid, oxalic acid, citric acid, trifluoroacetic acid.

Preferred solvents are halogenated hydrocarbons and organic acids as defined above.

The term solvent as used herein also includes mixtures of two or more of the above compounds.

The end of the reaction can easily be determined by the skilled worker by means of routine methods.

The reaction mixtures are worked up in a customary manner, for example by mixing with water, separation of the phases and, if appropriate, chromatographic purification of the crude product.

The thiotriazines of formula (IV) required for the preparation of halotriazines of formula (III) can be prepared in accordance by reacting guanidine-salts of formula (V) with carbonyl compounds of formula (VI) in the presence of a base:

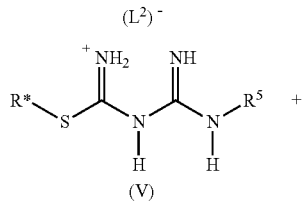

-continued

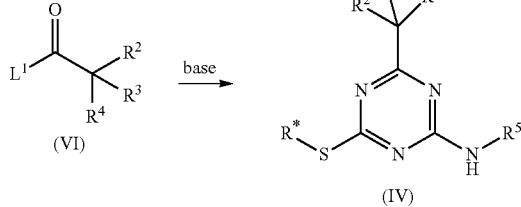

The variables $R^2$, $R^3$ and $R^4$ have the meanings, in particular the preferred meanings, as defined in formula (I) mentioned above;
- R* is $C_1$-$C_6$-alkyl, $C_2$-$C_6$-haloalkyl or phenyl;
  - preferably $C_1$-$C_6$-alkyl or $C_2$-$C_6$-haloalkyl;
  - particularly preferred $C_1$-$C_6$-alkyl;
  - especially preferred $CH_3$;
- $L^1$ is a nucleophilically displaceable leaving group such as halogen, CN, $C_1$-$C_6$-alkoxy, $C_1$-$C_6$-alkylcarbonyloxy or $C_1$-$C_6$-alkoxycarbonyloxy;
  - preferably halogen or $C_1$-$C_6$-alkoxy;
  - particularly preferred Cl or $C_1$-$C_6$-alkoxy,
  - also particularly preferred halogen;
  - especially preferred Cl; and
- $L^2$ is a nucleophilically displaceable leaving group such as halogen, $C_1$-$C_6$-alkylsulfonyloxy, $C_1$-$C_6$-haloalkylsulfonyloxy, $C_1$-$C_6$-alkoxysulfonyloxy or phenylsulfonyloxy;
  - preferably halogen or $C_1$-$C_6$-haloalkylsulfonyloxy;
  - particularly preferred halogen;
  - especially preferred I; and
- $R^5$ is H, $C_1$-$C_6$-alkyl, $C_1$-$C_6$-alkoxy-$C_1$-$C_6$-alkyl, $C_1$-$C_6$-alkoxy;
  - particularly preferred H, $C_1$-$C_6$-alkoxy-$C_1$-$C_6$-alkyl or $C_1$-$C_6$-alkoxy;
  - especially preferred H, $CH_2OCH_3$ or $OCH_3$;
  - more preferred hydrogen.

The reaction of the guanidine-salt of formula (V) with the carbonyl compound of formula (VI) is usually carried out at temperatures from 50° C. to the boiling point of the reaction mixture, preferably from 50° C. to 100° C.

The reaction can be carried out at atmospheric pressure or under elevated pressure, if appropriate under an inert gas, continuously or batch wise.

In one embodiment of the process according to the invention, the guanidine-salts of formula (V) and the carbonyl compound of formula (VI) are used in equimolar amounts.

In another embodiment of the process according to the invention, the carbonyl compound of formula (VI) is used in excess with regard to the guanidine-salts of formula (V).

Preferably the molar ratio of the carbonyl compound of formula (VI) to the guanidine-salt of formula (V) is in the range from 1.5:1 to 1:1, preferably 1.2:1 to 1:1, especially preferred 1.2:1, also especially preferred 1:1.

The reaction of the guanidine-salt of formula (V) with the carbonyl compound of formula (VI) is usually carried out in an organic solvent.

Suitable in principle are all solvents which are capable of dissolving the guanidine-salt of formula (V) and the carbonyl compound of formula (VI) at least partly and preferably fully under reaction conditions.

Examples of suitable solvents are halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), nitriles such as acetonitrile and propionitrile, as well as dipolar aprotic solvents such as sulfolane, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers and dipolar aprotic solvents as defined above.

More preferred solvents are ethers as defined above.

The term solvent as used herein also includes mixtures of two or more of the above compounds.

The reaction of the guanidine-salts of formula (V) with the carbonyl compound of formula (VI) is carried out in the presence of a base.

Examples of suitable bases include metal-containing bases and nitrogen-containing bases.

Examples of suitable metal-containing bases are inorganic compounds such as alkali metal and alkaline earth metal oxide, and other metal oxides, such as lithium oxide, sodium oxide, potassium oxide, magnesium oxide, calcium oxide and magnesium ox-ide, iron oxide, silver oxide; alkali metal and alkaline earth metal hydrides such as lithium hydride, sodium hydride, potassium hydride and calcium hydride; alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; and furthermore organic bases such as tertiary amines such as tri-$C_1$-$C_6$-alkylamines, for example triethylamine, trimethylamine, N-ethyl-diisopropylamine, and N-methylpiperidine, pyridine, substituted pyridines such as collidine, lutidine, N-methylmorpholine, and also bicyclic amines such as 1,8-diazabicyclo[5.4.0]undec-7-ene (DBU) or 1,5-diazabicyclo[4.3.0]non-5-ene (DBN).

Preferred bases are tri-$C_1$-$C_6$-alkylamines as defined above.

The term base as used herein also includes mixtures of two or more, preferably two of the above compounds. Particular preference is given to the use of one base.

The bases are generally employed in excess; however they can also be employed in equimolar amounts, or, if appropriate, can be used as solvent.

Preferably from 1 to 5 base equivalents, particularly preferred 3 base equivalents of base are used, based on the guanidine-salts of formula (V).

The end of the reaction can easily be determined by the skilled worker by means of routine methods.

The reaction mixtures are worked up in a customary manner, for example by mixing with water, separation of the phases and, if appropriate, chromatographic purification of the crude product.

The carbonyl compounds of formula (VI) required for the preparation of azines of formula (I) are known from the literature. They can be prepared in accordance and/or are commercially available.

The guanidine-salt of formula (V), wherein $L^2$ is iodine, required for the preparation of thiotriazines of formula (IV) is known from the literature (e.g. M. Freund et al., Chem. Ber. 1901, 34, 3110-3122; H. Eilingsfeld et al., Chem. Ber. 1967, 100, 1874-1891).

Process B)

The Azines of formula (I) can be prepared by reaction halotriazines of formula (II) with amines of formula (III) in the presence of a base and/or a catalyst or in the presence of an acid as depicted in the following scheme 2:

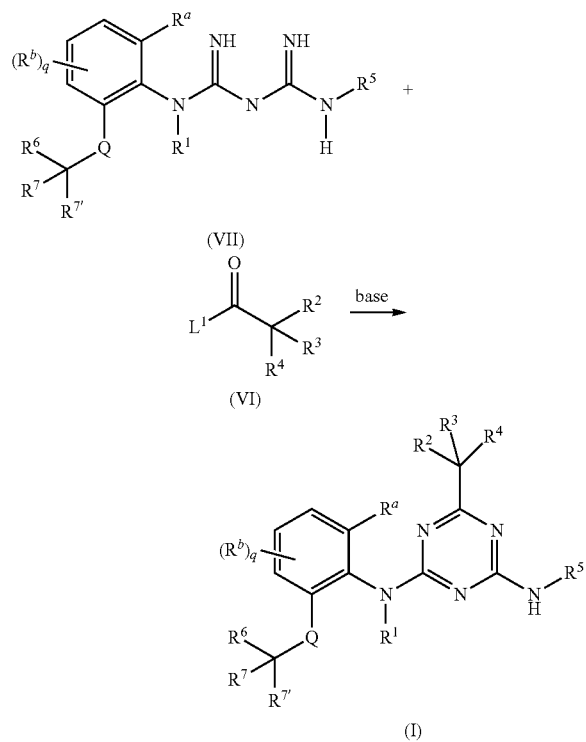

The variables Q, $R^a$, $R^b$, $R^2$, $R^3$, $R^4$, $R^6$, $R^7$ and $R^{7'}$ have the meanings, in particular the preferred meanings, as in formula (I) mentioned above and $L^1$ is a displaceable leaving group such as halogen, CN, $C_1$-$C_6$-alkoxy, $C_1$-$C_6$-alkoxycarbonyl, $C_1$-$C_6$-alkylcarbonyloxy or $C_1$-$C_6$-alkoxycarbonyloxy;
preferably halogen or $C_1$-$C_6$-alkoxy;
particularly preferred Cl or $C_1$-$C_6$-alkoxy, also particularly preferred halogen;
especially preferred Cl $R^1$ is H, $C_1$-$C_6$-alkyl, $C_1$-$C_6$-alkoxy-$C_1$-$C_6$-alkyl or $C_1$-$C_6$-alkoxy;
preferably $R^1$ is H or $C_1$-$C_6$-alkyl;
particularly preferred $R^1$ is H; and $R^5$ is H, $C_1$-$C_6$-alkyl, $C_1$-$C_6$-alkoxy-$C_1$-$C_6$-alkyl, $C_1$-$C_6$-alkoxy or ($C_1$-$C_6$-alkyl)-carbonyl;
preferably $R^5$ is H, $C_1$-$C_6$-alkyl or ($C_1$-$C_6$-alkyl)-carbonyl;
particularly preferred $R^5$ is H or ($C_1$-$C_6$-alkyl)-carbonyl;
also particularly preferred $R^5$ is H;
also particularly preferred $R^5$ is ($C_1$-$C_6$-alkyl)-carbonyl;
especially preferred $R^5$ is H.

The reaction of biguanidines of formula (VII) with carbonyl compounds of formula (VI) is usually carried out at temperatures from 50° C. to the boiling point of the reaction mixture, preferably from 50° C. to 200° C. (e.g. R. Sathunuru et al., J. Heterocycl. Chem. 2008, 45, 1673-1678).

The reaction can be carried out at atmospheric pressure or under elevated pressure, if appropriate under an inert gas, continuously or batchwise.

In one embodiment of the process according to the invention, the biguanidines of formula (VII) and the carbonyl compounds of formula (VI) are used in equimolar amounts.

In another embodiment of the process according to the invention, the carbonyl compounds of formula (VI) are used in excess with regard to the biguanidines of formula (VII).

Preferably the molar ratio of the carbonyl compounds of formula (VIII) to the biguanidines of formula (VII) is in the range from 1.5:1 to 1:1, preferably 1.2:1 to 1:1, especially preferred 1.2:1, also especially preferred 1:1.

The reaction of the biguanidines of formula (VII) with the carbonyl compounds of formula (VI) is carried out in an organic solvent.

Suitable in principle are all solvents which are capable of dissolving the biguanidines of formula (VII) and the carbonyl compounds of formula (VI) at least partly and preferably fully under reaction conditions.

Examples of suitable solvents are aliphatic hydrocarbons such as pentane, hexane, cyclohexane, nitromethane and mixtures of $C_5$-$C_8$-alkanes; romatic hydrocarbons such as benzene, chlorobenzene, toluene, cresols, o-, m- and p-xylene; halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), nitriles such as acetonitrile and propionitrile, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers and dipolar aprotic solvents as defined above. More preferred solvents are ethers as defined above.

The term solvent as used herein also includes mixtures of two or more of the above compounds.

The reaction of the biguanidines of formula (VII) with the carbonyl compounds of formula (VIII) is carried out in the presence of a base.

Examples of suitable bases include metal-containing bases and nitrogen-containing bases.

Examples of suitable metal-containing bases are inorganic compounds such as alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; and furthermore organic bases, such as tertiary amines such as tri-$C_1$-$C_6$-alkylamines, for example triethylamine, trimethylamine, N-ethyldiisopropylamine, and N-methylpiperidine, pyridine, substituted pyridines such as collidine, lutidine, N-methylmorpholine and 4-dimethylaminopyridine (DMAP), and also bicyclic amines such as 1,8-diazabicyclo[5.4.0]undec-7-ene (DBU) or 1,5-diazabicyclo[4.3.0]non-5-ene (DBN).

Preferred bases are tri-$C_1$-$C_6$-alkylamines as defined above. The term base as used herein also includes mixtures of two or more, preferably two of the above compounds. Particular preference is given to the use of one base. The bases are generally employed in excess; however they can also be employed in equimolar amounts, or, if appropriate, can be used as solvent. Preferably from 1 to 5 base equivalents, particularly preferred 3 base equivalents of base are used, based on the biguanidines of formula (VII). The end of the reaction can easily be determined by the skilled worker by means of routine methods.

The reaction mixtures are worked up in a customary manner, for example by mixing with water, separation of the phases and, if appropriate, chromatographic purification of the crude product.

Some of the intermediates and end products are obtained in the form of viscous oils, which can be purified or freed from volatile components under reduced pressure and at moderately elevated temperature.

If the intermediates and the end products are obtained as solid, purification can also be carried out by recrystallisation or digestion.

The carbonyl compounds of formula (VI) required for the preparation of azines of formula (I) are known in the art and/or are commercially available.

The biguanidines of formula (VII) required for the preparation of azines of formula (I) can be prepared by reacting cyanoguanidines of formula (IX) with amines of formula (II) in the presence of an acid:

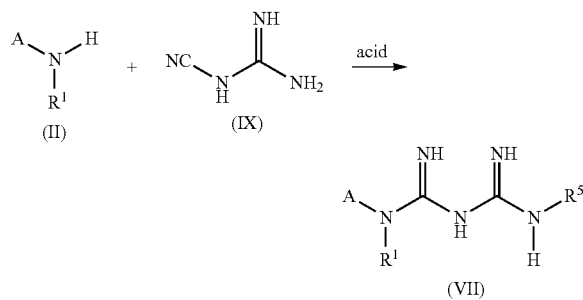

wherein A is represented by the moiety

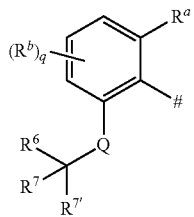

The variables Q, $R^a$, $R^b$, $R^2$, $R^3$, $R^4$, $R^6$, $R^7$ and $R^{7'}$ have the meanings, in particular the preferred meanings, as in formula (I) mentioned above and $R^1$ is H, $C_1$-$C_6$-alkyl, $C_1$-$C_6$-alkoxy-$C_1$-$C_6$-alkyl or $C_1$-$C_6$-alkoxy;
  preferably $R^1$ is H or $C_1$-$C_6$-alkyl;
  particularly preferred $R^1$ is H; and
$R^5$ is H, $C_1$-$C_6$-alkyl, $C_1$-$C_6$-alkoxy-$C_1$-$C_6$-alkyl, $C_1$-$C_6$-alkoxy or ($C_1$-$C_6$-alkyl)-carbonyl;
  preferably $R^5$ is H, $C_1$-$C_6$-alkyl or ($C_1$-$C_6$-alkyl)-carbonyl;
  particularly preferred $R^5$ is H or ($C_1$-$C_6$-alkyl)-carbonyl;
  also particularly preferred $R^5$ is H;
  also particularly preferred $R^5$ is ($C_1$-$C_6$-alkyl)-carbonyl;
  especially preferred $R^5$ is H.

The reaction of guanidines of formula (IX) with amines of formula (II) is usually carried out from 50° C. to 150° C., preferably from 80° C. to 130° C.

Microwave-Technology was used where applicable (e.g. C. O. Kappe, A. Stadler, Microwaves in Organic and Medicinal Chemistry, Weinheim 2012).

The reaction can be carried out at atmospheric pressure or under elevated pressure, if appropriate under an inert gas, continuously or batchwise.

In one embodiment of the process according to the invention, the guanidines of formula (IX) and the amines of formula (II) are used in equimolar amounts.

In another embodiment of the process according to the invention, the amines of formula (II) are used in excess with regard to the guanidines of formula (IX).

Preferably the molar ratio of the amines of formula (II) to the guanidines of formula (IX) is in the range from 2:1 to 1:1, preferably 1.5:1 to 1:1, especially preferred 1:1.

The reaction of the guanidines of formula (IX) with the amines of formula (II) is carried out in an organic solvent.

Suitable in principle are all solvents which are capable of dissolving the guanidines of formula (IX) and the amines of formula (II) at least partly and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, as well as dipolar aprotic solvents such as sulfolane, dimethylsulfoxide, N,Ndimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers, nitriles and dipolar aprotic solvents as defined above.

More preferred solvents are nitriles as defined above.

The term solvent as used herein also includes mixtures of two or more solvents.

The reaction of the guanidines of formula (IX) with the amines of formula (II) is carried out in the presence of an acid.

Example of suitable acids are inorganic acids like hydrofluoric acid, hydrochloric acid, hydrobromic acid, hydroiodic acid, phosphoric acid, sulfuric acid, p-toluenesulfonic acid; Lewis acids like boron trifluoride, aluminium chloride, ferric-III-chloride, tin-IV-chloride, titanium-IV-chloride and zinc-II-chloride, as well as organic acids like formic acid, acetic acid, propionic acid, oxalic acid, methylbenzenesulfonic acid, benzenesulfonic acid, camphorsulfonic acid, citric acid, trifluoroacetic acid, can be used.

The acids are generally employed in excess or, if appropriate, can be used as solvent.

Work up can be carried out in a known manner.

The guanidines of formula (IX) required for the preparation of biguanides of formula (VII) are commercially available or can be prepared in accordance with literature procedures (e.g. J. L. LaMattina et al., J. Med. Chem. 1990, 33, 543-552; A. Perez-Medrano et al., J. Med. Chem. 2009, 52, 3366-3376).

The amines of formula (II) required for the preparation of biguanidines of formula (VII) are commercially available or can be prepared in accordance with known literature procedures (e.g. Barnes et al., WO/2007/067612).

The compounds of formula (I) have herbicidal activity. Therefore, they can be used for controlling unwanted or undesired plants or vegetation. They can also be used in a method for controlling unwanted or undesired plants or vegetation, which method comprises allowing at least one compound of formula (I) or a salt thereof to act on plants, their environment or on seed. In order to allow the compound of formula (I) or a salt thereof to act on plants, their environment or on seed the compounds of the invention are applied to the plants, their environment or to the seed of said plants.

To widen the spectrum of action and to achieve synergistic effects, the diaminotriazine compounds of formula (I) may be mixed with a large number of representatives of other herbicidal or growth-regulating active ingredient groups and then applied concomitantly.

Suitable components for mixtures are, for example, herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

The invention also relates to combinations of diaminotriazine compounds of formula (I) with at least one further herbicide B and/or at least one safener C.

The further herbicidal compound B (component B) is in particular selected from the herbicides of class b1) to b15):
  b1) lipid biosynthesis inhibitors;
  b2) acetolactate synthase inhibitors (ALS inhibitors);
  b3) photosynthesis inhibitors;
  b4) protoporphyrinogen-IX oxidase inhibitors,
  b5) bleacher herbicides;
  b6) enolpyruvyl shikimate 3-phosphate synthase inhibitors (EPSP inhibitors);
  b7) glutamine synthetase inhibitors;
  b8) 7,8-dihydropteroate synthase inhibitors (DHP inhibitors);
  b9) mitosis inhibitors;
  b10) inhibitors of the synthesis of very long chain fatty acids (VLCFA inhibitors);
  b11) cellulose biosynthesis inhibitors;
  b12) decoupler herbicides;
  b13) auxinic herbicides;
  b14) auxin transport inhibitors; and
  b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothall and its salts, etobenzanid, flamprop, flamprop-isopropyl, flamprop-methyl, flamprop-M-isopropyl, flamprop-M-methyl, fluorenol, fluorenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters; including their agriculturally acceptable salts or derivatives such as ethers, esters or amides.

Preference is given to those compositions according to the present invention comprising at least one herbicide B selected from herbicides of class b1, b6, b9, b10 and b11.

Examples of herbicides B which can be used in combination with the compounds of formula (I) according to the present invention are:
  b1) from the group of the lipid biosynthesis inhibitors:
    ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim,
  4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, thiocarbanil, triallate and vemolate;

b2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron,
imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulammethyl, diclosulam, flumetsulam, florasulam, metosulam, penoxsulam, pyrimisulfan and pyroxsulam,
pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8),
sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;
among these, a preferred embodiment of the invention relates to those compositions comprising at least one imidazolinone herbicide;
b3) from the group of the photosynthesis inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazon, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide.

Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlomethoxyfen, cinidonethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacetmethyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1/-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluorophenoxy]-3-methoxy-but-2-enoate [CAS 948893-00-3], and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:
PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, clomazone, fenquintrione, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole and flumeturon;

b6) from the group of the EPSP synthase inhibitors:
glyphosate, glyphosate-isopropylammonium, glyphosate-potassiumandglyphosate-trimesium (sulfosate);

b7) from the group of the glutamine synthase inhibitors:
bilanaphos (bialaphos), bilanaphos-sodium, glufosinate, glufosinate-P and glufosinate-ammonium;

b8) from the group of the DHP synthase inhibitors:
asulam;

b9) from the group of the mitosis inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorothal, chlorothal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors:

chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9 the isoxazoline compounds of the formula (I) I are known in the art, e.g. from WO 2006/024820, WO 2006/037945, WO 2007/071900 and WO 2007/096576;

among the VLCFA inhibitors, preference is given to chloroacetam ides and oxyacetamides;

b11) from the group of the cellulose biosynthesis inhibitors:

chlorthiamid, dichlobenil, flupoxam, isoxaben and 1-Cyclohexyl-5-pentafluorophenyloxy-1$^4$-[1,2,4,6]thiatriazin-3-ylamine;

b12) from the group of the decoupler herbicides:

dinoseb, dinoterb and DNOC and its salts;

b13) from the group of the auxinic herbicides:

2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters and triclopyr and its salts and esters;

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothall and its salts, etobenzanid, flamprop, flamprop-isopropyl, flamprop-methyl, flamprop-M-isopropyl, flamprop-M-methyl, fluorenol, fluorenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam and tridiphane.

Preferred herbicides B that can be used in combination with the compounds of the formula (I) according to the present invention are:

b1) from the group of the lipid biosynthesis inhibitors: clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312-337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethy[1,1'-biphenyl]-3-yl)-5,6-dihydro-2,2,6,6-tetramethyl-5-oxo-2H-pyran-3-yl carbonic acid methyl ester (CAS 1033760-58-5); benfuresate, dimepiperate, EPTC, esprocarb, ethofumesate, molinate, orbencarb, prosulfocarb, thiobencarb and triallate;

b2) from the group of the ALS inhibitors:
amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone;

b3) from the group of the photosynthesis inhibitors: ametryn, amicarbazone, atrazine, bentazon, bentazone-sodium, bromoxynil and its salts and esters, chloridazone, chlorotoluron, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine and thidiazuron;

b4) from the group of the protoporphyrinogen-IX oxidase inhibitors:
acifluorfen-sodium, bencarbazone, benzfendizone, butafenacil, carfentrazone-ethyl, cinidon-ethyl, flufenpyr-ethyl, flumiclorac-pentyl, flumioxazin, fluoroglycofen-ethyl, fomesafen, lactofen, oxadiargyl, oxadiazon, oxyfluorfen, pentoxazone, pyraflufen-ethyl, saflufenacil, sulfentrazone, tiafenacil, ethyl [3-[2-chloro-4-fluoro-5-(1-methyl-6-trifluoromethyl-2,4-dioxo-1,2,3,4-tetrahydro-pyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1/-pyrazole-1-carboxamide (CAS 915396-43-9), N-ethyl-3-(2-chloro-6-fluoro-4-trifluoromethylphenoxy)-5-methyl-1/-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione; 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:
aclonifen, amitrole, beflubutamid, benzobicyclon, bicyclopyrone, clomazone, diflufenican, fenquintrione, fluometuron, flurochloridone, flurtamone, isoxaflutole, mesotrione, norflurazon, picolinafen, pyrasulfotole, pyrazolynate, sulcotrione, tefuryltrione, tembotrione, topramezone and 4-(3-trifluoromethylphenoxy)-2-(4-trifluoromethylphenyl)pyrimidine (CAS 180608-33-7);

b6) from the group of the EPSP synthase inhibitors:
glyphosate, glyphosate-isopropylammonium, glyphosate-potassium and glyphosate-trimesium (sulfosate);

b7) from the group of the glutamine synthase inhibitors: glufosinate, glufosinate-P, glufosinate-ammonium;

b8) from the group of the DHP synthase inhibitors: asulam;

b9) from the group of the mitosis inhibitors:
benfluralin, dithiopyr, ethalfluralin, oryzalin, pendimethalin, thiazopyr and trifluralin;

b10) from the group of the VLCFA inhibitors:

acetochlor, alachlor, anilofos, butachlor, cafenstrole, dimethenamid, dimethenamid-P, fentrazamide, flufenacet, mefenacet, metazachlor, metolachlor, S-metolachlor, napronilide, napropamide, napropamide-M, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors: dichlobenil, flupoxam, isoxaben and 1-Cyclohexyl-5-pentafluorophenyloxy-14-[1,2,4,6]thiatriazin-3-ylamine;

b13) from the group of the auxinic herbicides:
2,4-D and its salts and esters, aminocyclopyrachlor and its salts and esters, aminopyralid and its salts such as aminopyralid-dimethylammonium, aminopyralid-tris(2-hydroxypropy)ammonium and its esters, clopyralid and its salts and esters, dicamba and its salts and esters, dichlorprop-P and its salts and esters, fluroxypyr-meptyl, halauxifen and its salts and esters (CAS 943832-60-8), MCPA and its salts and esters, MCPB and its salts and esters, mecoprop-P and its salts and esters, picloram and its salts and esters, quinclorac, quinmerac and triclopyr and its salts and esters;

b14) from the group of the auxin transport inhibitors: diflufenzopyr and diflufenzopyr-sodium;

b15) from the group of the other herbicides: bromobutide, cinmethylin, cumyluron, cyclopyrimorate (CAS 499223-49-3) and its salts and esters, dalapon, difenzoquat, difenzoquat-metilsulfate, DSMA, dymron (=daimuron), flamprop, flamprop-isopropyl, flampropmethyl, flamprop-M-isopropyl, flamprop-M-methyl, indanofan, indaziflam, metam, methylbromide, MSMA, oxaziclomefone, pyributicarb, triaziflam and tridiphane.

Particularly preferred herbicides B that can be used in combination with the compounds A of the formula (I) according to the present invention are:

b1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); esprocarb, prosulfocarb, thiobencarb and triallate;

b2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, nicosulfuron, penoxsulam, propoxycarbazon-sodium, propyrisulfuron, pyrazosulfuron-ethyl, pyroxsulam, rimsulfuron, sulfosulfuron, thiencarbazon-methyl, tritosulfuron and triafamone;

b3) from the group of the photosynthesis inhibitors: ametryn, atrazine, diuron, fluometuron, hexazinone, isoproturon, linuron, metribuzin, paraquat, paraquat-dichloride, propanil, terbutryn and terbuthylazine;

b4) from the group of the protoporphyrinogen-IX oxidase inhibitors: flumioxazin, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6) 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;

b5) from the group of the bleacher herbicides: amitrole, bicyclopyrone, clomazone, diflufenican, fenquintrione, fluometuron, flurochloridone, isoxaflutole, mesotrione, picolinafen, sulcotrione, tefuryltrione, tembotrione and topramezone;

b6) from the group of the EPSP synthase inhibitors: glyphosate, glyphosate-isopropylammonium and glyphosate-trimesium (sulfosate);

b7) from the group of the glutamine synthase inhibitors: glufosinate, glufosinate-P and glufosinate-ammonium;

b9) from the group of the mitosis inhibitors: pendimethalin and trifluralin;

b10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

b11) from the group of the cellulose biosynthesis inhibitors: isoxaben;

b13) from the group of the auxinic herbicides: 2,4-D and its salts and esters such as clacyfos, and aminocyclopyrachlor and its salts and esters, aminopyralid and its salts and its esters, clopyralid and its salts and esters, dicamba and its salts and esters, fluroxypyr-meptyl, quinclorac and quinmerac;

b14) from the group of the auxin transport inhibitors: diflufenzopyr and diflufenzopyr-sodium, b15) from the group of the other herbicides: dymron (=daimuron), indanofan, indaziflam, oxaziclomefone and triaziflam.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-oleamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanolammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isooctyl.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isooctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isooctyl, MCPA-isopropyl, MCPA-isopropylammonium, MCPA-methyl, MCPA-oleamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-oleamine and clopyralid-tris-(2-hydroxypropyl)ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isooctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium.

Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and aminopyralid-tris(2-hydroxypropyl)ammonium.

Suitable salts of glyphosate are for example glyphosate-ammonium, glyphosate-diammonium, glyphosate-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isooctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinclorac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

Particularly preferred herbicidal compounds B are the herbicides B as defined above; in particular the herbicides B.1-B.203 listed below in table B:

TABLE B

| Herbicide B | |
|---|---|
| B.1 | clethodim |
| B.2 | clodinafop-propargyl |

TABLE B-continued

| | Herbicide B |
|---|---|
| B.3 | cycloxydim |
| B.4 | cyhalofop-butyl |
| B.5 | fenoxaprop-ethyl |
| B.6 | fenoxaprop-P-ethyl |
| B.7 | metamifop |
| B.8 | pinoxaden |
| B.9 | profoxydim |
| B.10 | sethoxydim |
| B.11 | tepraloxydim |
| B.12 | tralkoxydim |
| B.13 | esprocarb |
| B.14 | ethofumesate |
| B.15 | molinate |
| B.16 | prosulfocarb |
| B.17 | thiobencarb |
| B.18 | triallate |
| B.19 | bensulfuron-methyl |
| B.20 | bispyribac-sodium |
| B.21 | cloransulam-methyl |
| B.22 | chlorsulfuron |
| B.23 | clorimuron |
| B.24 | cyclosulfamuron |
| B.25 | diclosulam |
| B.26 | florasulam |
| B.27 | flumetsulam |
| B.28 | flupyrsulfuron-methyl-sodium |
| B.29 | foramsulfuron |
| B.30 | imazamox |
| B.31 | imazamox-ammonium |
| B.32 | imazapic |
| B.33 | imazapic-ammonium |
| B.34 | imazapic-isopropylammonium |
| B.35 | imazapyr |
| B.36 | imazapyr-ammonium |
| B.37 | imazapyr-isopropylammonium |
| B.38 | imazaquin |
| B.39 | imazaquin-ammonium |
| B.40 | imazethapyr |
| B.41 | imazethapyr-ammonium |
| B.42 | imazethapyr-isopropylammonium |
| B.43 | imazosulfuron |
| B.44 | iodosulfuron-methyl-sodium |
| B.45 | iofensulfuron |
| B.46 | iofensulfuron-sodium |
| B.47 | mesosulfuron-methyl |
| B.48 | metazosulfuron |
| B.49 | metsulfuron-methyl |
| B.50 | metosulam |
| B.51 | nicosulfuron |
| B.52 | penoxsulam |
| B.53 | propoxycarbazon-sodium |
| B.54 | pyrazosulfuron-ethyl |
| B.55 | pyribenzoxim |
| B.56 | pyriftalid |
| B.57 | pyroxsulam |
| B.58 | propyrisulfuron |
| B.59 | rimsulfuron |
| B.60 | sulfosulfuron |
| B.61 | thiencarbazone-methyl |
| B.62 | thifensulfuron-methyl |
| B.63 | tribenuron-methyl |
| B.64 | tritosulfuron |
| B.65 | triafamone |
| B.66 | ametryne |
| B.67 | atrazine |
| B.68 | bentazon |
| B.69 | bromoxynil |
| B.70 | bromoxynil-octanoate |
| B.71 | bromoxynil-heptanoate |
| B.72 | bromoxynil-potassium |
| B.73 | diuron |
| B.74 | fluometuron |
| B.75 | hexazinone |
| B.76 | isoproturon |
| B.77 | linuron |
| B.78 | metamitron |
| B.79 | metribuzin |
| B.80 | propanil |
| B.81 | simazin |
| B.82 | terbuthylazine |
| B.83 | terbutryn |
| B.84 | paraquat-dichloride |
| B.85 | acifluorfen |
| B.86 | butafenacil |
| B.87 | carfentrazone-ethyl |
| B.88 | flumioxazin |
| B.89 | fomesafen |
| B.90 | oxadiargyl |
| B.91 | oxyfluorfen |
| B.92 | pyraflufen |
| B.93 | pyraflufen-ethyl |
| B.94 | saflufenacil |
| B.95 | sulfentrazone |
| B.96 | trifludimoxazin |
| B.97 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyl-oxy]acetate (CAS 353292-31-6) |
| B.98 | benzobicyclon |
| B.99 | bicyclopyrone |
| B.100 | clomazone |
| B.101 | diflufenican |
| B.102 | flurochloridone |
| B.103 | isoxaflutole |
| B.104 | mesotrione |
| B.105 | norflurazone |
| B.106 | picolinafen |
| B.107 | sulcotrione |
| B.108 | tefuryltrione |
| B.109 | tembotrione |
| B.110 | tolpyralate |
| B.111 | topramezone |
| B.112 | topramezone-sodium |
| B.113 | amitrole |
| B.114 | fluometuron |
| B.115 | fenquinotrione |
| B.116 | glyphosate |
| B.117 | glyphosate-ammonium |
| B.118 | glyphosate-dimethylammonium |
| B.119 | glyphosate-isopropylammonium |
| B.120 | glyphosate-trimesium (sulfosate) |
| B.121 | glyphosate-potassium |
| B.122 | glufosinate |
| B.123 | glufosinate-ammonium |
| B.124 | glufosinate-P |
| B.125 | glufosinate-P-ammonium |
| B.126 | pendimethalin |
| B.127 | trifluralin |
| B.128 | acetochlor |
| B.129 | butachlor |
| B.130 | cafenstrole |
| B.131 | dimethenamid-P |
| B.132 | fentrazamide |
| B.133 | flufenacet |
| B.134 | mefenacet |
| B.135 | metazachlor |
| B.136 | metolachlor |
| B.137 | S-metolachlor |
| B.138 | pretilachlor |
| B.139 | fenoxasulfone |
| B.140 | indaziflam |
| B.141 | isoxaben |
| B.142 | triaziflam |
| B.143 | ipfencarbazone |
| B.144 | pyroxasulfone |
| B.145 | 2,4-D |
| B.146 | 2,4-D-isobutyl |
| B.147 | 2,4-D-dimethylammonium |
| B.148 | 2,4-D-N,N-trimethylethanolammonium |
| B.149 | aminopyralid |
| B.150 | aminopyralid-methyl |
| B.151 | aminopyralid-dimethylammonium |
| B.152 | aminopyralid-tris(2-hydroxypropyl)ammonium |
| B.153 | clopyralid |
| B.154 | clopyralid-methyl |
| B.155 | clopyralid-olamine |
| B.156 | dicamba |

TABLE B-continued

| | Herbicide B |
|---|---|
| B.157 | dicamba-butotyl |
| B.158 | dicamba-diglycolamine |
| B.159 | dicamba-dimethylammonium |
| B.160 | dicamba-diolamine |
| B.161 | dicamba-isopropylammonium |
| B.162 | dicamba-potassium |
| B.163 | dicamba-sodium |
| B.164 | dicamba-trolamine |
| B.165 | dicamba-N,N-bis-(3-aminopropyl)methylamine |
| B.166 | dicamba-diethylenetriamine |
| B.167 | fluroxypyr |
| B.168 | fluroxypyr-meptyl |
| B.169 | halauxifen |
| B.170 | halauxifen-methyl |
| B.171 | MCPA |
| B.172 | MCPA-2-ethylhexyl |
| B.173 | MCPA-dimethylammonium |
| B.174 | quinclorac |
| B.175 | quinclorac-dimethylammonium |
| B.176 | quinmerac |
| B.177 | quinmerac-dimethylammonium |
| B.178 | florpyrauxifen |
| B.179 | florpyrauxifen-benzyl (CAS 1390661-72-9) |
| B.180 | aminocyclopyrachlor |
| B.181 | aminocyclopyrachlor-potassium |
| B.182 | aminocyclopyrachlor-methyl |
| B.183 | diflufenzopyr |
| B.184 | diflufenzopyr-sodium |
| B.185 | dymron |
| B.186 | indanofan |
| B.187 | oxaziclomefone |
| B.188 | II.1 |
| B.189 | II.2 |
| B.190 | II.3 |
| B.191 | II.4 |
| B.192 | II.5 |
| B.193 | II.6 |
| B.194 | II.7 |
| B.195 | II.8 |
| B.196 | II.9 |
| B.197 | 4-amino-3-chloro-5-fluoro-6-(7-fluoro-1H-indol-6-yl)picolinic acid (CAS 1629965-65-6) |
| B.198 | flopyrauxifen |
| B.199 | oxotrione (CAS 1486617-21-3) |
| B.200 | cinmethylin |
| B.201 | 2-chloro-3-methylsulfanyl-N-(1-methyltetrazol-5-yl)-4-(trifluoromethyl)benzamide (CAS 1361139-71-0) |
| B.202 | 2-(2,4-dichlorophenyl)methyl-4,4-dimethyl-3-isoxazolidone (CAS 81777-95-9) |
| B.203 | cyclopyranil |

Moreover, it may be useful to apply the compounds of formula (I) in combination with safeners and optionally with one or more further herbicides. Safeners are chemical compounds which prevent or reduce damage on useful plants without having a major impact on the herbicidal action of the compounds of the formula (I) towards unwanted plants. They can be applied either before sowings (e.g. on seed treatments, shoots or seedlings) or in the pre-emergence application or post-emergence application of the useful plant. The safeners and the compounds of formula (I) and optionally the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro [4.5]decane (MON4660, CAS 71526-07-3), 2,2,5-trimethyl-3-(dichloroacetyl)-1,3-oxazoidine (R-29148, CAS 52836-31-4) and N-(2-Methoxybenzoy)-4-[(methylaminocarbonyl) amino]benzenesulfonamide (CAS 129531-12-0).

Particularly preferred safeners C are the following compounds C.1 to C.17 listed in table C.

TABLE C

| C.1 | benoxacor | C.2 | cloquintocet |
|---|---|---|---|
| C.3 | cloquintocet-mexyl | C.4 | cyprosulfamide |
| C.5 | dichlormid | C.6 | fenchlorazole |
| C.7 | fenchlorazole-ethyl | C.8 | fenclorim |
| C.9 | furilazole | C.10 | isoxadifen |
| C.11 | isoxadifen-ethyl | C.12 | mefenpyr |
| C.13 | mefenpyr-diethyl | C.14 | naphtalic acid anhydride |
| C.15 | 4-(dichloroacetyl)-1-oxa-4-azaspiro[4.5]decane | C.16 | 2,2,5-trimethyl-3-(dichloroacetyl)-1,3-oxazolidine |
| C.17 | N-(2-Methoxybenzoyl)-4-[(methylamino-carbonyl)amino]benzene-sulfonamide | C.17 | metcamifen |

The active compounds B of groups b1) to b15) and the safener compounds C are known herbicides and safeners, see, for example, The Compendium of Pesticide Common Names (http:/www.alanwood.net/pesticides); Farm Chemicals Handbook 2000 volume 86, Meister Publishing Company, 2000; B. Hock, C. Fedtke, R. R. Schmidt, Herbizide [Herbicides], Georg Thieme Verag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloro-acetyl)-1,3-oxazolidine [CAS No. 52836-31-4] is also referred to as R-29148. 4-(Dichloroacetyl)-1-oxa-4-azaspiro [4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

The following combinations indicated by the code A-X.Y.Z represent particular embodiments of the invention:
A-1.1.1 to A-1.727.3671,
A-2.1.1 to A-2.727.3671,
A-3.1.1 to A-3.727.3671,
A-4.1.1 to A-4.727.3671,
A-5.1.1 to A-5.727.3671,
A-6.1.1 to A-6.727.3671,
A-7.1.1 to A-7.727.3671,
A-8.1.1 to A-8.727.3671,
A-9.1.1 to A-9.727.3671,
A-10.1.1 to A-10.727.3671,
A-11.1.1 to A-11.727.3671,
A-12.1.1 to A-12.727.3671,
A-13.1.1 to A-13.727.3671,
A-14.1.1 to A-14.727.3671,
A-15.1.1 to A-15.727.3671,
A-16.1.1 to A-16.727.3671, A-17.1.1 to A-17.727.3671,
A-18.1.1 to A-18.727.3671,
A-19.1.1 to A-19.727.3671,
A-20.1.1 to A-20.727.3671,
A-21.1.1 to A-21.727.3671,
A-22.1.1 to A-22.727.3671,
A-23.1.1 to A-23.727.3671,
A-24.1.1 to A-24.727.3671,
A-25.1.1 to A-25.727.3671,
A-26.1.1 to A-26.727.3671,
A-27.1.1 to A-27.727.3671,
A-28.1.1 to A-28.727.3671,
A-29.1.1 to A-29.727.3671,
A-30.1.1 to A-30.727.3671,
A-31.1.1 to A-31.727.3671,
A-32.1.1 to A-32.727.3671,
A-33.1.1 to A-33.727.3671,
A-34.1.1 to A-34.727.3671,
A-35.1.1 to A-35.727.3671.

In the above codes A-X refers to the numbers of tables A-1 to A.35. The integer Y refers to the row of table A, while the integer Z refers to the row of table 1 below.

Hence, the code A-1.1.1 refers to the combination of the compound of formula I.a of table A-1, wherein X and $R^2$ are as defined in row 1 of table A, with the combination of the herbicide B and the safener C are as defined in combination no. 1.1 of table 1.

The code A-12.2.35 refers to the combination of the compound of formula I.a of table A-12, wherein X and $R^2$ are as defined in row 2 of table A, with the combination of the herbicide B and the safener C are as defined in combination no. 1.35 of table 1.

The code A-35.300. 3671 refers to the combination of the compound of formula I.a of table A-35, wherein X and $R^2$ are as defined in row 300 of table A, with the combination of the herbicide B and the safener C are as defined in combination no. 1.3456 of table 1.

TABLE 1

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |

TABLE 1-continued

| comp. no. | herbicide B | safener C |
|---|---|---|
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |

TABLE 1-continued

| comp. no. | herbicide B | safener C |
|---|---|---|
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.145 | — |
| 1.146 | B.146 | — |
| 1.147 | B.147 | — |
| 1.148 | B.148 | — |
| 1.149 | B.149 | — |
| 1.150 | B.150 | — |
| 1.151 | B.151 | — |
| 1.152 | B.152 | — |
| 1.153 | B.153 | — |
| 1.154 | B.154 | — |
| 1.155 | B.155 | — |
| 1.156 | B.156 | — |
| 1.157 | B.157 | — |
| 1.158 | B.158 | — |
| 1.159 | B.159 | — |
| 1.160 | B.160 | — |
| 1.161 | B.161 | — |
| 1.162 | B.162 | — |
| 1.163 | B.163 | — |
| 1.164 | B.164 | — |
| 1.165 | B.165 | — |
| 1.166 | B.166 | — |
| 1.167 | B.167 | — |
| 1.168 | B.168 | — |
| 1.169 | B.169 | — |
| 1.170 | B.170 | — |
| 1.171 | B.171 | — |
| 1.172 | B.172 | — |
| 1.173 | B.173 | — |
| 1.174 | B.174 | — |
| 1.175 | B.175 | — |
| 1.176 | B.176 | — |
| 1.177 | B.177 | — |
| 1.178 | B.178 | — |
| 1.179 | B.179 | — |
| 1.180 | B.180 | — |
| 1.181 | B.181 | — |
| 1.182 | B.182 | — |
| 1.183 | B.183 | — |
| 1.184 | B.184 | — |
| 1.185 | B.185 | — |
| 1.186 | B.186 | — |
| 1.187 | B.187 | — |
| 1.188 | B.188 | — |
| 1.189 | B.189 | — |
| 1.190 | B.190 | — |
| 1.191 | B.191 | — |
| 1.192 | B.192 | — |
| 1.193 | B.193 | — |
| 1.194 | B.194 | — |
| 1.195 | B.195 | — |
| 1.196 | B.196 | — |
| 1.197 | B.197 | — |
| 1.198 | B.198 | — |
| 1.199 | B.199 | — |
| 1.200 | B.200 | — |
| 1.201 | B.201 | — |
| 1.202 | B.202 | — |
| 1.203 | B.203 | — |
| 1.204 | B.1 | C.1 |
| 1.205 | B.2 | C.1 |
| 1.206 | B.3 | C.1 |
| 1.207 | B.4 | C.1 |
| 1.208 | B.5 | C.1 |
| 1.209 | B.6 | C.1 |
| 1.210 | B.7 | C.1 |
| 1.211 | B.8 | C.1 |
| 1.212 | B.9 | C.1 |
| 1.213 | B.10 | C.1 |
| 1.214 | B.11 | C.1 |
| 1.215 | B.12 | C.1 |
| 1.216 | B.13 | C.1 |
| 1.217 | B.14 | C.1 |
| 1.218 | B.15 | C.1 |
| 1.219 | B.16 | C.1 |
| 1.220 | B.17 | C.1 |
| 1.221 | B.18 | C.1 |
| 1.222 | B.19 | C.1 |
| 1.223 | B.20 | C.1 |
| 1.224 | B.21 | C.1 |
| 1.225 | B.22 | C.1 |
| 1.226 | B.23 | C.1 |
| 1.227 | B.24 | C.1 |
| 1.228 | B.25 | C.1 |
| 1.229 | B.26 | C.1 |
| 1.230 | B.27 | C.1 |
| 1.231 | B.28 | C.1 |
| 1.232 | B.29 | C.1 |
| 1.233 | B.30 | C.1 |
| 1.234 | B.31 | C.1 |
| 1.235 | B.32 | C.1 |
| 1.236 | B.33 | C.1 |
| 1.237 | B.34 | C.1 |
| 1.238 | B.35 | C.1 |
| 1.239 | B.36 | C.1 |
| 1.240 | B.37 | C.1 |
| 1.241 | B.38 | C.1 |
| 1.242 | B.39 | C.1 |
| 1.243 | B.40 | C.1 |
| 1.244 | B.41 | C.1 |
| 1.245 | B.42 | C.1 |
| 1.246 | B.43 | C.1 |
| 1.247 | B.44 | C.1 |
| 1.248 | B.45 | C.1 |
| 1.249 | B.46 | C.1 |
| 1.250 | B.47 | C.1 |
| 1.251 | B.48 | C.1 |
| 1.252 | B.49 | C.1 |
| 1.253 | B.50 | C.1 |
| 1.254 | B.51 | C.1 |
| 1.255 | B.52 | C.1 |
| 1.256 | B.53 | C.1 |
| 1.257 | B.54 | C.1 |
| 1.258 | B.55 | C.1 |
| 1.259 | B.56 | C.1 |
| 1.260 | B.57 | C.1 |
| 1.261 | B.58. | C.1 |
| 1.262 | B.59 | C.1 |
| 1.263 | B.60 | C.1 |
| 1.264 | B.61 | C.1 |

TABLE 1-continued

| comp. no. | herbicide B | safener C |
|---|---|---|
| 1.265 | B.62 | C.1 |
| 1.266 | B.63 | C.1 |
| 1.267 | B.64 | C.1 |
| 1.268 | B.65 | C.1 |
| 1.269 | B.66 | C.1 |
| 1.270 | B.67 | C.1 |
| 1.271 | B.68 | C.1 |
| 1.272 | B.69 | C.1 |
| 1.273 | B.70 | C.1 |
| 1.274 | B.71 | C.1 |
| 1.275 | B.72 | C.1 |
| 1.276 | B.73 | C.1 |
| 1.277 | B.74 | C.1 |
| 1.278 | B.75 | C.1 |
| 1.279 | B.76 | C.1 |
| 1.280 | B.77 | C.1 |
| 1.281 | B.78 | C.1 |
| 1.282 | B.79 | C.1 |
| 1.283 | B.80 | C.1 |
| 1.284 | B.81 | C.1 |
| 1.285 | B.82 | C.1 |
| 1.286 | B.83 | C.1 |
| 1.287 | B.84 | C.1 |
| 1.288 | B.85 | C.1 |
| 1.289 | B.86 | C.1 |
| 1.290 | B.87 | C.1 |
| 1.291 | B.88 | C.1 |
| 1.292 | B.89 | C.1 |
| 1.293 | B.90 | C.1 |
| 1.294 | B.91 | C.1 |
| 1.295 | B.92 | C.1 |
| 1.296 | B.93 | C.1 |
| 1.297 | B.94 | C.1 |
| 1.298 | B.95 | C.1 |
| 1.299 | B.96 | C.1 |
| 1.300 | B.97 | C.1 |
| 1.301 | B.98 | C.1 |
| 1.302 | B.99 | C.1 |
| 1.303 | B.100 | C.1 |
| 1.304 | B.101 | C.1 |
| 1.305 | B.102 | C.1 |
| 1.306 | B.103 | C.1 |
| 1.307 | B.104 | C.1 |
| 1.308 | B.105 | C.1 |
| 1.309 | B.106 | C.1 |
| 1.310 | B.107 | C.1 |
| 1.311 | B.108 | C.1 |
| 1.312 | B.109 | C.1 |
| 1.313 | B.110 | C.1 |
| 1.314 | B.111 | C.1 |
| 1.315 | B.112 | C.1 |
| 1.316 | B.113 | C.1 |
| 1.317 | B.114 | C.1 |
| 1.318 | B.115 | C.1 |
| 1.319 | B.116 | C.1 |
| 1.320 | B.117 | C.1 |
| 1.321 | B.118 | C.1 |
| 1.322 | B.119 | C.1 |
| 1.323 | B.120 | C.1 |
| 1.324 | B.121 | C.1 |
| 1.325 | B.122 | C.1 |
| 1.326 | B.123 | C.1 |
| 1.327 | B.124 | C.1 |
| 1.328 | B.125 | C.1 |
| 1.329 | B.126 | C.1 |
| 1.330 | B.127 | C.1 |
| 1.331 | B.128 | C.1 |
| 1.332 | B.129 | C.1 |
| 1.333 | B.130 | C.1 |
| 1.334 | B.131 | C.1 |
| 1.335 | B.132 | C.1 |
| 1.336 | B.133 | C.1 |
| 1.337 | B.134 | C.1 |
| 1.338 | B.135 | C.1 |
| 1.339 | B.136 | C.1 |
| 1.340 | B.137 | C.1 |
| 1.341 | B.138 | C.1 |
| 1.342 | B.139 | C.1 |
| 1.343 | B.140 | C.1 |
| 1.344 | B.141 | C.1 |
| 1.345 | B.142 | C.1 |
| 1.346 | B.143 | C.1 |
| 1.347 | B.144 | C.1 |
| 1.348 | B.145 | C.1 |
| 1.349 | B.146 | C.1 |
| 1.350 | B.147 | C.1 |
| 1.351 | B.148 | C.1 |
| 1.352 | B.149 | C.1 |
| 1.353 | B.150 | C.1 |
| 1.354 | B.151 | C.1 |
| 1.355 | B.152 | C.1 |
| 1.356 | B.153 | C.1 |
| 1.357 | B.154 | C.1 |
| 1.358 | B.155 | C.1 |
| 1.359 | B.156 | C.1 |
| 1.360 | B.157 | C.1 |
| 1.361 | B.158 | C.1 |
| 1.362 | B.159 | C.1 |
| 1.363 | B.160 | C.1 |
| 1.364 | B.161 | C.1 |
| 1.365 | B.162 | C.1 |
| 1.366 | B.163 | C.1 |
| 1.367 | B.164 | C.1 |
| 1.368 | B.165 | C.1 |
| 1.369 | B.166 | C.1 |
| 1.370 | B.167 | C.1 |
| 1.371 | B.168 | C.1 |
| 1.372 | B.169 | C.1 |
| 1.373 | B.170 | C.1 |
| 1.374 | B.171 | C.1 |
| 1.375 | B.172 | C.1 |
| 1.376 | B.173 | C.1 |
| 1.377 | B.174 | C.1 |
| 1.378 | B.175 | C.1 |
| 1.379 | B.176 | C.1 |
| 1.380 | B.177 | C.1 |
| 1.381 | B.178 | C.1 |
| 1.382 | B.179 | C.1 |
| 1.383 | B.180 | C.1 |
| 1.384 | B.181 | C.1 |
| 1.385 | B.182 | C.1 |
| 1.386 | B.183 | C.1 |
| 1.387 | B.184 | C.1 |
| 1.388 | B.185 | C.1 |
| 1.389 | B.186 | C.1 |
| 1.390 | B.187 | C.1 |
| 1.391 | B.188 | C.1 |
| 1.392 | B.189 | C.1 |
| 1.393 | B.190 | C.1 |
| 1.394 | B.191 | C.1 |
| 1.395 | B.192 | C.1 |
| 1.396 | B.193 | C.1 |
| 1.397 | B.194 | C.1 |
| 1.398 | B.195 | C.1 |
| 1.399 | B.196 | C.1 |
| 1.400 | B.197 | C.1 |
| 1.401 | B.198 | C.1 |
| 1.402 | B.199 | C.1 |
| 1.403 | B.200 | C.1 |
| 1.404 | B.201 | C.1 |
| 1.405 | B.202 | C.1 |
| 1.406 | B.203 | C.1 |
| 1.407 | B.1 | C.2 |
| 1.408 | B.2 | C.2 |
| 1.409 | B.3 | C.2 |
| 1.410 | B.4 | C.2 |
| 1.411 | B.5 | C.2 |
| 1.412 | B.6 | C.2 |
| 1.413 | B.7 | C.2 |
| 1.414 | B.8 | C.2 |
| 1.415 | B.9 | C.2 |
| 1.416 | B.10 | C.2 |
| 1.417 | B.11 | C.2 |
| 1.418 | B.12 | C.2 |
| 1.419 | B.13 | C.2 |
| 1.420 | B.14 | C.2 |

TABLE 1-continued

| comp. no. | herbicide B | safener C |
|---|---|---|
| 1.421 | B.15 | C.2 |
| 1.422 | B.16 | C.2 |
| 1.423 | B.17 | C.2 |
| 1.424 | B.18 | C.2 |
| 1.425 | B.19 | C.2 |
| 1.426 | B.20 | C.2 |
| 1.427 | B.21 | C.2 |
| 1.428 | B.22 | C.2 |
| 1.429 | B.23 | C.2 |
| 1.430 | B.24 | C.2 |
| 1.431 | B.25 | C.2 |
| 1.432 | B.26 | C.2 |
| 1.433 | B.27 | C.2 |
| 1.434 | B.28 | C.2 |
| 1.435 | B.29 | C.2 |
| 1.436 | B.30 | C.2 |
| 1.437 | B.31 | C.2 |
| 1.438 | B.32 | C.2 |
| 1.439 | B.33 | C.2 |
| 1.440 | B.34 | C.2 |
| 1.441 | B.35 | C.2 |
| 1.442 | B.36 | C.2 |
| 1.443 | B.37 | C.2 |
| 1.444 | B.38 | C.2 |
| 1.445 | B.39 | C.2 |
| 1.446 | B.40 | C.2 |
| 1.447 | B.41 | C.2 |
| 1.448 | B.42 | C.2 |
| 1.449 | B.43 | C.2 |
| 1.450 | B.44 | C.2 |
| 1.451 | B.45 | C.2 |
| 1.452 | B.46 | C.2 |
| 1.453 | B.47 | C.2 |
| 1.454 | B.48 | C.2 |
| 1.455 | B.49 | C.2 |
| 1.456 | B.50 | C.2 |
| 1.457 | B.51 | C.2 |
| 1.458 | B.52 | C.2 |
| 1.459 | B.53 | C.2 |
| 1.460 | B.54 | C.2 |
| 1.461 | B.55 | C.2 |
| 1.462 | B.56 | C.2 |
| 1.463 | B.57 | C.2 |
| 1.464 | B.58. | C.2 |
| 1.465 | B.59 | C.2 |
| 1.466 | B.60 | C.2 |
| 1.467 | B.61 | C.2 |
| 1.468 | B.62 | C.2 |
| 1.469 | B.63 | C.2 |
| 1.470 | B.64 | C.2 |
| 1.471 | B.65 | C.2 |
| 1.472 | B.66 | C.2 |
| 1.473 | B.67 | C.2 |
| 1.474 | B.68 | C.2 |
| 1.475 | B.69 | C.2 |
| 1.476 | B.70 | C.2 |
| 1.477 | B.71 | C.2 |
| 1.478 | B.72 | C.2 |
| 1.479 | B.73 | C.2 |
| 1.480 | B.74 | C.2 |
| 1.481 | B.75 | C.2 |
| 1.482 | B.76 | C.2 |
| 1.483 | B.77 | C.2 |
| 1.484 | B.78 | C.2 |
| 1.485 | B.79 | C.2 |
| 1.486 | B.80 | C.2 |
| 1.487 | B.81 | C.2 |
| 1.488 | B.82 | C.2 |
| 1.489 | B.83 | C.2 |
| 1.490 | B.84 | C.2 |
| 1.491 | B.85 | C.2 |
| 1.492 | B.86 | C.2 |
| 1.493 | B.87 | C.2 |
| 1.494 | B.88 | C.2 |
| 1.495 | B.89 | C.2 |
| 1.496 | B.90 | C.2 |
| 1.497 | B.91 | C.2 |
| 1.498 | B.92 | C.2 |
| 1.499 | B.93 | C.2 |
| 1.500 | B.94 | C.2 |
| 1.501 | B.95 | C.2 |
| 1.502 | B.96 | C.2 |
| 1.503 | B.97 | C.2 |
| 1.504 | B.98 | C.2 |
| 1.505 | B.99 | C.2 |
| 1.506 | B.100 | C.2 |
| 1.507 | B.101 | C.2 |
| 1.508 | B.102 | C.2 |
| 1.509 | B.103 | C.2 |
| 1.510 | B.104 | C.2 |
| 1.511 | B.105 | C.2 |
| 1.512 | B.106 | C.2 |
| 1.513 | B.107 | C.2 |
| 1.514 | B.108 | C.2 |
| 1.515 | B.109 | C.2 |
| 1.516 | B.110 | C.2 |
| 1.517 | B.111 | C.2 |
| 1.518 | B.112 | C.2 |
| 1.519 | B.113 | C.2 |
| 1.520 | B.114 | C.2 |
| 1.521 | B.115 | C.2 |
| 1.522 | B.116 | C.2 |
| 1.523 | B.117 | C.2 |
| 1.524 | B.118 | C.2 |
| 1.525 | B.119 | C.2 |
| 1.526 | B.120 | C.2 |
| 1.527 | B.121 | C.2 |
| 1.528 | B.122 | C.2 |
| 1.529 | B.123 | C.2 |
| 1.530 | B.124 | C.2 |
| 1.531 | B.125 | C.2 |
| 1.532 | B.126 | C.2 |
| 1.533 | B.127 | C.2 |
| 1.534 | B.128 | C.2 |
| 1.535 | B.129 | C.2 |
| 1.536 | B.130 | C.2 |
| 1.537 | B.131 | C.2 |
| 1.538 | B.132 | C.2 |
| 1.539 | B.133 | C.2 |
| 1.540 | B.134 | C.2 |
| 1.541 | B.135 | C.2 |
| 1.542 | B.136 | C.2 |
| 1.543 | B.137 | C.2 |
| 1.544 | B.138 | C.2 |
| 1.545 | B.139 | C.2 |
| 1.546 | B.140 | C.2 |
| 1.547 | B.141 | C.2 |
| 1.548 | B.142 | C.2 |
| 1.549 | B.143 | C.2 |
| 1.550 | B.144 | C.2 |
| 1.551 | B.145 | C.2 |
| 1.552 | B.146 | C.2 |
| 1.553 | B.147 | C.2 |
| 1.554 | B.148 | C.2 |
| 1.555 | B.149 | C.2 |
| 1.556 | B.150 | C.2 |
| 1.557 | B.151 | C.2 |
| 1.558 | B.152 | C.2 |
| 1.559 | B.153 | C.2 |
| 1.560 | B.154 | C.2 |
| 1.561 | B.155 | C.2 |
| 1.562 | B.156 | C.2 |
| 1.563 | B.157 | C.2 |
| 1.564 | B.158 | C.2 |
| 1.565 | B.159 | C.2 |
| 1.566 | B.160 | C.2 |
| 1.567 | B.161 | C.2 |
| 1.568 | B.162 | C.2 |
| 1.569 | B.163 | C.2 |
| 1.570 | B.164 | C.2 |
| 1.571 | B.165 | C.2 |
| 1.572 | B.166 | C.2 |
| 1.573 | B.167 | C.2 |
| 1.574 | B.168 | C.2 |
| 1.575 | B.169 | C.2 |
| 1.576 | B.170 | C.2 |

TABLE 1-continued

| comp. no. | herbicide B | safener C |
|---|---|---|
| 1.577 | B.171 | C.2 |
| 1.578 | B.172 | C.2 |
| 1.579 | B.173 | C.2 |
| 1.580 | B.174 | C.2 |
| 1.581 | B.175 | C.2 |
| 1.582 | B.176 | C.2 |
| 1.583 | B.177 | C.2 |
| 1.584 | B.178 | C.2 |
| 1.585 | B.179 | C.2 |
| 1.586 | B.180 | C.2 |
| 1.587 | B.181 | C.2 |
| 1.588 | B.182 | C.2 |
| 1.589 | B.183 | C.2 |
| 1.590 | B.184 | C.2 |
| 1.591 | B.185 | C.2 |
| 1.592 | B.186 | C.2 |
| 1.593 | B.187 | C.2 |
| 1.594 | B.188 | C.2 |
| 1.595 | B.189 | C.2 |
| 1.596 | B.190 | C.2 |
| 1.597 | B.191 | C.2 |
| 1.598 | B.192 | C.2 |
| 1.599 | B.193 | C.2 |
| 1.600 | B.194 | C.2 |
| 1.601 | B.195 | C.2 |
| 1.602 | B.196 | C.2 |
| 1.603 | B.197 | C.2 |
| 1.604 | B.198 | C.2 |
| 1.605 | B.199 | C.2 |
| 1.606 | B.200 | C.2 |
| 1.607 | B.201 | C.2 |
| 1.608 | B.202 | C.2 |
| 1.609 | B.203 | C.2 |
| 1.610 | B.1 | C.3 |
| 1.611 | B.2 | C.3 |
| 1.612 | B.3 | C.3 |
| 1.613 | B.4 | C.3 |
| 1.614 | B.5 | C.3 |
| 1.615 | B.6 | C.3 |
| 1.616 | B.7 | C.3 |
| 1.617 | B.8 | C.3 |
| 1.618 | B.9 | C.3 |
| 1.619 | B.10 | C.3 |
| 1.620 | B.11 | C.3 |
| 1.621 | B.12 | C.3 |
| 1.622 | B.13 | C.3 |
| 1.623 | B.14 | C.3 |
| 1.624 | B.15 | C.3 |
| 1.625 | B.16 | C.3 |
| 1.626 | B.17 | C.3 |
| 1.627 | B.18 | C.3 |
| 1.628 | B.19 | C.3 |
| 1.629 | B.20 | C.3 |
| 1.630 | B.21 | C.3 |
| 1.631 | B.22 | C.3 |
| 1.632 | B.23 | C.3 |
| 1.633 | B.24 | C.3 |
| 1.634 | B.25 | C.3 |
| 1.635 | B.26 | C.3 |
| 1.636 | B.27 | C.3 |
| 1.637 | B.28 | C.3 |
| 1.638 | B.29 | C.3 |
| 1.639 | B.30 | C.3 |
| 1.640 | B.31 | C.3 |
| 1.641 | B.32 | C.3 |
| 1.642 | B.33 | C.3 |
| 1.643 | B.34 | C.3 |
| 1.644 | B.35 | C.3 |
| 1.645 | B.36 | C.3 |
| 1.646 | B.37 | C.3 |
| 1.647 | B.38 | C.3 |
| 1.648 | B.39 | C.3 |
| 1.649 | B.40 | C.3 |
| 1.650 | B.41 | C.3 |
| 1.651 | B.42 | C.3 |
| 1.652 | B.43 | C.3 |
| 1.653 | B.44 | C.3 |
| 1.654 | B.45 | C.3 |
| 1.655 | B.46 | C.3 |
| 1.656 | B.47 | C.3 |
| 1.657 | B.48 | C.3 |
| 1.658 | B.49 | C.3 |
| 1.659 | B.50 | C.3 |
| 1.660 | B.51 | C.3 |
| 1.661 | B.52 | C.3 |
| 1.662 | B.53 | C.3 |
| 1.663 | B.54 | C.3 |
| 1.664 | B.55 | C.3 |
| 1.665 | B.56 | C.3 |
| 1.666 | B.57 | C.3 |
| 1.667 | B.58. | C.3 |
| 1.668 | B.59 | C.3 |
| 1.669 | B.60 | C.3 |
| 1.670 | B.61 | C.3 |
| 1.671 | B.62 | C.3 |
| 1.672 | B.63 | C.3 |
| 1.673 | B.64 | C.3 |
| 1.674 | B.65 | C.3 |
| 1.675 | B.66 | C.3 |
| 1.676 | B.67 | C.3 |
| 1.677 | B.68 | C.3 |
| 1.678 | B.69 | C.3 |
| 1.679 | B.70 | C.3 |
| 1.680 | B.71 | C.3 |
| 1.681 | B.72 | C.3 |
| 1.682 | B.73 | C.3 |
| 1.683 | B.74 | C.3 |
| 1.684 | B.75 | C.3 |
| 1.685 | B.76 | C.3 |
| 1.686 | B.77 | C.3 |
| 1.687 | B.78 | C.3 |
| 1.688 | B.79 | C.3 |
| 1.689 | B.80 | C.3 |
| 1.690 | B.81 | C.3 |
| 1.691 | B.82 | C.3 |
| 1.692 | B.83 | C.3 |
| 1.693 | B.84 | C.3 |
| 1.694 | B.85 | C.3 |
| 1.695 | B.86 | C.3 |
| 1.696 | B.87 | C.3 |
| 1.697 | B.88 | C.3 |
| 1.698 | B.89 | C.3 |
| 1.699 | B.90 | C.3 |
| 1.700 | B.91 | C.3 |
| 1.701 | B.92 | C.3 |
| 1.702 | B.93 | C.3 |
| 1.703 | B.94 | C.3 |
| 1.704 | B.95 | C.3 |
| 1.705 | B.96 | C.3 |
| 1.706 | B.97 | C.3 |
| 1.707 | B.98 | C.3 |
| 1.708 | B.99 | C.3 |
| 1.709 | B.100 | C.3 |
| 1.710 | B.101 | C.3 |
| 1.711 | B.102 | C.3 |
| 1.712 | B.103 | C.3 |
| 1.713 | B.104 | C.3 |
| 1.714 | B.105 | C.3 |
| 1.715 | B.106 | C.3 |
| 1.716 | B.107 | C.3 |
| 1.717 | B.108 | C.3 |
| 1.718 | B.109 | C.3 |
| 1.719 | B.110 | C.3 |
| 1.720 | B.111 | C.3 |
| 1.721 | B.112 | C.3 |
| 1.722 | B.113 | C.3 |
| 1.723 | B.114 | C.3 |
| 1.724 | B.115 | C.3 |
| 1.725 | B.116 | C.3 |
| 1.726 | B.117 | C.3 |
| 1.727 | B.118 | C.3 |
| 1.728 | B.119 | C.3 |
| 1.729 | B.120 | C.3 |
| 1.730 | B.121 | C.3 |
| 1.731 | B.122 | C.3 |
| 1.732 | B.123 | C.3 |

TABLE 1-continued

| comp. no. | herbicide B | safener C |
|---|---|---|
| 1.733 | B.124 | C.3 |
| 1.734 | B.125 | C.3 |
| 1.735 | B.126 | C.3 |
| 1.736 | B.127 | C.3 |
| 1.737 | B.128 | C.3 |
| 1.738 | B.129 | C.3 |
| 1.739 | B.130 | C.3 |
| 1.740 | B.131 | C.3 |
| 1.741 | B.132 | C.3 |
| 1.742 | B.133 | C.3 |
| 1.743 | B.134 | C.3 |
| 1.744 | B.135 | C.3 |
| 1.745 | B.136 | C.3 |
| 1.746 | B.137 | C.3 |
| 1.747 | B.138 | C.3 |
| 1.748 | B.139 | C.3 |
| 1.749 | B.140 | C.3 |
| 1.750 | B.141 | C.3 |
| 1.751 | B.142 | C.3 |
| 1.752 | B.143 | C.3 |
| 1.753 | B.144 | C.3 |
| 1.754 | B.145 | C.3 |
| 1.755 | B.146 | C.3 |
| 1.756 | B.147 | C.3 |
| 1.757 | B.148 | C.3 |
| 1.758 | B.149 | C.3 |
| 1.759 | B.150 | C.3 |
| 1.760 | B.151 | C.3 |
| 1.761 | B.152 | C.3 |
| 1.762 | B.153 | C.3 |
| 1.763 | B.154 | C.3 |
| 1.764 | B.155 | C.3 |
| 1.765 | B.156 | C.3 |
| 1.766 | B.157 | C.3 |
| 1.767 | B.158 | C.3 |
| 1.768 | B.159 | C.3 |
| 1.769 | B.160 | C.3 |
| 1.770 | B.161 | C.3 |
| 1.771 | B.162 | C.3 |
| 1.772 | B.163 | C.3 |
| 1.773 | B.164 | C.3 |
| 1.774 | B.165 | C.3 |
| 1.775 | B.166 | C.3 |
| 1.776 | B.167 | C.3 |
| 1.777 | B.168 | C.3 |
| 1.778 | B.169 | C.3 |
| 1.779 | B.170 | C.3 |
| 1.780 | B.171 | C.3 |
| 1.781 | B.172 | C.3 |
| 1.782 | B.173 | C.3 |
| 1.783 | B.174 | C.3 |
| 1.784 | B.175 | C.3 |
| 1.785 | B.176 | C.3 |
| 1.786 | B.177 | C.3 |
| 1.787 | B.178 | C.3 |
| 1.788 | B.179 | C.3 |
| 1.789 | B.180 | C.3 |
| 1.790 | B.181 | C.3 |
| 1.791 | B.182 | C.3 |
| 1.792 | B.183 | C.3 |
| 1.793 | B.184 | C.3 |
| 1.794 | B.185 | C.3 |
| 1.795 | B.186 | C.3 |
| 1.796 | B.187 | C.3 |
| 1.797 | B.188 | C.3 |
| 1.798 | B.189 | C.3 |
| 1.799 | B.190 | C.3 |
| 1.800 | B.191 | C.3 |
| 1.801 | B.192 | C.3 |
| 1.802 | B.193 | C.3 |
| 1.803 | B.194 | C.3 |
| 1.804 | B.195 | C.3 |
| 1.805 | B.196 | C.3 |
| 1.806 | B.197 | C.3 |
| 1.807 | B.198 | C.3 |
| 1.808 | B.199 | C.3 |
| 1.809 | B.200 | C.3 |
| 1.810 | B.201 | C.3 |
| 1.811 | B.202 | C.3 |
| 1.812 | B.203 | C.3 |
| 1.813 | B.1 | C.4 |
| 1.814 | B.2 | C.4 |
| 1.815 | B.3 | C.4 |
| 1.816 | B.4 | C.4 |
| 1.817 | B.5 | C.4 |
| 1.818 | B.6 | C.4 |
| 1.819 | B.7 | C.4 |
| 1.820 | B.8 | C.4 |
| 1.821 | B.9 | C.4 |
| 1.822 | B.10 | C.4 |
| 1.823 | B.11 | C.4 |
| 1.824 | B.12 | C.4 |
| 1.825 | B.13 | C.4 |
| 1.826 | B.14 | C.4 |
| 1.827 | B.15 | C.4 |
| 1.828 | B.16 | C.4 |
| 1.829 | B.17 | C.4 |
| 1.830 | B.18 | C.4 |
| 1.831 | B.19 | C.4 |
| 1.832 | B.20 | C.4 |
| 1.833 | B.21 | C.4 |
| 1.834 | B.22 | C.4 |
| 1.835 | B.23 | C.4 |
| 1.836 | B.24 | C.4 |
| 1.837 | B.25 | C.4 |
| 1.838 | B.26 | C.4 |
| 1.839 | B.27 | C.4 |
| 1.840 | B.28 | C.4 |
| 1.841 | B.29 | C.4 |
| 1.842 | B.30 | C.4 |
| 1.843 | B.31 | C.4 |
| 1.844 | B.32 | C.4 |
| 1.845 | B.33 | C.4 |
| 1.846 | B.34 | C.4 |
| 1.847 | B.35 | C.4 |
| 1.848 | B.36 | C.4 |
| 1.849 | B.37 | C.4 |
| 1.850 | B.38 | C.4 |
| 1.851 | B.39 | C.4 |
| 1.852 | B.40 | C.4 |
| 1.853 | B.41 | C.4 |
| 1.854 | B.42 | C.4 |
| 1.855 | B.43 | C.4 |
| 1.856 | B.44 | C.4 |
| 1.857 | B.45 | C.4 |
| 1.858 | B.46 | C.4 |
| 1.859 | B.47 | C.4 |
| 1.860 | B.48 | C.4 |
| 1.861 | B.49 | C.4 |
| 1.862 | B.50 | C.4 |
| 1.863 | B.51 | C.4 |
| 1.864 | B.52 | C.4 |
| 1.865 | B.53 | C.4 |
| 1.866 | B.54 | C.4 |
| 1.867 | B.55 | C.4 |
| 1.868 | B.56 | C.4 |
| 1.869 | B.57 | C.4 |
| 1.870 | B.58. | C.4 |
| 1.871 | B.59 | C.4 |
| 1.872 | B.60 | C.4 |
| 1.873 | B.61 | C.4 |
| 1.874 | B.62 | C.4 |
| 1.875 | B.63 | C.4 |
| 1.876 | B.64 | C.4 |
| 1.877 | B.65 | C.4 |
| 1.878 | B.66 | C.4 |
| 1.879 | B.67 | C.4 |
| 1.880 | B.68 | C.4 |
| 1.881 | B.69 | C.4 |
| 1.882 | B.70 | C.4 |
| 1.883 | B.71 | C.4 |
| 1.884 | B.72 | C.4 |
| 1.885 | B.73 | C.4 |
| 1.886 | B.74 | C.4 |
| 1.887 | B.75 | C.4 |
| 1.888 | B.76 | C.4 |

TABLE 1-continued

| comp. no. | herbicide B | safener C |
|---|---|---|
| 1.889 | B.77 | C.4 |
| 1.890 | B.78 | C.4 |
| 1.891 | B.79 | C.4 |
| 1.892 | B.80 | C.4 |
| 1.893 | B.81 | C.4 |
| 1.894 | B.82 | C.4 |
| 1.895 | B.83 | C.4 |
| 1.896 | B.84 | C.4 |
| 1.897 | B.85 | C.4 |
| 1.898 | B.86 | C.4 |
| 1.899 | B.87 | C.4 |
| 1.900 | B.88 | C.4 |
| 1.901 | B.89 | C.4 |
| 1.902 | B.90 | C.4 |
| 1.903 | B.91 | C.4 |
| 1.904 | B.92 | C.4 |
| 1.905 | B.93 | C.4 |
| 1.906 | B.94 | C.4 |
| 1.907 | B.95 | C.4 |
| 1.908 | B.96 | C.4 |
| 1.909 | B.97 | C.4 |
| 1.910 | B.98 | C.4 |
| 1.911 | B.99 | C.4 |
| 1.912 | B.100 | C.4 |
| 1.913 | B.101 | C.4 |
| 1.914 | B.102 | C.4 |
| 1.915 | B.103 | C.4 |
| 1.916 | B.104 | C.4 |
| 1.917 | B.105 | C.4 |
| 1.918 | B.106 | C.4 |
| 1.919 | B.107 | C.4 |
| 1.920 | B.108 | C.4 |
| 1.921 | B.109 | C.4 |
| 1.922 | B.110 | C.4 |
| 1.923 | B.111 | C.4 |
| 1.924 | B.112 | C.4 |
| 1.925 | B.113 | C.4 |
| 1.926 | B.114 | C.4 |
| 1.927 | B.115 | C.4 |
| 1.928 | B.116 | C.4 |
| 1.929 | B.117 | C.4 |
| 1.930 | B.118 | C.4 |
| 1.931 | B.119 | C.4 |
| 1.932 | B.120 | C.4 |
| 1.933 | B.121 | C.4 |
| 1.934 | B.122 | C.4 |
| 1.935 | B.123 | C.4 |
| 1.936 | B.124 | C.4 |
| 1.937 | B.125 | C.4 |
| 1.938 | B.126 | C.4 |
| 1.939 | B.127 | C.4 |
| 1.940 | B.128 | C.4 |
| 1.941 | B.129 | C.4 |
| 1.942 | B.130 | C.4 |
| 1.943 | B.131 | C.4 |
| 1.944 | B.132 | C.4 |
| 1.945 | B.133 | C.4 |
| 1.946 | B.134 | C.4 |
| 1.947 | B.135 | C.4 |
| 1.948 | B.136 | C.4 |
| 1.949 | B.137 | C.4 |
| 1.950 | B.138 | C.4 |
| 1.951 | B.139 | C.4 |
| 1.952 | B.140 | C.4 |
| 1.953 | B.141 | C.4 |
| 1.954 | B.142 | C.4 |
| 1.955 | B.143 | C.4 |
| 1.956 | B.144 | C.4 |
| 1.957 | B.145 | C.4 |
| 1.958 | B.146 | C.4 |
| 1.959 | B.147 | C.4 |
| 1.960 | B.148 | C.4 |
| 1.961 | B.149 | C.4 |
| 1.962 | B.150 | C.4 |
| 1.963 | B.151 | C.4 |
| 1.964 | B.152 | C.4 |
| 1.965 | B.153 | C.4 |
| 1.966 | B.154 | C.4 |
| 1.967 | B.155 | C.4 |
| 1.968 | B.156 | C.4 |
| 1.969 | B.157 | C.4 |
| 1.970 | B.158 | C.4 |
| 1.971 | B.159 | C.4 |
| 1.972 | B.160 | C.4 |
| 1.973 | B.161 | C.4 |
| 1.974 | B.162 | C.4 |
| 1.975 | B.163 | C.4 |
| 1.976 | B.164 | C.4 |
| 1.977 | B.165 | C.4 |
| 1.978 | B.166 | C.4 |
| 1.979 | B.167 | C.4 |
| 1.980 | B.168 | C.4 |
| 1.981 | B.169 | C.4 |
| 1.982 | B.170 | C.4 |
| 1.983 | B.171 | C.4 |
| 1.984 | B.172 | C.4 |
| 1.985 | B.173 | C.4 |
| 1.986 | B.174 | C.4 |
| 1.987 | B.175 | C.4 |
| 1.988 | B.176 | C.4 |
| 1.989 | B.177 | C.4 |
| 1.990 | B.178 | C.4 |
| 1.991 | B.179 | C.4 |
| 1.992 | B.180 | C.4 |
| 1.993 | B.181 | C.4 |
| 1.994 | B.182 | C.4 |
| 1.995 | B.183 | C.4 |
| 1.996 | B.184 | C.4 |
| 1.997 | B.185 | C.4 |
| 1.998 | B.186 | C.4 |
| 1.999 | B.187 | C.4 |
| 1.1000 | B.188 | C.4 |
| 1.1001 | B.189 | C.4 |
| 1.1002 | B.190 | C.4 |
| 1.1003 | B.191 | C.4 |
| 1.1004 | B.192 | C.4 |
| 1.1005 | B.193 | C.4 |
| 1.1006 | B.194 | C.4 |
| 1.1007 | B.195 | C.4 |
| 1.1008 | B.196 | C.4 |
| 1.1009 | B.197 | C.4 |
| 1.1010 | B.198 | C.4 |
| 1.1011 | B.199 | C.4 |
| 1.1012 | B.200 | C.4 |
| 1.1013 | B.201 | C.4 |
| 1.1014 | B.202 | C.4 |
| 1.1015 | B.203 | C.4 |
| 1.1016 | B.1 | C.5 |
| 1.1017 | B.2 | C.5 |
| 1.1018 | B.3 | C.5 |
| 1.1019 | B.4 | C.5 |
| 1.1020 | B.5 | C.5 |
| 1.1021 | B.6 | C.5 |
| 1.1022 | B.7 | C.5 |
| 1.1023 | B.8 | C.5 |
| 1.1024 | B.9 | C.5 |
| 1.1025 | B.10 | C.5 |
| 1.1026 | B.11 | C.5 |
| 1.1027 | B.12 | C.5 |
| 1.1028 | B.13 | C.5 |
| 1.1029 | B.14 | C.5 |
| 1.1030 | B.15 | C.5 |
| 1.1031 | B.16 | C.5 |
| 1.1032 | B.17 | C.5 |
| 1.1033 | B.18 | C.5 |
| 1.1034 | B.19 | C.5 |
| 1.1035 | B.20 | C.5 |
| 1.1036 | B.21 | C.5 |
| 1.1037 | B.22 | C.5 |
| 1.1038 | B.23 | C.5 |
| 1.1039 | B.24 | C.5 |
| 1.1040 | B.25 | C.5 |
| 1.1041 | B.26 | C.5 |
| 1.1042 | B.27 | C.5 |
| 1.1043 | B.28 | C.5 |
| 1.1044 | B.29 | C.5 |

TABLE 1-continued

| comp. no. | herbicide B | safener C |
|---|---|---|
| 1.1045 | B.30 | C.5 |
| 1.1046 | B.31 | C.5 |
| 1.1047 | B.32 | C.5 |
| 1.1048 | B.33 | C.5 |
| 1.1049 | B.34 | C.5 |
| 1.1050 | B.35 | C.5 |
| 1.1051 | B.36 | C.5 |
| 1.1052 | B.37 | C.5 |
| 1.1053 | B.38 | C.5 |
| 1.1054 | B.39 | C.5 |
| 1.1055 | B.40 | C.5 |
| 1.1056 | B.41 | C.5 |
| 1.1057 | B.42 | C.5 |
| 1.1058 | B.43 | C.5 |
| 1.1059 | B.44 | C.5 |
| 1.1060 | B.45 | C.5 |
| 1.1061 | B.46 | C.5 |
| 1.1062 | B.47 | C.5 |
| 1.1063 | B.48 | C.5 |
| 1.1064 | B.49 | C.5 |
| 1.1065 | B.50 | C.5 |
| 1.1066 | B.51 | C.5 |
| 1.1067 | B.52 | C.5 |
| 1.1068 | B.53 | C.5 |
| 1.1069 | B.54 | C.5 |
| 1.1070 | B.55 | C.5 |
| 1.1071 | B.56 | C.5 |
| 1.1072 | B.57 | C.5 |
| 1.1073 | B.58. | C.5 |
| 1.1074 | B.59 | C.5 |
| 1.1075 | B.60 | C.5 |
| 1.1076 | B.61 | C.5 |
| 1.1077 | B.62 | C.5 |
| 1.1078 | B.63 | C.5 |
| 1.1079 | B.64 | C.5 |
| 1.1080 | B.65 | C.5 |
| 1.1081 | B.66 | C.5 |
| 1.1082 | B.67 | C.5 |
| 1.1083 | B.68 | C.5 |
| 1.1084 | B.69 | C.5 |
| 1.1085 | B.70 | C.5 |
| 1.1086 | B.71 | C.5 |
| 1.1087 | B.72 | C.5 |
| 1.1088 | B.73 | C.5 |
| 1.1089 | B.74 | C.5 |
| 1.1090 | B.75 | C.5 |
| 1.1091 | B.76 | C.5 |
| 1.1092 | B.77 | C.5 |
| 1.1093 | B.78 | C.5 |
| 1.1094 | B.79 | C.5 |
| 1.1095 | B.80 | C.5 |
| 1.1096 | B.81 | C.5 |
| 1.1097 | B.82 | C.5 |
| 1.1098 | B.83 | C.5 |
| 1.1099 | B.84 | C.5 |
| 1.1100 | B.85 | C.5 |
| 1.1101 | B.86 | C.5 |
| 1.1102 | B.87 | C.5 |
| 1.1103 | B.88 | C.5 |
| 1.1104 | B.89 | C.5 |
| 1.1105 | B.90 | C.5 |
| 1.1106 | B.91 | C.5 |
| 1.1107 | B.92 | C.5 |
| 1.1108 | B.93 | C.5 |
| 1.1109 | B.94 | C.5 |
| 1.1110 | B.95 | C.5 |
| 1.1111 | B.96 | C.5 |
| 1.1112 | B.97 | C.5 |
| 1.1113 | B.98 | C.5 |
| 1.1114 | B.99 | C.5 |
| 1.1115 | B.100 | C.5 |
| 1.1116 | B.101 | C.5 |
| 1.1117 | B.102 | C.5 |
| 1.1118 | B.103 | C.5 |
| 1.1119 | B.104 | C.5 |
| 1.1120 | B.105 | C.5 |
| 1.1121 | B.106 | C.5 |
| 1.1122 | B.107 | C.5 |
| 1.1123 | B.108 | C.5 |
| 1.1124 | B.109 | C.5 |
| 1.1125 | B.110 | C.5 |
| 1.1126 | B.111 | C.5 |
| 1.1127 | B.112 | C.5 |
| 1.1128 | B.113 | C.5 |
| 1.1129 | B.114 | C.5 |
| 1.1130 | B.115 | C.5 |
| 1.1131 | B.116 | C.5 |
| 1.1132 | B.117 | C.5 |
| 1.1133 | B.118 | C.5 |
| 1.1134 | B.119 | C.5 |
| 1.1135 | B.120 | C.5 |
| 1.1136 | B.121 | C.5 |
| 1.1137 | B.122 | C.5 |
| 1.1138 | B.123 | C.5 |
| 1.1139 | B.124 | C.5 |
| 1.1140 | B.125 | C.5 |
| 1.1141 | B.126 | C.5 |
| 1.1142 | B.127 | C.5 |
| 1.1143 | B.128 | C.5 |
| 1.1144 | B.129 | C.5 |
| 1.1145 | B.130 | C.5 |
| 1.1146 | B.131 | C.5 |
| 1.1147 | B.132 | C.5 |
| 1.1148 | B.133 | C.5 |
| 1.1149 | B.134 | C.5 |
| 1.1150 | B.135 | C.5 |
| 1.1151 | B.136 | C.5 |
| 1.1152 | B.137 | C.5 |
| 1.1153 | B.138 | C.5 |
| 1.1154 | B.139 | C.5 |
| 1.1155 | B.140 | C.5 |
| 1.1156 | B.141 | C.5 |
| 1.1157 | B.142 | C.5 |
| 1.1158 | B.143 | C.5 |
| 1.1159 | B.144 | C.5 |
| 1.1160 | B.145 | C.5 |
| 1.1161 | B.146 | C.5 |
| 1.1162 | B.147 | C.5 |
| 1.1163 | B.148 | C.5 |
| 1.1164 | B.149 | C.5 |
| 1.1165 | B.150 | C.5 |
| 1.1166 | B.151 | C.5 |
| 1.1167 | B.152 | C.5 |
| 1.1168 | B.153 | C.5 |
| 1.1169 | B.154 | C.5 |
| 1.1170 | B.155 | C.5 |
| 1.1171 | B.156 | C.5 |
| 1.1172 | B.157 | C.5 |
| 1.1173 | B.158 | C.5 |
| 1.1174 | B.159 | C.5 |
| 1.1175 | B.160 | C.5 |
| 1.1176 | B.161 | C.5 |
| 1.1177 | B.162 | C.5 |
| 1.1178 | B.163 | C.5 |
| 1.1179 | B.164 | C.5 |
| 1.1180 | B.165 | C.5 |
| 1.1181 | B.166 | C.5 |
| 1.1182 | B.167 | C.5 |
| 1.1183 | B.168 | C.5 |
| 1.1184 | B.169 | C.5 |
| 1.1185 | B.170 | C.5 |
| 1.1186 | B.171 | C.5 |
| 1.1187 | B.172 | C.5 |
| 1.1188 | B.173 | C.5 |
| 1.1189 | B.174 | C.5 |
| 1.1190 | B.175 | C.5 |
| 1.1191 | B.176 | C.5 |
| 1.1192 | B.177 | C.5 |
| 1.1193 | B.178 | C.5 |
| 1.1194 | B.179 | C.5 |
| 1.1195 | B.180 | C.5 |
| 1.1196 | B.181 | C.5 |
| 1.1197 | B.182 | C.5 |
| 1.1198 | B.183 | C.5 |
| 1.1199 | B.184 | C.5 |
| 1.1200 | B.185 | C.5 |

TABLE 1-continued

| comp. no. | herbicide B | safener C |
|---|---|---|
| 1.1201 | B.186 | C.5 |
| 1.1202 | B.187 | C.5 |
| 1.1203 | B.188 | C.5 |
| 1.1204 | B.189 | C.5 |
| 1.1205 | B.190 | C.5 |
| 1.1206 | B.191 | C.5 |
| 1.1207 | B.192 | C.5 |
| 1.1208 | B.193 | C.5 |
| 1.1209 | B.194 | C.5 |
| 1.1210 | B.195 | C.5 |
| 1.1211 | B.196 | C.5 |
| 1.1212 | B.197 | C.5 |
| 1.1213 | B.198 | C.5 |
| 1.1214 | B.199 | C.5 |
| 1.1215 | B.200 | C.5 |
| 1.1216 | B.201 | C.5 |
| 1.1217 | B.202 | C.5 |
| 1.1218 | B.203 | C.5 |
| 1.1219 | B.1 | C.6 |
| 1.1220 | B.2 | C.6 |
| 1.1221 | B.3 | C.6 |
| 1.1222 | B.4 | C.6 |
| 1.1223 | B.5 | C.6 |
| 1.1224 | B.6 | C.6 |
| 1.1225 | B.7 | C.6 |
| 1.1226 | B.8 | C.6 |
| 1.1227 | B.9 | C.6 |
| 1.1228 | B.10 | C.6 |
| 1.1229 | B.11 | C.6 |
| 1.1230 | B.12 | C.6 |
| 1.1231 | B.13 | C.6 |
| 1.1232 | B.14 | C.6 |
| 1.1233 | B.15 | C.6 |
| 1.1234 | B.16 | C.6 |
| 1.1235 | B.17 | C.6 |
| 1.1236 | B.18 | C.6 |
| 1.1237 | B.19 | C.6 |
| 1.1238 | B.20 | C.6 |
| 1.1239 | B.21 | C.6 |
| 1.1240 | B.22 | C.6 |
| 1.1241 | B.23 | C.6 |
| 1.1242 | B.24 | C.6 |
| 1.1243 | B.25 | C.6 |
| 1.1244 | B.26 | C.6 |
| 1.1245 | B.27 | C.6 |
| 1.1246 | B.28 | C.6 |
| 1.1247 | B.29 | C.6 |
| 1.1248 | B.30 | C.6 |
| 1.1249 | B.31 | C.6 |
| 1.1250 | B.32 | C.6 |
| 1.1251 | B.33 | C.6 |
| 1.1252 | B.34 | C.6 |
| 1.1253 | B.35 | C.6 |
| 1.1254 | B.36 | C.6 |
| 1.1255 | B.37 | C.6 |
| 1.1256 | B.38 | C.6 |
| 1.1257 | B.39 | C.6 |
| 1.1258 | B.40 | C.6 |
| 1.1259 | B.41 | C.6 |
| 1.1260 | B.42 | C.6 |
| 1.1261 | B.43 | C.6 |
| 1.1262 | B.44 | C.6 |
| 1.1263 | B.45 | C.6 |
| 1.1264 | B.46 | C.6 |
| 1.1265 | B.47 | C.6 |
| 1.1266 | B.48 | C.6 |
| 1.1267 | B.49 | C.6 |
| 1.1268 | B.50 | C.6 |
| 1.1269 | B.51 | C.6 |
| 1.1270 | B.52 | C.6 |
| 1.1271 | B.53 | C.6 |
| 1.1272 | B.54 | C.6 |
| 1.1273 | B.55 | C.6 |
| 1.1274 | B.56 | C.6 |
| 1.1275 | B.57 | C.6 |
| 1.1276 | B.58. | C.6 |
| 1.1277 | B.59 | C.6 |
| 1.1278 | B.60 | C.6 |
| 1.1279 | B.61 | C.6 |
| 1.1280 | B.62 | C.6 |
| 1.1281 | B.63 | C.6 |
| 1.1282 | B.64 | C.6 |
| 1.1283 | B.65 | C.6 |
| 1.1284 | B.66 | C.6 |
| 1.1285 | B.67 | C.6 |
| 1.1286 | B.68 | C.6 |
| 1.1287 | B.69 | C.6 |
| 1.1288 | B.70 | C.6 |
| 1.1289 | B.71 | C.6 |
| 1.1290 | B.72 | C.6 |
| 1.1291 | B.73 | C.6 |
| 1.1292 | B.74 | C.6 |
| 1.1293 | B.75 | C.6 |
| 1.1294 | B.76 | C.6 |
| 1.1295 | B.77 | C.6 |
| 1.1296 | B.78 | C.6 |
| 1.1297 | B.79 | C.6 |
| 1.1298 | B.80 | C.6 |
| 1.1299 | B.81 | C.6 |
| 1.1300 | B.82 | C.6 |
| 1.1301 | B.83 | C.6 |
| 1.1302 | B.84 | C.6 |
| 1.1303 | B.85 | C.6 |
| 1.1304 | B.86 | C.6 |
| 1.1305 | B.87 | C.6 |
| 1.1306 | B.88 | C.6 |
| 1.1307 | B.89 | C.6 |
| 1.1308 | B.90 | C.6 |
| 1.1309 | B.91 | C.6 |
| 1.1310 | B.92 | C.6 |
| 1.1311 | B.93 | C.6 |
| 1.1312 | B.94 | C.6 |
| 1.1313 | B.95 | C.6 |
| 1.1314 | B.96 | C.6 |
| 1.1315 | B.97 | C.6 |
| 1.1316 | B.98 | C.6 |
| 1.1317 | B.99 | C.6 |
| 1.1318 | B.100 | C.6 |
| 1.1319 | B.101 | C.6 |
| 1.1320 | B.102 | C.6 |
| 1.1321 | B.103 | C.6 |
| 1.1322 | B.104 | C.6 |
| 1.1323 | B.105 | C.6 |
| 1.1324 | B.106 | C.6 |
| 1.1325 | B.107 | C.6 |
| 1.1326 | B.108 | C.6 |
| 1.1327 | B.109 | C.6 |
| 1.1328 | B.110 | C.6 |
| 1.1329 | B.111 | C.6 |
| 1.1330 | B.112 | C.6 |
| 1.1331 | B.113 | C.6 |
| 1.1332 | B.114 | C.6 |
| 1.1333 | B.115 | C.6 |
| 1.1334 | B.116 | C.6 |
| 1.1335 | B.117 | C.6 |
| 1.1336 | B.118 | C.6 |
| 1.1337 | B.119 | C.6 |
| 1.1338 | B.120 | C.6 |
| 1.1339 | B.121 | C.6 |
| 1.1340 | B.122 | C.6 |
| 1.1341 | B.123 | C.6 |
| 1.1342 | B.124 | C.6 |
| 1.1343 | B.125 | C.6 |
| 1.1344 | B.126 | C.6 |
| 1.1345 | B.127 | C.6 |
| 1.1346 | B.128 | C.6 |
| 1.1347 | B.129 | C.6 |
| 1.1348 | B.130 | C.6 |
| 1.1349 | B.131 | C.6 |
| 1.1350 | B.132 | C.6 |
| 1.1351 | B.133 | C.6 |
| 1.1352 | B.134 | C.6 |
| 1.1353 | B.135 | C.6 |
| 1.1354 | B.136 | C.6 |
| 1.1355 | B.137 | C.6 |
| 1.1356 | B.138 | C.6 |

TABLE 1-continued

| comp. no. | herbicide B | safener C |
|---|---|---|
| 1.1357 | B.139 | C.6 |
| 1.1358 | B.140 | C.6 |
| 1.1359 | B.141 | C.6 |
| 1.1360 | B.142 | C.6 |
| 1.1361 | B.143 | C.6 |
| 1.1362 | B.144 | C.6 |
| 1.1363 | B.145 | C.6 |
| 1.1364 | B.146 | C.6 |
| 1.1365 | B.147 | C.6 |
| 1.1366 | B.148 | C.6 |
| 1.1367 | B.149 | C.6 |
| 1.1368 | B.150 | C.6 |
| 1.1369 | B.151 | C.6 |
| 1.1370 | B.152 | C.6 |
| 1.1371 | B.153 | C.6 |
| 1.1372 | B.154 | C.6 |
| 1.1373 | B.155 | C.6 |
| 1.1374 | B.156 | C.6 |
| 1.1375 | B.157 | C.6 |
| 1.1376 | B.158 | C.6 |
| 1.1377 | B.159 | C.6 |
| 1.1378 | B.160 | C.6 |
| 1.1379 | B.161 | C.6 |
| 1.1380 | B.162 | C.6 |
| 1.1381 | B.163 | C.6 |
| 1.1382 | B.164 | C.6 |
| 1.1383 | B.165 | C.6 |
| 1.1384 | B.166 | C.6 |
| 1.1385 | B.167 | C.6 |
| 1.1386 | B.168 | C.6 |
| 1.1387 | B.169 | C.6 |
| 1.1388 | B.170 | C.6 |
| 1.1389 | B.171 | C.6 |
| 1.1390 | B.172 | C.6 |
| 1.1391 | B.173 | C.6 |
| 1.1392 | B.174 | C.6 |
| 1.1393 | B.175 | C.6 |
| 1.1394 | B.176 | C.6 |
| 1.1395 | B.177 | C.6 |
| 1.1396 | B.178 | C.6 |
| 1.1397 | B.179 | C.6 |
| 1.1398 | B.180 | C.6 |
| 1.1399 | B.181 | C.6 |
| 1.1400 | B.182 | C.6 |
| 1.1401 | B.183 | C.6 |
| 1.1402 | B.184 | C.6 |
| 1.1403 | B.185 | C.6 |
| 1.1404 | B.186 | C.6 |
| 1.1405 | B.187 | C.6 |
| 1.1406 | B.188 | C.6 |
| 1.1407 | B.189 | C.6 |
| 1.1408 | B.190 | C.6 |
| 1.1409 | B.191 | C.6 |
| 1.1410 | B.192 | C.6 |
| 1.1411 | B.193 | C.6 |
| 1.1412 | B.194 | C.6 |
| 1.1413 | B.195 | C.6 |
| 1.1414 | B.196 | C.6 |
| 1.1415 | B.197 | C.6 |
| 1.1416 | B.198 | C.6 |
| 1.1417 | B.199 | C.6 |
| 1.1418 | B.200 | C.6 |
| 1.1419 | B.201 | C.6 |
| 1.1420 | B.202 | C.6 |
| 1.1421 | B.203 | C.6 |
| 1.1422 | B.1 | C.7 |
| 1.1423 | B.2 | C.7 |
| 1.1424 | B.3 | C.7 |
| 1.1425 | B.4 | C.7 |
| 1.1426 | B.5 | C.7 |
| 1.1427 | B.6 | C.7 |
| 1.1428 | B.7 | C.7 |
| 1.1429 | B.8 | C.7 |
| 1.1430 | B.9 | C.7 |
| 1.1431 | B.10 | C.7 |
| 1.1432 | B.11 | C.7 |
| 1.1433 | B.12 | C.7 |
| 1.1434 | B.13 | C.7 |
| 1.1435 | B.14 | C.7 |
| 1.1436 | B.15 | C.7 |
| 1.1437 | B.16 | C.7 |
| 1.1438 | B.17 | C.7 |
| 1.1439 | B.18 | C.7 |
| 1.1440 | B.19 | C.7 |
| 1.1441 | B.20 | C.7 |
| 1.1442 | B.21 | C.7 |
| 1.1443 | B.22 | C.7 |
| 1.1444 | B.23 | C.7 |
| 1.1445 | B.24 | C.7 |
| 1.1446 | B.25 | C.7 |
| 1.1447 | B.26 | C.7 |
| 1.1448 | B.27 | C.7 |
| 1.1449 | B.28 | C.7 |
| 1.1450 | B.29 | C.7 |
| 1.1451 | B.30 | C.7 |
| 1.1452 | B.31 | C.7 |
| 1.1453 | B.32 | C.7 |
| 1.1454 | B.33 | C.7 |
| 1.1455 | B.34 | C.7 |
| 1.1456 | B.35 | C.7 |
| 1.1457 | B.36 | C.7 |
| 1.1458 | B.37 | C.7 |
| 1.1459 | B.38 | C.7 |
| 1.1460 | B.39 | C.7 |
| 1.1461 | B.40 | C.7 |
| 1.1462 | B.41 | C.7 |
| 1.1463 | B.42 | C.7 |
| 1.1464 | B.43 | C.7 |
| 1.1465 | B.44 | C.7 |
| 1.1466 | B.45 | C.7 |
| 1.1467 | B.46 | C.7 |
| 1.1468 | B.47 | C.7 |
| 1.1469 | B.48 | C.7 |
| 1.1470 | B.49 | C.7 |
| 1.1471 | B.50 | C.7 |
| 1.1472 | B.51 | C.7 |
| 1.1473 | B.52 | C.7 |
| 1.1474 | B.53 | C.7 |
| 1.1475 | B.54 | C.7 |
| 1.1476 | B.55 | C.7 |
| 1.1477 | B.56 | C.7 |
| 1.1478 | B.57 | C.7 |
| 1.1479 | B.58. | C.7 |
| 1.1480 | B.59 | C.7 |
| 1.1481 | B.60 | C.7 |
| 1.1482 | B.61 | C.7 |
| 1.1483 | B.62 | C.7 |
| 1.1484 | B.63 | C.7 |
| 1.1485 | B.64 | C.7 |
| 1.1486 | B.65 | C.7 |
| 1.1487 | B.66 | C.7 |
| 1.1488 | B.67 | C.7 |
| 1.1489 | B.68 | C.7 |
| 1.1490 | B.69 | C.7 |
| 1.1491 | B.70 | C.7 |
| 1.1492 | B.71 | C.7 |
| 1.1493 | B.72 | C.7 |
| 1.1494 | B.73 | C.7 |
| 1.1495 | B.74 | C.7 |
| 1.1496 | B.75 | C.7 |
| 1.1497 | B.76 | C.7 |
| 1.1498 | B.77 | C.7 |
| 1.1499 | B.78 | C.7 |
| 1.1500 | B.79 | C.7 |
| 1.1501 | B.80 | C.7 |
| 1.1502 | B.81 | C.7 |
| 1.1503 | B.82 | C.7 |
| 1.1504 | B.83 | C.7 |
| 1.1505 | B.84 | C.7 |
| 1.1506 | B.85 | C.7 |
| 1.1507 | B.86 | C.7 |
| 1.1508 | B.87 | C.7 |
| 1.1509 | B.88 | C.7 |
| 1.1510 | B.89 | C.7 |
| 1.1511 | B.90 | C.7 |
| 1.1512 | B.91 | C.7 |

TABLE 1-continued

| comp. no. | herbicide B | safener C |
|---|---|---|
| 1.1513 | B.92 | C.7 |
| 1.1514 | B.93 | C.7 |
| 1.1515 | B.94 | C.7 |
| 1.1516 | B.95 | C.7 |
| 1.1517 | B.96 | C.7 |
| 1.1518 | B.97 | C.7 |
| 1.1519 | B.98 | C.7 |
| 1.1520 | B.99 | C.7 |
| 1.1521 | B.100 | C.7 |
| 1.1522 | B.101 | C.7 |
| 1.1523 | B.102 | C.7 |
| 1.1524 | B.103 | C.7 |
| 1.1525 | B.104 | C.7 |
| 1.1526 | B.105 | C.7 |
| 1.1527 | B.106 | C.7 |
| 1.1528 | B.107 | C.7 |
| 1.1529 | B.108 | C.7 |
| 1.1530 | B.109 | C.7 |
| 1.1531 | B.110 | C.7 |
| 1.1532 | B.111 | C.7 |
| 1.1533 | B.112 | C.7 |
| 1.1534 | B.113 | C.7 |
| 1.1535 | B.114 | C.7 |
| 1.1536 | B.115 | C.7 |
| 1.1537 | B.116 | C.7 |
| 1.1538 | B.117 | C.7 |
| 1.1539 | B.118 | C.7 |
| 1.1540 | B.119 | C.7 |
| 1.1541 | B.120 | C.7 |
| 1.1542 | B.121 | C.7 |
| 1.1543 | B.122 | C.7 |
| 1.1544 | B.123 | C.7 |
| 1.1545 | B.124 | C.7 |
| 1.1546 | B.125 | C.7 |
| 1.1547 | B.126 | C.7 |
| 1.1548 | B.127 | C.7 |
| 1.1549 | B.128 | C.7 |
| 1.1550 | B.129 | C.7 |
| 1.1551 | B.130 | C.7 |
| 1.1552 | B.131 | C.7 |
| 1.1553 | B.132 | C.7 |
| 1.1554 | B.133 | C.7 |
| 1.1555 | B.134 | C.7 |
| 1.1556 | B.135 | C.7 |
| 1.1557 | B.136 | C.7 |
| 1.1558 | B.137 | C.7 |
| 1.1559 | B.138 | C.7 |
| 1.1560 | B.139 | C.7 |
| 1.1561 | B.140 | C.7 |
| 1.1562 | B.141 | C.7 |
| 1.1563 | B.142 | C.7 |
| 1.1564 | B.143 | C.7 |
| 1.1565 | B.144 | C.7 |
| 1.1566 | B.145 | C.7 |
| 1.1567 | B.146 | C.7 |
| 1.1568 | B.147 | C.7 |
| 1.1569 | B.148 | C.7 |
| 1.1570 | B.149 | C.7 |
| 1.1571 | B.150 | C.7 |
| 1.1572 | B.151 | C.7 |
| 1.1573 | B.152 | C.7 |
| 1.1574 | B.153 | C.7 |
| 1.1575 | B.154 | C.7 |
| 1.1576 | B.155 | C.7 |
| 1.1577 | B.156 | C.7 |
| 1.1578 | B.157 | C.7 |
| 1.1579 | B.158 | C.7 |
| 1.1580 | B.159 | C.7 |
| 1.1581 | B.160 | C.7 |
| 1.1582 | B.161 | C.7 |
| 1.1583 | B.162 | C.7 |
| 1.1584 | B.163 | C.7 |
| 1.1585 | B.164 | C.7 |
| 1.1586 | B.165 | C.7 |
| 1.1587 | B.166 | C.7 |
| 1.1588 | B.167 | C.7 |
| 1.1589 | B.168 | C.7 |
| 1.1590 | B.169 | C.7 |
| 1.1591 | B.170 | C.7 |
| 1.1592 | B.171 | C.7 |
| 1.1593 | B.172 | C.7 |
| 1.1594 | B.173 | C.7 |
| 1.1595 | B.174 | C.7 |
| 1.1596 | B.175 | C.7 |
| 1.1597 | B.176 | C.7 |
| 1.1598 | B.177 | C.7 |
| 1.1599 | B.178 | C.7 |
| 1.1600 | B.179 | C.7 |
| 1.1601 | B.180 | C.7 |
| 1.1602 | B.181 | C.7 |
| 1.1603 | B.182 | C.7 |
| 1.1604 | B.183 | C.7 |
| 1.1605 | B.184 | C.7 |
| 1.1606 | B.185 | C.7 |
| 1.1607 | B.186 | C.7 |
| 1.1608 | B.187 | C.7 |
| 1.1609 | B.188 | C.7 |
| 1.1610 | B.189 | C.7 |
| 1.1611 | B.190 | C.7 |
| 1.1612 | B.191 | C.7 |
| 1.1613 | B.192 | C.7 |
| 1.1614 | B.193 | C.7 |
| 1.1615 | B.194 | C.7 |
| 1.1616 | B.195 | C.7 |
| 1.1617 | B.196 | C.7 |
| 1.1618 | B.197 | C.7 |
| 1.1619 | B.198 | C.7 |
| 1.1620 | B.199 | C.7 |
| 1.1621 | B.200 | C.7 |
| 1.1622 | B.201 | C.7 |
| 1.1623 | B.202 | C.7 |
| 1.1624 | B.203 | C.7 |
| 1.1625 | B.1 | C.8 |
| 1.1626 | B.2 | C.8 |
| 1.1627 | B.3 | C.8 |
| 1.1628 | B.4 | C.8 |
| 1.1629 | B.5 | C.8 |
| 1.1630 | B.6 | C.8 |
| 1.1631 | B.7 | C.8 |
| 1.1632 | B.8 | C.8 |
| 1.1633 | B.9 | C.8 |
| 1.1634 | B.10 | C.8 |
| 1.1635 | B.11 | C.8 |
| 1.1636 | B.12 | C.8 |
| 1.1637 | B.13 | C.8 |
| 1.1638 | B.14 | C.8 |
| 1.1639 | B.15 | C.8 |
| 1.1640 | B.16 | C.8 |
| 1.1641 | B.17 | C.8 |
| 1.1642 | B.18 | C.8 |
| 1.1643 | B.19 | C.8 |
| 1.1644 | B.20 | C.8 |
| 1.1645 | B.21 | C.8 |
| 1.1646 | B.22 | C.8 |
| 1.1647 | B.23 | C.8 |
| 1.1648 | B.24 | C.8 |
| 1.1649 | B.25 | C.8 |
| 1.1650 | B.26 | C.8 |
| 1.1651 | B.27 | C.8 |
| 1.1652 | B.28 | C.8 |
| 1.1653 | B.29 | C.8 |
| 1.1654 | B.30 | C.8 |
| 1.1655 | B.31 | C.8 |
| 1.1656 | B.32 | C.8 |
| 1.1657 | B.33 | C.8 |
| 1.1658 | B.34 | C.8 |
| 1.1659 | B.35 | C.8 |
| 1.1660 | B.36 | C.8 |
| 1.1661 | B.37 | C.8 |
| 1.1662 | B.38 | C.8 |
| 1.1663 | B.39 | C.8 |
| 1.1664 | B.40 | C.8 |
| 1.1665 | B.41 | C.8 |
| 1.1666 | B.42 | C.8 |
| 1.1667 | B.43 | C.8 |
| 1.1668 | B.44 | C.8 |

TABLE 1-continued

| comp. no. | herbicide B | safener C |
|---|---|---|
| 1.1669 | B.45 | C.8 |
| 1.1670 | B.46 | C.8 |
| 1.1671 | B.47 | C.8 |
| 1.1672 | B.48 | C.8 |
| 1.1673 | B.49 | C.8 |
| 1.1674 | B.50 | C.8 |
| 1.1675 | B.51 | C.8 |
| 1.1676 | B.52 | C.8 |
| 1.1677 | B.53 | C.8 |
| 1.1678 | B.54 | C.8 |
| 1.1679 | B.55 | C.8 |
| 1.1680 | B.56 | C.8 |
| 1.1681 | B.57 | C.8 |
| 1.1682 | B.58. | C.8 |
| 1.1683 | B.59 | C.8 |
| 1.1684 | B.60 | C.8 |
| 1.1685 | B.61 | C.8 |
| 1.1686 | B.62 | C.8 |
| 1.1687 | B.63 | C.8 |
| 1.1688 | B.64 | C.8 |
| 1.1689 | B.65 | C.8 |
| 1.1690 | B.66 | C.8 |
| 1.1691 | B.67 | C.8 |
| 1.1692 | B.68 | C.8 |
| 1.1693 | B.69 | C.8 |
| 1.1694 | B.70 | C.8 |
| 1.1695 | B.71 | C.8 |
| 1.1696 | B.72 | C.8 |
| 1.1697 | B.73 | C.8 |
| 1.1698 | B.74 | C.8 |
| 1.1699 | B.75 | C.8 |
| 1.1700 | B.76 | C.8 |
| 1.1701 | B.77 | C.8 |
| 1.1702 | B.78 | C.8 |
| 1.1703 | B.79 | C.8 |
| 1.1704 | B.80 | C.8 |
| 1.1705 | B.81 | C.8 |
| 1.1706 | B.82 | C.8 |
| 1.1707 | B.83 | C.8 |
| 1.1708 | B.84 | C.8 |
| 1.1709 | B.85 | C.8 |
| 1.1710 | B.86 | C.8 |
| 1.1711 | B.87 | C.8 |
| 1.1712 | B.88 | C.8 |
| 1.1713 | B.89 | C.8 |
| 1.1714 | B.90 | C.8 |
| 1.1715 | B.91 | C.8 |
| 1.1716 | B.92 | C.8 |
| 1.1717 | B.93 | C.8 |
| 1.1718 | B.94 | C.8 |
| 1.1719 | B.95 | C.8 |
| 1.1720 | B.96 | C.8 |
| 1.1721 | B.97 | C.8 |
| 1.1722 | B.98 | C.8 |
| 1.1723 | B.99 | C.8 |
| 1.1724 | B.100 | C.8 |
| 1.1725 | B.101 | C.8 |
| 1.1726 | B.102 | C.8 |
| 1.1727 | B.103 | C.8 |
| 1.1728 | B.104 | C.8 |
| 1.1729 | B.105 | C.8 |
| 1.1730 | B.106 | C.8 |
| 1.1731 | B.107 | C.8 |
| 1.1732 | B.108 | C.8 |
| 1.1733 | B.109 | C.8 |
| 1.1734 | B.110 | C.8 |
| 1.1735 | B.111 | C.8 |
| 1.1736 | B.112 | C.8 |
| 1.1737 | B.113 | C.8 |
| 1.1738 | B.114 | C.8 |
| 1.1739 | B.115 | C.8 |
| 1.1740 | B.116 | C.8 |
| 1.1741 | B.117 | C.8 |
| 1.1742 | B.118 | C.8 |
| 1.1743 | B.119 | C.8 |
| 1.1744 | B.120 | C.8 |
| 1.1745 | B.121 | C.8 |
| 1.1746 | B.122 | C.8 |
| 1.1747 | B.123 | C.8 |
| 1.1748 | B.124 | C.8 |
| 1.1749 | B.125 | C.8 |
| 1.1750 | B.126 | C.8 |
| 1.1751 | B.127 | C.8 |
| 1.1752 | B.128 | C.8 |
| 1.1753 | B.129 | C.8 |
| 1.1754 | B.130 | C.8 |
| 1.1755 | B.131 | C.8 |
| 1.1756 | B.132 | C.8 |
| 1.1757 | B.133 | C.8 |
| 1.1758 | B.134 | C.8 |
| 1.1759 | B.135 | C.8 |
| 1.1760 | B.136 | C.8 |
| 1.1761 | B.137 | C.8 |
| 1.1762 | B.138 | C.8 |
| 1.1763 | B.139 | C.8 |
| 1.1764 | B.140 | C.8 |
| 1.1765 | B.141 | C.8 |
| 1.1766 | B.142 | C.8 |
| 1.1767 | B.143 | C.8 |
| 1.1768 | B.144 | C.8 |
| 1.1769 | B.145 | C.8 |
| 1.1770 | B.146 | C.8 |
| 1.1771 | B.147 | C.8 |
| 1.1772 | B.148 | C.8 |
| 1.1773 | B.149 | C.8 |
| 1.1774 | B.150 | C.8 |
| 1.1775 | B.151 | C.8 |
| 1.1776 | B.152 | C.8 |
| 1.1777 | B.153 | C.8 |
| 1.1778 | B.154 | C.8 |
| 1.1779 | B.155 | C.8 |
| 1.1780 | B.156 | C.8 |
| 1.1781 | B.157 | C.8 |
| 1.1782 | B.158 | C.8 |
| 1.1783 | B.159 | C.8 |
| 1.1784 | B.160 | C.8 |
| 1.1785 | B.161 | C.8 |
| 1.1786 | B.162 | C.8 |
| 1.1787 | B.163 | C.8 |
| 1.1788 | B.164 | C.8 |
| 1.1789 | B.165 | C.8 |
| 1.1790 | B.166 | C.8 |
| 1.1791 | B.167 | C.8 |
| 1.1792 | B.168 | C.8 |
| 1.1793 | B.169 | C.8 |
| 1.1794 | B.170 | C.8 |
| 1.1795 | B.171 | C.8 |
| 1.1796 | B.172 | C.8 |
| 1.1797 | B.173 | C.8 |
| 1.1798 | B.174 | C.8 |
| 1.1799 | B.175 | C.8 |
| 1.1800 | B.176 | C.8 |
| 1.1801 | B.177 | C.8 |
| 1.1802 | B.178 | C.8 |
| 1.1803 | B.179 | C.8 |
| 1.1804 | B.180 | C.8 |
| 1.1805 | B.181 | C.8 |
| 1.1806 | B.182 | C.8 |
| 1.1807 | B.183 | C.8 |
| 1.1808 | B.184 | C.8 |
| 1.1809 | B.185 | C.8 |
| 1.1810 | B.186 | C.8 |
| 1.1811 | B.187 | C.8 |
| 1.1812 | B.188 | C.8 |
| 1.1813 | B.189 | C.8 |
| 1.1814 | B.190 | C.8 |
| 1.1815 | B.191 | C.8 |
| 1.1816 | B.192 | C.8 |
| 1.1817 | B.193 | C.8 |
| 1.1818 | B.194 | C.8 |
| 1.1819 | B.195 | C.8 |
| 1.1820 | B.196 | C.8 |
| 1.1821 | B.197 | C.8 |
| 1.1822 | B.198 | C.8 |
| 1.1823 | B.199 | C.8 |
| 1.1824 | B.200 | C.8 |

TABLE 1-continued

| comp. no. | herbicide B | safener C |
|---|---|---|
| 1.1825 | B.201 | C.8 |
| 1.1826 | B.202 | C.8 |
| 1.1827 | B.203 | C.8 |
| 1.1828 | B.1 | C.9 |
| 1.1829 | B.2 | C.9 |
| 1.1830 | B.3 | C.9 |
| 1.1831 | B.4 | C.9 |
| 1.1832 | B.5 | C.9 |
| 1.1833 | B.6 | C.9 |
| 1.1834 | B.7 | C.9 |
| 1.1835 | B.8 | C.9 |
| 1.1836 | B.9 | C.9 |
| 1.1837 | B.10 | C.9 |
| 1.1838 | B.11 | C.9 |
| 1.1839 | B.12 | C.9 |
| 1.1840 | B.13 | C.9 |
| 1.1841 | B.14 | C.9 |
| 1.1842 | B.15 | C.9 |
| 1.1843 | B.16 | C.9 |
| 1.1844 | B.17 | C.9 |
| 1.1845 | B.18 | C.9 |
| 1.1846 | B.19 | C.9 |
| 1.1847 | B.20 | C.9 |
| 1.1848 | B.21 | C.9 |
| 1.1849 | B.22 | C.9 |
| 1.1850 | B.23 | C.9 |
| 1.1851 | B.24 | C.9 |
| 1.1852 | B.25 | C.9 |
| 1.1853 | B.26 | C.9 |
| 1.1854 | B.27 | C.9 |
| 1.1855 | B.28 | C.9 |
| 1.1856 | B.29 | C.9 |
| 1.1857 | B.30 | C.9 |
| 1.1858 | B.31 | C.9 |
| 1.1859 | B.32 | C.9 |
| 1.1860 | B.33 | C.9 |
| 1.1861 | B.34 | C.9 |
| 1.1862 | B.35 | C.9 |
| 1.1863 | B.36 | C.9 |
| 1.1864 | B.37 | C.9 |
| 1.1865 | B.38 | C.9 |
| 1.1866 | B.39 | C.9 |
| 1.1867 | B.40 | C.9 |
| 1.1868 | B.41 | C.9 |
| 1.1869 | B.42 | C.9 |
| 1.1870 | B.43 | C.9 |
| 1.1871 | B.44 | C.9 |
| 1.1872 | B.45 | C.9 |
| 1.1873 | B.46 | C.9 |
| 1.1874 | B.47 | C.9 |
| 1.1875 | B.48 | C.9 |
| 1.1876 | B.49 | C.9 |
| 1.1877 | B.50 | C.9 |
| 1.1878 | B.51 | C.9 |
| 1.1879 | B.52 | C.9 |
| 1.1880 | B.53 | C.9 |
| 1.1881 | B.54 | C.9 |
| 1.1882 | B.55 | C.9 |
| 1.1883 | B.56 | C.9 |
| 1.1884 | B.57 | C.9 |
| 1.1885 | B.58. | C.9 |
| 1.1886 | B.59 | C.9 |
| 1.1887 | B.60 | C.9 |
| 1.1888 | B.61 | C.9 |
| 1.1889 | B.62 | C.9 |
| 1.1890 | B.63 | C.9 |
| 1.1891 | B.64 | C.9 |
| 1.1892 | B.65 | C.9 |
| 1.1893 | B.66 | C.9 |
| 1.1894 | B.67 | C.9 |
| 1.1895 | B.68 | C.9 |
| 1.1896 | B.69 | C.9 |
| 1.1897 | B.70 | C.9 |
| 1.1898 | B.71 | C.9 |
| 1.1899 | B.72 | C.9 |
| 1.1900 | B.73 | C.9 |
| 1.1901 | B.74 | C.9 |
| 1.1902 | B.75 | C.9 |
| 1.1903 | B.76 | C.9 |
| 1.1904 | B.77 | C.9 |
| 1.1905 | B.78 | C.9 |
| 1.1906 | B.79 | C.9 |
| 1.1907 | B.80 | C.9 |
| 1.1908 | B.81 | C.9 |
| 1.1909 | B.82 | C.9 |
| 1.1910 | B.83 | C.9 |
| 1.1911 | B.84 | C.9 |
| 1.1912 | B.85 | C.9 |
| 1.1913 | B.86 | C.9 |
| 1.1914 | B.87 | C.9 |
| 1.1915 | B.88 | C.9 |
| 1.1916 | B.89 | C.9 |
| 1.1917 | B.90 | C.9 |
| 1.1918 | B.91 | C.9 |
| 1.1919 | B.92 | C.9 |
| 1.1920 | B.93 | C.9 |
| 1.1921 | B.94 | C.9 |
| 1.1922 | B.95 | C.9 |
| 1.1923 | B.96 | C.9 |
| 1.1924 | B.97 | C.9 |
| 1.1925 | B.98 | C.9 |
| 1.1926 | B.99 | C.9 |
| 1.1927 | B.100 | C.9 |
| 1.1928 | B.101 | C.9 |
| 1.1929 | B.102 | C.9 |
| 1.1930 | B.103 | C.9 |
| 1.1931 | B.104 | C.9 |
| 1.1932 | B.105 | C.9 |
| 1.1933 | B.106 | C.9 |
| 1.1934 | B.107 | C.9 |
| 1.1935 | B.108 | C.9 |
| 1.1936 | B.109 | C.9 |
| 1.1937 | B.110 | C.9 |
| 1.1938 | B.111 | C.9 |
| 1.1939 | B.112 | C.9 |
| 1.1940 | B.113 | C.9 |
| 1.1941 | B.114 | C.9 |
| 1.1942 | B.115 | C.9 |
| 1.1943 | B.116 | C.9 |
| 1.1944 | B.117 | C.9 |
| 1.1945 | B.118 | C.9 |
| 1.1946 | B.119 | C.9 |
| 1.1947 | B.120 | C.9 |
| 1.1948 | B.121 | C.9 |
| 1.1949 | B.122 | C.9 |
| 1.1950 | B.123 | C.9 |
| 1.1951 | B.124 | C.9 |
| 1.1952 | B.125 | C.9 |
| 1.1953 | B.126 | C.9 |
| 1.1954 | B.127 | C.9 |
| 1.1955 | B.128 | C.9 |
| 1.1956 | B.129 | C.9 |
| 1.1957 | B.130 | C.9 |
| 1.1958 | B.131 | C.9 |
| 1.1959 | B.132 | C.9 |
| 1.1960 | B.133 | C.9 |
| 1.1961 | B.134 | C.9 |
| 1.1962 | B.135 | C.9 |
| 1.1963 | B.136 | C.9 |
| 1.1964 | B.137 | C.9 |
| 1.1965 | B.138 | C.9 |
| 1.1966 | B.139 | C.9 |
| 1.1967 | B.140 | C.9 |
| 1.1968 | B.141 | C.9 |
| 1.1969 | B.142 | C.9 |
| 1.1970 | B.143 | C.9 |
| 1.1971 | B.144 | C.9 |
| 1.1972 | B.145 | C.9 |
| 1.1973 | B.146 | C.9 |
| 1.1974 | B.147 | C.9 |
| 1.1975 | B.148 | C.9 |
| 1.1976 | B.149 | C.9 |
| 1.1977 | B.150 | C.9 |
| 1.1978 | B.151 | C.9 |
| 1.1979 | B.152 | C.9 |
| 1.1980 | B.153 | C.9 |

TABLE 1-continued

| comp. no. | herbicide B | safener C |
|---|---|---|
| 1.1981 | B.154 | C.9 |
| 1.1982 | B.155 | C.9 |
| 1.1983 | B.156 | C.9 |
| 1.1984 | B.157 | C.9 |
| 1.1985 | B.158 | C.9 |
| 1.1986 | B.159 | C.9 |
| 1.1987 | B.160 | C.9 |
| 1.1988 | B.161 | C.9 |
| 1.1989 | B.162 | C.9 |
| 1.1990 | B.163 | C.9 |
| 1.1991 | B.164 | C.9 |
| 1.1992 | B.165 | C.9 |
| 1.1993 | B.166 | C.9 |
| 1.1994 | B.167 | C.9 |
| 1.1995 | B.168 | C.9 |
| 1.1996 | B.169 | C.9 |
| 1.1997 | B.170 | C.9 |
| 1.1998 | B.171 | C.9 |
| 1.1999 | B.172 | C.9 |
| 1.2000 | B.173 | C.9 |
| 1.2001 | B.174 | C.9 |
| 1.2002 | B.175 | C.9 |
| 1.2003 | B.176 | C.9 |
| 1.2004 | B.177 | C.9 |
| 1.2005 | B.178 | C.9 |
| 1.2006 | B.179 | C.9 |
| 1.2007 | B.180 | C.9 |
| 1.2008 | B.181 | C.9 |
| 1.2009 | B.182 | C.9 |
| 1.2010 | B.183 | C.9 |
| 1.2011 | B.184 | C.9 |
| 1.2012 | B.185 | C.9 |
| 1.2013 | B.186 | C.9 |
| 1.2014 | B.187 | C.9 |
| 1.2015 | B.188 | C.9 |
| 1.2016 | B.189 | C.9 |
| 1.2017 | B.190 | C.9 |
| 1.2018 | B.191 | C.9 |
| 1.2019 | B.192 | C.9 |
| 1.2020 | B.193 | C.9 |
| 1.2021 | B.194 | C.9 |
| 1.2022 | B.195 | C.9 |
| 1.2023 | B.196 | C.9 |
| 1.2024 | B.197 | C.9 |
| 1.2025 | B.198 | C.9 |
| 1.2026 | B.199 | C.9 |
| 1.2027 | B.200 | C.9 |
| 1.2028 | B.201 | C.9 |
| 1.2029 | B.202 | C.9 |
| 1.2030 | B.203 | C.9 |
| 1.2031 | B.1 | C.10 |
| 1.2032 | B.2 | C.10 |
| 1.2033 | B.3 | C.10 |
| 1.2034 | B.4 | C.10 |
| 1.2035 | B.5 | C.10 |
| 1.2036 | B.6 | C.10 |
| 1.2037 | B.7 | C.10 |
| 1.2038 | B.8 | C.10 |
| 1.2039 | B.9 | C.10 |
| 1.2040 | B.10 | C.10 |
| 1.2041 | B.11 | C.10 |
| 1.2042 | B.12 | C.10 |
| 1.2043 | B.13 | C.10 |
| 1.2044 | B.14 | C.10 |
| 1.2045 | B.15 | C.10 |
| 1.2046 | B.16 | C.10 |
| 1.2047 | B.17 | C.10 |
| 1.2048 | B.18 | C.10 |
| 1.2049 | B.19 | C.10 |
| 1.2050 | B.20 | C.10 |
| 1.2051 | B.21 | C.10 |
| 1.2052 | B.22 | C.10 |
| 1.2053 | B.23 | C.10 |
| 1.2054 | B.24 | C.10 |
| 1.2055 | B.25 | C.10 |
| 1.2056 | B.26 | C.10 |
| 1.2057 | B.27 | C.10 |
| 1.2058 | B.28 | C.10 |
| 1.2059 | B.29 | C.10 |
| 1.2060 | B.30 | C.10 |
| 1.2061 | B.31 | C.10 |
| 1.2062 | B.32 | C.10 |
| 1.2063 | B.33 | C.10 |
| 1.2064 | B.34 | C.10 |
| 1.2065 | B.35 | C.10 |
| 1.2066 | B.36 | C.10 |
| 1.2067 | B.37 | C.10 |
| 1.2068 | B.38 | C.10 |
| 1.2069 | B.39 | C.10 |
| 1.2070 | B.40 | C.10 |
| 1.2071 | B.41 | C.10 |
| 1.2072 | B.42 | C.10 |
| 1.2073 | B.43 | C.10 |
| 1.2074 | B.44 | C.10 |
| 1.2075 | B.45 | C.10 |
| 1.2076 | B.46 | C.10 |
| 1.2077 | B.47 | C.10 |
| 1.2078 | B.48 | C.10 |
| 1.2079 | B.49 | C.10 |
| 1.2080 | B.50 | C.10 |
| 1.2081 | B.51 | C.10 |
| 1.2082 | B.52 | C.10 |
| 1.2083 | B.53 | C.10 |
| 1.2084 | B.54 | C.10 |
| 1.2085 | B.55 | C.10 |
| 1.2086 | B.56 | C.10 |
| 1.2087 | B.57 | C.10 |
| 1.2088 | B.58. | C.10 |
| 1.2089 | B.59 | C.10 |
| 1.2090 | B.60 | C.10 |
| 1.2091 | B.61 | C.10 |
| 1.2092 | B.62 | C.10 |
| 1.2093 | B.63 | C.10 |
| 1.2094 | B.64 | C.10 |
| 1.2095 | B.65 | C.10 |
| 1.2096 | B.66 | C.10 |
| 1.2097 | B.67 | C.10 |
| 1.2098 | B.68 | C.10 |
| 1.2099 | B.69 | C.10 |
| 1.2100 | B.70 | C.10 |
| 1.2101 | B.71 | C.10 |
| 1.2102 | B.72 | C.10 |
| 1.2103 | B.73 | C.10 |
| 1.2104 | B.74 | C.10 |
| 1.2105 | B.75 | C.10 |
| 1.2106 | B.76 | C.10 |
| 1.2107 | B.77 | C.10 |
| 1.2108 | B.78 | C.10 |
| 1.2109 | B.79 | C.10 |
| 1.2110 | B.80 | C.10 |
| 1.2111 | B.81 | C.10 |
| 1.2112 | B.82 | C.10 |
| 1.2113 | B.83 | C.10 |
| 1.2114 | B.84 | C.10 |
| 1.2115 | B.85 | C.10 |
| 1.2116 | B.86 | C.10 |
| 1.2117 | B.87 | C.10 |
| 1.2118 | B.88 | C.10 |
| 1.2119 | B.89 | C.10 |
| 1.2120 | B.90 | C.10 |
| 1.2121 | B.91 | C.10 |
| 1.2122 | B.92 | C.10 |
| 1.2123 | B.93 | C.10 |
| 1.2124 | B.94 | C.10 |
| 1.2125 | B.95 | C.10 |
| 1.2126 | B.96 | C.10 |
| 1.2127 | B.97 | C.10 |
| 1.2128 | B.98 | C.10 |
| 1.2129 | B.99 | C.10 |
| 1.2130 | B.100 | C.10 |
| 1.2131 | B.101 | C.10 |
| 1.2132 | B.102 | C.10 |
| 1.2133 | B.103 | C.10 |
| 1.2134 | B.104 | C.10 |
| 1.2135 | B.105 | C.10 |
| 1.2136 | B.106 | C.10 |

TABLE 1-continued

| comp. no. | herbicide B | safener C |
|---|---|---|
| 1.2137 | B.107 | C.10 |
| 1.2138 | B.108 | C.10 |
| 1.2139 | B.109 | C.10 |
| 1.2140 | B.110 | C.10 |
| 1.2141 | B.111 | C.10 |
| 1.2142 | B.112 | C.10 |
| 1.2143 | B.113 | C.10 |
| 1.2144 | B.114 | C.10 |
| 1.2145 | B.115 | C.10 |
| 1.2146 | B.116 | C.10 |
| 1.2147 | B.117 | C.10 |
| 1.2148 | B.118 | C.10 |
| 1.2149 | B.119 | C.10 |
| 1.2150 | B.120 | C.10 |
| 1.2151 | B.121 | C.10 |
| 1.2152 | B.122 | C.10 |
| 1.2153 | B.123 | C.10 |
| 1.2154 | B.124 | C.10 |
| 1.2155 | B.125 | C.10 |
| 1.2156 | B.126 | C.10 |
| 1.2157 | B.127 | C.10 |
| 1.2158 | B.128 | C.10 |
| 1.2159 | B.129 | C.10 |
| 1.2160 | B.130 | C.10 |
| 1.2161 | B.131 | C.10 |
| 1.2162 | B.132 | C.10 |
| 1.2163 | B.133 | C.10 |
| 1.2164 | B.134 | C.10 |
| 1.2165 | B.135 | C.10 |
| 1.2166 | B.136 | C.10 |
| 1.2167 | B.137 | C.10 |
| 1.2168 | B.138 | C.10 |
| 1.2169 | B.139 | C.10 |
| 1.2170 | B.140 | C.10 |
| 1.2171 | B.141 | C.10 |
| 1.2172 | B.142 | C.10 |
| 1.2173 | B.143 | C.10 |
| 1.2174 | B.144 | C.10 |
| 1.2175 | B.145 | C.10 |
| 1.2176 | B.146 | C.10 |
| 1.2177 | B.147 | C.10 |
| 1.2178 | B.148 | C.10 |
| 1.2179 | B.149 | C.10 |
| 1.2180 | B.150 | C.10 |
| 1.2181 | B.151 | C.10 |
| 1.2182 | B.152 | C.10 |
| 1.2183 | B.153 | C.10 |
| 1.2184 | B.154 | C.10 |
| 1.2185 | B.155 | C.10 |
| 1.2186 | B.156 | C.10 |
| 1.2187 | B.157 | C.10 |
| 1.2188 | B.158 | C.10 |
| 1.2189 | B.159 | C.10 |
| 1.2190 | B.160 | C.10 |
| 1.2191 | B.161 | C.10 |
| 1.2192 | B.162 | C.10 |
| 1.2193 | B.163 | C.10 |
| 1.2194 | B.164 | C.10 |
| 1.2195 | B.165 | C.10 |
| 1.2196 | B.166 | C.10 |
| 1.2197 | B.167 | C.10 |
| 1.2198 | B.168 | C.10 |
| 1.2199 | B.169 | C.10 |
| 1.2200 | B.170 | C.10 |
| 1.2201 | B.171 | C.10 |
| 1.2202 | B.172 | C.10 |
| 1.2203 | B.173 | C.10 |
| 1.2204 | B.174 | C.10 |
| 1.2205 | B.175 | C.10 |
| 1.2206 | B.176 | C.10 |
| 1.2207 | B.177 | C.10 |
| 1.2208 | B.178 | C.10 |
| 1.2209 | B.179 | C.10 |
| 1.2210 | B.180 | C.10 |
| 1.2211 | B.181 | C.10 |
| 1.2212 | B.182 | C.10 |
| 1.2213 | B.183 | C.10 |
| 1.2214 | B.184 | C.10 |
| 1.2215 | B.185 | C.10 |
| 1.2216 | B.186 | C.10 |
| 1.2217 | B.187 | C.10 |
| 1.2218 | B.188 | C.10 |
| 1.2219 | B.189 | C.10 |
| 1.2220 | B.190 | C.10 |
| 1.2221 | B.191 | C.10 |
| 1.2222 | B.192 | C.10 |
| 1.2223 | B.193 | C.10 |
| 1.2224 | B.194 | C.10 |
| 1.2225 | B.195 | C.10 |
| 1.2226 | B.196 | C.10 |
| 1.2227 | B.197 | C.10 |
| 1.2228 | B.198 | C.10 |
| 1.2229 | B.199 | C.10 |
| 1.2230 | B.200 | C.10 |
| 1.2231 | B.201 | C.10 |
| 1.2232 | B.202 | C.10 |
| 1.2233 | B.203 | C.10 |
| 1.2234 | B.1 | C.11 |
| 1.2235 | B.2 | C.11 |
| 1.2236 | B.3 | C.11 |
| 1.2237 | B.4 | C.11 |
| 1.2238 | B.5 | C.11 |
| 1.2239 | B.6 | C.11 |
| 1.2240 | B.7 | C.11 |
| 1.2241 | B.8 | C.11 |
| 1.2242 | B.9 | C.11 |
| 1.2243 | B.10 | C.11 |
| 1.2244 | B.11 | C.11 |
| 1.2245 | B.12 | C.11 |
| 1.2246 | B.13 | C.11 |
| 1.2247 | B.14 | C.11 |
| 1.2248 | B.15 | C.11 |
| 1.2249 | B.16 | C.11 |
| 1.2250 | B.17 | C.11 |
| 1.2251 | B.18 | C.11 |
| 1.2252 | B.19 | C.11 |
| 1.2253 | B.20 | C.11 |
| 1.2254 | B.21 | C.11 |
| 1.2255 | B.22 | C.11 |
| 1.2256 | B.23 | C.11 |
| 1.2257 | B.24 | C.11 |
| 1.2258 | B.25 | C.11 |
| 1.2259 | B.26 | C.11 |
| 1.2260 | B.27 | C.11 |
| 1.2261 | B.28 | C.11 |
| 1.2262 | B.29 | C.11 |
| 1.2263 | B.30 | C.11 |
| 1.2264 | B.31 | C.11 |
| 1.2265 | B.32 | C.11 |
| 1.2266 | B.33 | C.11 |
| 1.2267 | B.34 | C.11 |
| 1.2268 | B.35 | C.11 |
| 1.2269 | B.36 | C.11 |
| 1.2270 | B.37 | C.11 |
| 1.2271 | B.38 | C.11 |
| 1.2272 | B.39 | C.11 |
| 1.2273 | B.40 | C.11 |
| 1.2274 | B.41 | C.11 |
| 1.2275 | B.42 | C.11 |
| 1.2276 | B.43 | C.11 |
| 1.2277 | B.44 | C.11 |
| 1.2278 | B.45 | C.11 |
| 1.2279 | B.46 | C.11 |
| 1.2280 | B.47 | C.11 |
| 1.2281 | B.48 | C.11 |
| 1.2282 | B.49 | C.11 |
| 1.2283 | B.50 | C.11 |
| 1.2284 | B.51 | C.11 |
| 1.2285 | B.52 | C.11 |
| 1.2286 | B.53 | C.11 |
| 1.2287 | B.54 | C.11 |
| 1.2288 | B.55 | C.11 |
| 1.2289 | B.56 | C.11 |
| 1.2290 | B.57 | C.11 |
| 1.2291 | B.58. | C.11 |
| 1.2292 | B.59 | C.11 |

TABLE 1-continued

| comp. no. | herbicide B | safener C |
|---|---|---|
| 1.2293 | B.60 | C.11 |
| 1.2294 | B.61 | C.11 |
| 1.2295 | B.62 | C.11 |
| 1.2296 | B.63 | C.11 |
| 1.2297 | B.64 | C.11 |
| 1.2298 | B.65 | C.11 |
| 1.2299 | B.66 | C.11 |
| 1.2300 | B.67 | C.11 |
| 1.2301 | B.68 | C.11 |
| 1.2302 | B.69 | C.11 |
| 1.2303 | B.70 | C.11 |
| 1.2304 | B.71 | C.11 |
| 1.2305 | B.72 | C.11 |
| 1.2306 | B.73 | C.11 |
| 1.2307 | B.74 | C.11 |
| 1.2308 | B.75 | C.11 |
| 1.2309 | B.76 | C.11 |
| 1.2310 | B.77 | C.11 |
| 1.2311 | B.78 | C.11 |
| 1.2312 | B.79 | C.11 |
| 1.2313 | B.80 | C.11 |
| 1.2314 | B.81 | C.11 |
| 1.2315 | B.82 | C.11 |
| 1.2316 | B.83 | C.11 |
| 1.2317 | B.84 | C.11 |
| 1.2318 | B.85 | C.11 |
| 1.2319 | B.86 | C.11 |
| 1.2320 | B.87 | C.11 |
| 1.2321 | B.88 | C.11 |
| 1.2322 | B.89 | C.11 |
| 1.2323 | B.90 | C.11 |
| 1.2324 | B.91 | C.11 |
| 1.2325 | B.92 | C.11 |
| 1.2326 | B.93 | C.11 |
| 1.2327 | B.94 | C.11 |
| 1.2328 | B.95 | C.11 |
| 1.2329 | B.96 | C.11 |
| 1.2330 | B.97 | C.11 |
| 1.2331 | B.98 | C.11 |
| 1.2332 | B.99 | C.11 |
| 1.2333 | B.100 | C.11 |
| 1.2334 | B.101 | C.11 |
| 1.2335 | B.102 | C.11 |
| 1.2336 | B.103 | C.11 |
| 1.2337 | B.104 | C.11 |
| 1.2338 | B.105 | C.11 |
| 1.2339 | B.106 | C.11 |
| 1.2340 | B.107 | C.11 |
| 1.2341 | B.108 | C.11 |
| 1.2342 | B.109 | C.11 |
| 1.2343 | B.110 | C.11 |
| 1.2344 | B.111 | C.11 |
| 1.2345 | B.112 | C.11 |
| 1.2346 | B.113 | C.11 |
| 1.2347 | B.114 | C.11 |
| 1.2348 | B.115 | C.11 |
| 1.2349 | B.116 | C.11 |
| 1.2350 | B.117 | C.11 |
| 1.2351 | B.118 | C.11 |
| 1.2352 | B.119 | C.11 |
| 1.2353 | B.120 | C.11 |
| 1.2354 | B.121 | C.11 |
| 1.2355 | B.122 | C.11 |
| 1.2356 | B.123 | C.11 |
| 1.2357 | B.124 | C.11 |
| 1.2358 | B.125 | C.11 |
| 1.2359 | B.126 | C.11 |
| 1.2360 | B.127 | C.11 |
| 1.2361 | B.128 | C.11 |
| 1.2362 | B.129 | C.11 |
| 1.2363 | B.130 | C.11 |
| 1.2364 | B.131 | C.11 |
| 1.2365 | B.132 | C.11 |
| 1.2366 | B.133 | C.11 |
| 1.2367 | B.134 | C.11 |
| 1.2368 | B.135 | C.11 |
| 1.2369 | B.136 | C.11 |
| 1.2370 | B.137 | C.11 |
| 1.2371 | B.138 | C.11 |
| 1.2372 | B.139 | C.11 |
| 1.2373 | B.140 | C.11 |
| 1.2374 | B.141 | C.11 |
| 1.2375 | B.142 | C.11 |
| 1.2376 | B.143 | C.11 |
| 1.2377 | B.144 | C.11 |
| 1.2378 | B.145 | C.11 |
| 1.2379 | B.146 | C.11 |
| 1.2380 | B.147 | C.11 |
| 1.2381 | B.148 | C.11 |
| 1.2382 | B.149 | C.11 |
| 1.2383 | B.150 | C.11 |
| 1.2384 | B.151 | C.11 |
| 1.2385 | B.152 | C.11 |
| 1.2386 | B.153 | C.11 |
| 1.2387 | B.154 | C.11 |
| 1.2388 | B.155 | C.11 |
| 1.2389 | B.156 | C.11 |
| 1.2390 | B.157 | C.11 |
| 1.2391 | B.158 | C.11 |
| 1.2392 | B.159 | C.11 |
| 1.2393 | B.160 | C.11 |
| 1.2394 | B.161 | C.11 |
| 1.2395 | B.162 | C.11 |
| 1.2396 | B.163 | C.11 |
| 1.2397 | B.164 | C.11 |
| 1.2398 | B.165 | C.11 |
| 1.2399 | B.166 | C.11 |
| 1.2400 | B.167 | C.11 |
| 1.2401 | B.168 | C.11 |
| 1.2402 | B.169 | C.11 |
| 1.2403 | B.170 | C.11 |
| 1.2404 | B.171 | C.11 |
| 1.2405 | B.172 | C.11 |
| 1.2406 | B.173 | C.11 |
| 1.2407 | B.174 | C.11 |
| 1.2408 | B.175 | C.11 |
| 1.2409 | B.176 | C.11 |
| 1.2410 | B.177 | C.11 |
| 1.2411 | B.178 | C.11 |
| 1.2412 | B.179 | C.11 |
| 1.2413 | B.180 | C.11 |
| 1.2414 | B.181 | C.11 |
| 1.2415 | B.182 | C.11 |
| 1.2416 | B.183 | C.11 |
| 1.2417 | B.184 | C.11 |
| 1.2418 | B.185 | C.11 |
| 1.2419 | B.186 | C.11 |
| 1.2420 | B.187 | C.11 |
| 1.2421 | B.188 | C.11 |
| 1.2422 | B.189 | C.11 |
| 1.2423 | B.190 | C.11 |
| 1.2424 | B.191 | C.11 |
| 1.2425 | B.192 | C.11 |
| 1.2426 | B.193 | C.11 |
| 1.2427 | B.194 | C.11 |
| 1.2428 | B.195 | C.11 |
| 1.2429 | B.196 | C.11 |
| 1.2430 | B.197 | C.11 |
| 1.2431 | B.198 | C.11 |
| 1.2432 | B.199 | C.11 |
| 1.2433 | B.200 | C.11 |
| 1.2434 | B.201 | C.11 |
| 1.2435 | B.202 | C.11 |
| 1.2436 | B.203 | C.11 |
| 1.2437 | B.1 | C.12 |
| 1.2438 | B.2 | C.12 |
| 1.2439 | B.3 | C.12 |
| 1.2440 | B.4 | C.12 |
| 1.2441 | B.5 | C.12 |
| 1.2442 | B.6 | C.12 |
| 1.2443 | B.7 | C.12 |
| 1.2444 | B.8 | C.12 |
| 1.2445 | B.9 | C.12 |
| 1.2446 | B.10 | C.12 |
| 1.2447 | B.11 | C.12 |
| 1.2448 | B.12 | C.12 |

TABLE 1-continued

| comp. no. | herbicide B | safener C |
|---|---|---|
| 1.2449 | B.13 | C.12 |
| 1.2450 | B.14 | C.12 |
| 1.2451 | B.15 | C.12 |
| 1.2452 | B.16 | C.12 |
| 1.2453 | B.17 | C.12 |
| 1.2454 | B.18 | C.12 |
| 1.2455 | B.19 | C.12 |
| 1.2456 | B.20 | C.12 |
| 1.2457 | B.21 | C.12 |
| 1.2458 | B.22 | C.12 |
| 1.2459 | B.23 | C.12 |
| 1.2460 | B.24 | C.12 |
| 1.2461 | B.25 | C.12 |
| 1.2462 | B.26 | C.12 |
| 1.2463 | B.27 | C.12 |
| 1.2464 | B.28 | C.12 |
| 1.2465 | B.29 | C.12 |
| 1.2466 | B.30 | C.12 |
| 1.2467 | B.31 | C.12 |
| 1.2468 | B.32 | C.12 |
| 1.2469 | B.33 | C.12 |
| 1.2470 | B.34 | C.12 |
| 1.2471 | B.35 | C.12 |
| 1.2472 | B.36 | C.12 |
| 1.2473 | B.37 | C.12 |
| 1.2474 | B.38 | C.12 |
| 1.2475 | B.39 | C.12 |
| 1.2476 | B.40 | C.12 |
| 1.2477 | B.41 | C.12 |
| 1.2478 | B.42 | C.12 |
| 1.2479 | B.43 | C.12 |
| 1.2480 | B.44 | C.12 |
| 1.2481 | B.45 | C.12 |
| 1.2482 | B.46 | C.12 |
| 1.2483 | B.47 | C.12 |
| 1.2484 | B.48 | C.12 |
| 1.2485 | B.49 | C.12 |
| 1.2486 | B.50 | C.12 |
| 1.2487 | B.51 | C.12 |
| 1.2488 | B.52 | C.12 |
| 1.2489 | B.53 | C.12 |
| 1.2490 | B.54 | C.12 |
| 1.2491 | B.55 | C.12 |
| 1.2492 | B.56 | C.12 |
| 1.2493 | B.57 | C.12 |
| 1.2494 | B.58. | C.12 |
| 1.2495 | B.59 | C.12 |
| 1.2496 | B.60 | C.12 |
| 1.2497 | B.61 | C.12 |
| 1.2498 | B.62 | C.12 |
| 1.2499 | B.63 | C.12 |
| 1.2500 | B.64 | C.12 |
| 1.2501 | B.65 | C.12 |
| 1.2502 | B.66 | C.12 |
| 1.2503 | B.67 | C.12 |
| 1.2504 | B.68 | C.12 |
| 1.2505 | B.69 | C.12 |
| 1.2506 | B.70 | C.12 |
| 1.2507 | B.71 | C.12 |
| 1.2508 | B.72 | C.12 |
| 1.2509 | B.73 | C.12 |
| 1.2510 | B.74 | C.12 |
| 1.2511 | B.75 | C.12 |
| 1.2512 | B.76 | C.12 |
| 1.2513 | B.77 | C.12 |
| 1.2514 | B.78 | C.12 |
| 1.2515 | B.79 | C.12 |
| 1.2516 | B.80 | C.12 |
| 1.2517 | B.81 | C.12 |
| 1.2518 | B.82 | C.12 |
| 1.2519 | B.83 | C.12 |
| 1.2520 | B.84 | C.12 |
| 1.2521 | B.85 | C.12 |
| 1.2522 | B.86 | C.12 |
| 1.2523 | B.87 | C.12 |
| 1.2524 | B.88 | C.12 |
| 1.2525 | B.89 | C.12 |
| 1.2526 | B.90 | C.12 |
| 1.2527 | B.91 | C.12 |
| 1.2528 | B.92 | C.12 |
| 1.2529 | B.93 | C.12 |
| 1.2530 | B.94 | C.12 |
| 1.2531 | B.95 | C.12 |
| 1.2532 | B.96 | C.12 |
| 1.2533 | B.97 | C.12 |
| 1.2534 | B.98 | C.12 |
| 1.2535 | B.99 | C.12 |
| 1.2536 | B.100 | C.12 |
| 1.2537 | B.101 | C.12 |
| 1.2538 | B.102 | C.12 |
| 1.2539 | B.103 | C.12 |
| 1.2540 | B.104 | C.12 |
| 1.2541 | B.105 | C.12 |
| 1.2542 | B.106 | C.12 |
| 1.2543 | B.107 | C.12 |
| 1.2544 | B.108 | C.12 |
| 1.2545 | B.109 | C.12 |
| 1.2546 | B.110 | C.12 |
| 1.2547 | B.111 | C.12 |
| 1.2548 | B.112 | C.12 |
| 1.2549 | B.113 | C.12 |
| 1.2550 | B.114 | C.12 |
| 1.2551 | B.115 | C.12 |
| 1.2552 | B.116 | C.12 |
| 1.2553 | B.117 | C.12 |
| 1.2554 | B.118 | C.12 |
| 1.2555 | B.119 | C.12 |
| 1.2556 | B.120 | C.12 |
| 1.2557 | B.121 | C.12 |
| 1.2558 | B.122 | C.12 |
| 1.2559 | B.123 | C.12 |
| 1.2560 | B.124 | C.12 |
| 1.2561 | B.125 | C.12 |
| 1.2562 | B.126 | C.12 |
| 1.2563 | B.127 | C.12 |
| 1.2564 | B.128 | C.12 |
| 1.2565 | B.129 | C.12 |
| 1.2566 | B.130 | C.12 |
| 1.2567 | B.131 | C.12 |
| 1.2568 | B.132 | C.12 |
| 1.2569 | B.133 | C.12 |
| 1.2570 | B.134 | C.12 |
| 1.2571 | B.135 | C.12 |
| 1.2572 | B.136 | C.12 |
| 1.2573 | B.137 | C.12 |
| 1.2574 | B.138 | C.12 |
| 1.2575 | B.139 | C.12 |
| 1.2576 | B.140 | C.12 |
| 1.2577 | B.141 | C.12 |
| 1.2578 | B.142 | C.12 |
| 1.2579 | B.143 | C.12 |
| 1.2580 | B.144 | C.12 |
| 1.2581 | B.145 | C.12 |
| 1.2582 | B.146 | C.12 |
| 1.2583 | B.147 | C.12 |
| 1.2584 | B.148 | C.12 |
| 1.2585 | B.149 | C.12 |
| 1.2586 | B.150 | C.12 |
| 1.2587 | B.151 | C.12 |
| 1.2588 | B.152 | C.12 |
| 1.2589 | B.153 | C.12 |
| 1.2590 | B.154 | C.12 |
| 1.2591 | B.155 | C.12 |
| 1.2592 | B.156 | C.12 |
| 1.2593 | B.157 | C.12 |
| 1.2594 | B.158 | C.12 |
| 1.2595 | B.159 | C.12 |
| 1.2596 | B.160 | C.12 |
| 1.2597 | B.161 | C.12 |
| 1.2598 | B.162 | C.12 |
| 1.2599 | B.163 | C.12 |
| 1.2600 | B.164 | C.12 |
| 1.2601 | B.165 | C.12 |
| 1.2602 | B.166 | C.12 |
| 1.2603 | B.167 | C.12 |
| 1.2604 | B.168 | C.12 |

TABLE 1-continued

| comp. no. | herbicide B | safener C |
|---|---|---|
| 1.2605 | B.169 | C.12 |
| 1.2606 | B.170 | C.12 |
| 1.2607 | B.171 | C.12 |
| 1.2608 | B.172 | C.12 |
| 1.2609 | B.173 | C.12 |
| 1.2610 | B.174 | C.12 |
| 1.2611 | B.175 | C.12 |
| 1.2612 | B.176 | C.12 |
| 1.2613 | B.177 | C.12 |
| 1.2614 | B.178 | C.12 |
| 1.2615 | B.179 | C.12 |
| 1.2616 | B.180 | C.12 |
| 1.2617 | B.181 | C.12 |
| 1.2618 | B.182 | C.12 |
| 1.2619 | B.183 | C.12 |
| 1.2620 | B.184 | C.12 |
| 1.2621 | B.185 | C.12 |
| 1.2622 | B.186 | C.12 |
| 1.2623 | B.187 | C.12 |
| 1.2624 | B.188 | C.12 |
| 1.2625 | B.189 | C.12 |
| 1.2626 | B.190 | C.12 |
| 1.2627 | B.191 | C.12 |
| 1.2628 | B.192 | C.12 |
| 1.2629 | B.193 | C.12 |
| 1.2630 | B.194 | C.12 |
| 1.2631 | B.195 | C.12 |
| 1.2632 | B.196 | C.12 |
| 1.2633 | B.197 | C.12 |
| 1.2634 | B.198 | C.12 |
| 1.2635 | B.199 | C.12 |
| 1.2636 | B.200 | C.12 |
| 1.2637 | B.201 | C.12 |
| 1.2638 | B.202 | C.12 |
| 1.2639 | B.203 | C.12 |
| 1.2640 | B.1 | C.13 |
| 1.2641 | B.2 | C.13 |
| 1.2642 | B.3 | C.13 |
| 1.2643 | B.4 | C.13 |
| 1.2644 | B.5 | C.13 |
| 1.2645 | B.6 | C.13 |
| 1.2646 | B.7 | C.13 |
| 1.2647 | B.8 | C.13 |
| 1.2648 | B.9 | C.13 |
| 1.2649 | B.10 | C.13 |
| 1.2650 | B.11 | C.13 |
| 1.2651 | B.12 | C.13 |
| 1.2652 | B.13 | C.13 |
| 1.2653 | B.14 | C.13 |
| 1.2654 | B.15 | C.13 |
| 1.2655 | B.16 | C.13 |
| 1.2656 | B.17 | C.13 |
| 1.2657 | B.18 | C.13 |
| 1.2658 | B.19 | C.13 |
| 1.2659 | B.20 | C.13 |
| 1.2660 | B.21 | C.13 |
| 1.2661 | B.22 | C.13 |
| 1.2662 | B.23 | C.13 |
| 1.2663 | B.24 | C.13 |
| 1.2664 | B.25 | C.13 |
| 1.2665 | B.26 | C.13 |
| 1.2666 | B.27 | C.13 |
| 1.2667 | B.28 | C.13 |
| 1.2668 | B.29 | C.13 |
| 1.2669 | B.30 | C.13 |
| 1.2670 | B.31 | C.13 |
| 1.2671 | B.32 | C.13 |
| 1.2672 | B.33 | C.13 |
| 1.2673 | B.34 | C.13 |
| 1.2674 | B.35 | C.13 |
| 1.2675 | B.36 | C.13 |
| 1.2676 | B.37 | C.13 |
| 1.2677 | B.38 | C.13 |
| 1.2678 | B.39 | C.13 |
| 1.2679 | B.40 | C.13 |
| 1.2680 | B.41 | C.13 |
| 1.2681 | B.42 | C.13 |
| 1.2682 | B.43 | C.13 |
| 1.2683 | B.44 | C.13 |
| 1.2684 | B.45 | C.13 |
| 1.2685 | B.46 | C.13 |
| 1.2686 | B.47 | C.13 |
| 1.2687 | B.48 | C.13 |
| 1.2688 | B.49 | C.13 |
| 1.2689 | B.50 | C.13 |
| 1.2690 | B.51 | C.13 |
| 1.2691 | B.52 | C.13 |
| 1.2692 | B.53 | C.13 |
| 1.2693 | B.54 | C.13 |
| 1.2694 | B.55 | C.13 |
| 1.2695 | B.56 | C.13 |
| 1.2696 | B.57 | C.13 |
| 1.2697 | B.58. | C.13 |
| 1.2698 | B.59 | C.13 |
| 1.2699 | B.60 | C.13 |
| 1.2700 | B.61 | C.13 |
| 1.2701 | B.62 | C.13 |
| 1.2702 | B.63 | C.13 |
| 1.2703 | B.64 | C.13 |
| 1.2704 | B.65 | C.13 |
| 1.2705 | B.66 | C.13 |
| 1.2706 | B.67 | C.13 |
| 1.2707 | B.68 | C.13 |
| 1.2708 | B.69 | C.13 |
| 1.2709 | B.70 | C.13 |
| 1.2710 | B.71 | C.13 |
| 1.2711 | B.72 | C.13 |
| 1.2712 | B.73 | C.13 |
| 1.2713 | B.74 | C.13 |
| 1.2714 | B.75 | C.13 |
| 1.2715 | B.76 | C.13 |
| 1.2716 | B.77 | C.13 |
| 1.2717 | B.78 | C.13 |
| 1.2718 | B.79 | C.13 |
| 1.2719 | B.80 | C.13 |
| 1.2720 | B.81 | C.13 |
| 1.2721 | B.82 | C.13 |
| 1.2722 | B.83 | C.13 |
| 1.2723 | B.84 | C.13 |
| 1.2724 | B.85 | C.13 |
| 1.2725 | B.86 | C.13 |
| 1.2726 | B.87 | C.13 |
| 1.2727 | B.88 | C.13 |
| 1.2728 | B.89 | C.13 |
| 1.2729 | B.90 | C.13 |
| 1.2730 | B.91 | C.13 |
| 1.2731 | B.92 | C.13 |
| 1.2732 | B.93 | C.13 |
| 1.2733 | B.94 | C.13 |
| 1.2734 | B.95 | C.13 |
| 1.2735 | B.96 | C.13 |
| 1.2736 | B.97 | C.13 |
| 1.2737 | B.98 | C.13 |
| 1.2738 | B.99 | C.13 |
| 1.2739 | B.100 | C.13 |
| 1.2740 | B.101 | C.13 |
| 1.2741 | B.102 | C.13 |
| 1.2742 | B.103 | C.13 |
| 1.2743 | B.104 | C.13 |
| 1.2744 | B.105 | C.13 |
| 1.2745 | B.106 | C.13 |
| 1.2746 | B.107 | C.13 |
| 1.2747 | B.108 | C.13 |
| 1.2748 | B.109 | C.13 |
| 1.2749 | B.110 | C.13 |
| 1.2750 | B.111 | C.13 |
| 1.2751 | B.112 | C.13 |
| 1.2752 | B.113 | C.13 |
| 1.2753 | B.114 | C.13 |
| 1.2754 | B.115 | C.13 |
| 1.2755 | B.116 | C.13 |
| 1.2756 | B.117 | C.13 |
| 1.2757 | B.118 | C.13 |
| 1.2758 | B.119 | C.13 |
| 1.2759 | B.120 | C.13 |
| 1.2760 | B.121 | C.13 |

TABLE 1-continued

| comp. no. | herbicide B | safener C |
|---|---|---|
| 1.2761 | B.122 | C.13 |
| 1.2762 | B.123 | C.13 |
| 1.2763 | B.124 | C.13 |
| 1.2764 | B.125 | C.13 |
| 1.2765 | B.126 | C.13 |
| 1.2766 | B.127 | C.13 |
| 1.2767 | B.128 | C.13 |
| 1.2768 | B.129 | C.13 |
| 1.2769 | B.130 | C.13 |
| 1.2770 | B.131 | C.13 |
| 1.2771 | B.132 | C.13 |
| 1.2772 | B.133 | C.13 |
| 1.2773 | B.134 | C.13 |
| 1.2774 | B.135 | C.13 |
| 1.2775 | B.136 | C.13 |
| 1.2776 | B.137 | C.13 |
| 1.2777 | B.138 | C.13 |
| 1.2778 | B.139 | C.13 |
| 1.2779 | B.140 | C.13 |
| 1.2780 | B.141 | C.13 |
| 1.2781 | B.142 | C.13 |
| 1.2782 | B.143 | C.13 |
| 1.2783 | B.144 | C.13 |
| 1.2784 | B.145 | C.13 |
| 1.2785 | B.146 | C.13 |
| 1.2786 | B.147 | C.13 |
| 1.2787 | B.148 | C.13 |
| 1.2788 | B.149 | C.13 |
| 1.2789 | B.150 | C.13 |
| 1.2790 | B.151 | C.13 |
| 1.2791 | B.152 | C.13 |
| 1.2792 | B.153 | C.13 |
| 1.2793 | B.154 | C.13 |
| 1.2794 | B.155 | C.13 |
| 1.2795 | B.156 | C.13 |
| 1.2796 | B.157 | C.13 |
| 1.2797 | B.158 | C.13 |
| 1.2798 | B.159 | C.13 |
| 1.2799 | B.160 | C.13 |
| 1.2800 | B.161 | C.13 |
| 1.2801 | B.162 | C.13 |
| 1.2802 | B.163 | C.13 |
| 1.2803 | B.164 | C.13 |
| 1.2804 | B.165 | C.13 |
| 1.2805 | B.166 | C.13 |
| 1.2806 | B.167 | C.13 |
| 1.2807 | B.168 | C.13 |
| 1.2808 | B.169 | C.13 |
| 1.2809 | B.170 | C.13 |
| 1.2810 | B.171 | C.13 |
| 1.2811 | B.172 | C.13 |
| 1.2812 | B.173 | C.13 |
| 1.2813 | B.174 | C.13 |
| 1.2814 | B.175 | C.13 |
| 1.2815 | B.176 | C.13 |
| 1.2816 | B.177 | C.13 |
| 1.2817 | B.178 | C.13 |
| 1.2818 | B.179 | C.13 |
| 1.2819 | B.180 | C.13 |
| 1.2820 | B.181 | C.13 |
| 1.2821 | B.182 | C.13 |
| 1.2822 | B.183 | C.13 |
| 1.2823 | B.184 | C.13 |
| 1.2824 | B.185 | C.13 |
| 1.2825 | B.186 | C.13 |
| 1.2826 | B.187 | C.13 |
| 1.2827 | B.188 | C.13 |
| 1.2828 | B.189 | C.13 |
| 1.2829 | B.190 | C.13 |
| 1.2830 | B.191 | C.13 |
| 1.2831 | B.192 | C.13 |
| 1.2832 | B.193 | C.13 |
| 1.2833 | B.194 | C.13 |
| 1.2834 | B.195 | C.13 |
| 1.2835 | B.196 | C.13 |
| 1.2836 | B.197 | C.13 |
| 1.2837 | B.198 | C.13 |
| 1.2838 | B.199 | C.13 |
| 1.2839 | B.200 | C.13 |
| 1.2840 | B.201 | C.13 |
| 1.2841 | B.202 | C.13 |
| 1.2842 | B.203 | C.13 |
| 1.2843 | B.1 | C.14 |
| 1.2844 | B.2 | C.14 |
| 1.2845 | B.3 | C.14 |
| 1.2846 | B.4 | C.14 |
| 1.2847 | B.5 | C.14 |
| 1.2848 | B.6 | C.14 |
| 1.2849 | B.7 | C.14 |
| 1.2850 | B.8 | C.14 |
| 1.2851 | B.9 | C.14 |
| 1.2852 | B.10 | C.14 |
| 1.2853 | B.11 | C.14 |
| 1.2854 | B.12 | C.14 |
| 1.2855 | B.13 | C.14 |
| 1.2856 | B.14 | C.14 |
| 1.2857 | B.15 | C.14 |
| 1.2858 | B.16 | C.14 |
| 1.2859 | B.17 | C.14 |
| 1.2860 | B.18 | C.14 |
| 1.2861 | B.19 | C.14 |
| 1.2862 | B.20 | C.14 |
| 1.2863 | B.21 | C.14 |
| 1.2864 | B.22 | C.14 |
| 1.2865 | B.23 | C.14 |
| 1.2866 | B.24 | C.14 |
| 1.2867 | B.25 | C.14 |
| 1.2868 | B.26 | C.14 |
| 1.2869 | B.27 | C.14 |
| 1.2870 | B.28 | C.14 |
| 1.2871 | B.29 | C.14 |
| 1.2872 | B.30 | C.14 |
| 1.2873 | B.31 | C.14 |
| 1.2874 | B.32 | C.14 |
| 1.2875 | B.33 | C.14 |
| 1.2876 | B.34 | C.14 |
| 1.2877 | B.35 | C.14 |
| 1.2878 | B.36 | C.14 |
| 1.2879 | B.37 | C.14 |
| 1.2880 | B.38 | C.14 |
| 1.2881 | B.39 | C.14 |
| 1.2882 | B.40 | C.14 |
| 1.2883 | B.41 | C.14 |
| 1.2884 | B.42 | C.14 |
| 1.2885 | B.43 | C.14 |
| 1.2886 | B.44 | C.14 |
| 1.2887 | B.45 | C.14 |
| 1.2888 | B.46 | C.14 |
| 1.2889 | B.47 | C.14 |
| 1.2890 | B.48 | C.14 |
| 1.2891 | B.49 | C.14 |
| 1.2892 | B.50 | C.14 |
| 1.2893 | B.51 | C.14 |
| 1.2894 | B.52 | C.14 |
| 1.2895 | B.53 | C.14 |
| 1.2896 | B.54 | C.14 |
| 1.2897 | B.55 | C.14 |
| 1.2898 | B.56 | C.14 |
| 1.2899 | B.57 | C.14 |
| 1.2900 | B.58. | C.14 |
| 1.2901 | B.59 | C.14 |
| 1.2902 | B.60 | C.14 |
| 1.2903 | B.61 | C.14 |
| 1.2904 | B.62 | C.14 |
| 1.2905 | B.63 | C.14 |
| 1.2906 | B.64 | C.14 |
| 1.2907 | B.65 | C.14 |
| 1.2908 | B.66 | C.14 |
| 1.2909 | B.67 | C.14 |
| 1.2910 | B.68 | C.14 |
| 1.2911 | B.69 | C.14 |
| 1.2912 | B.70 | C.14 |
| 1.2913 | B.71 | C.14 |
| 1.2914 | B.72 | C.14 |
| 1.2915 | B.73 | C.14 |
| 1.2916 | B.74 | C.14 |

TABLE 1-continued

| comp. no. | herbicide B | safener C |
|---|---|---|
| 1.2917 | B.75 | C.14 |
| 1.2918 | B.76 | C.14 |
| 1.2919 | B.77 | C.14 |
| 1.2920 | B.78 | C.14 |
| 1.2921 | B.79 | C.14 |
| 1.2922 | B.80 | C.14 |
| 1.2923 | B.81 | C.14 |
| 1.2924 | B.82 | C.14 |
| 1.2925 | B.83 | C.14 |
| 1.2926 | B.84 | C.14 |
| 1.2927 | B.85 | C.14 |
| 1.2928 | B.86 | C.14 |
| 1.2929 | B.87 | C.14 |
| 1.2930 | B.88 | C.14 |
| 1.2931 | B.89 | C.14 |
| 1.2932 | B.90 | C.14 |
| 1.2933 | B.91 | C.14 |
| 1.2934 | B.92 | C.14 |
| 1.2935 | B.93 | C.14 |
| 1.2936 | B.94 | C.14 |
| 1.2937 | B.95 | C.14 |
| 1.2938 | B.96 | C.14 |
| 1.2939 | B.97 | C.14 |
| 1.2940 | B.98 | C.14 |
| 1.2941 | B.99 | C.14 |
| 1.2942 | B.100 | C.14 |
| 1.2943 | B.101 | C.14 |
| 1.2944 | B.102 | C.14 |
| 1.2945 | B.103 | C.14 |
| 1.2946 | B.104 | C.14 |
| 1.2947 | B.105 | C.14 |
| 1.2948 | B.106 | C.14 |
| 1.2949 | B.107 | C.14 |
| 1.2950 | B.108 | C.14 |
| 1.2951 | B.109 | C.14 |
| 1.2952 | B.110 | C.14 |
| 1.2953 | B.111 | C.14 |
| 1.2954 | B.112 | C.14 |
| 1.2955 | B.113 | C.14 |
| 1.2956 | B.114 | C.14 |
| 1.2957 | B.115 | C.14 |
| 1.2958 | B.116 | C.14 |
| 1.2959 | B.117 | C.14 |
| 1.2960 | B.118 | C.14 |
| 1.2961 | B.119 | C.14 |
| 1.2962 | B.120 | C.14 |
| 1.2963 | B.121 | C.14 |
| 1.2964 | B.122 | C.14 |
| 1.2965 | B.123 | C.14 |
| 1.2966 | B.124 | C.14 |
| 1.2967 | B.125 | C.14 |
| 1.2968 | B.126 | C.14 |
| 1.2969 | B.127 | C.14 |
| 1.2970 | B.128 | C.14 |
| 1.2971 | B.129 | C.14 |
| 1.2972 | B.130 | C.14 |
| 1.2973 | B.131 | C.14 |
| 1.2974 | B.132 | C.14 |
| 1.2975 | B.133 | C.14 |
| 1.2976 | B.134 | C.14 |
| 1.2977 | B.135 | C.14 |
| 1.2978 | B.136 | C.14 |
| 1.2979 | B.137 | C.14 |
| 1.2980 | B.138 | C.14 |
| 1.2981 | B.139 | C.14 |
| 1.2982 | B.140 | C.14 |
| 1.2983 | B.141 | C.14 |
| 1.2984 | B.142 | C.14 |
| 1.2985 | B.143 | C.14 |
| 1.2986 | B.144 | C.14 |
| 1.2987 | B.145 | C.14 |
| 1.2988 | B.146 | C.14 |
| 1.2989 | B.147 | C.14 |
| 1.2990 | B.148 | C.14 |
| 1.2991 | B.149 | C.14 |
| 1.2992 | B.150 | C.14 |
| 1.2993 | B.151 | C.14 |
| 1.2994 | B.152 | C.14 |
| 1.2995 | B.153 | C.14 |
| 1.2996 | B.154 | C.14 |
| 1.2997 | B.155 | C.14 |
| 1.2998 | B.156 | C.14 |
| 1.2999 | B.157 | C.14 |
| 1.3000 | B.158 | C.14 |
| 1.3001 | B.159 | C.14 |
| 1.3002 | B.160 | C.14 |
| 1.3003 | B.161 | C.14 |
| 1.3004 | B.162 | C.14 |
| 1.3005 | B.163 | C.14 |
| 1.3006 | B.164 | C.14 |
| 1.3007 | B.165 | C.14 |
| 1.3008 | B.166 | C.14 |
| 1.3009 | B.167 | C.14 |
| 1.3010 | B.168 | C.14 |
| 1.3011 | B.169 | C.14 |
| 1.3012 | B.170 | C.14 |
| 1.3013 | B.171 | C.14 |
| 1.3014 | B.172 | C.14 |
| 1.3015 | B.173 | C.14 |
| 1.3016 | B.174 | C.14 |
| 1.3017 | B.175 | C.14 |
| 1.3018 | B.176 | C.14 |
| 1.3019 | B.177 | C.14 |
| 1.3020 | B.178 | C.14 |
| 1.3021 | B.179 | C.14 |
| 1.3022 | B.180 | C.14 |
| 1.3023 | B.181 | C.14 |
| 1.3024 | B.182 | C.14 |
| 1.3025 | B.183 | C.14 |
| 1.3026 | B.184 | C.14 |
| 1.3027 | B.185 | C.14 |
| 1.3028 | B.186 | C.14 |
| 1.3029 | B.187 | C.14 |
| 1.3030 | B.188 | C.14 |
| 1.3031 | B.189 | C.14 |
| 1.3032 | B.190 | C.14 |
| 1.3033 | B.191 | C.14 |
| 1.3034 | B.192 | C.14 |
| 1.3035 | B.193 | C.14 |
| 1.3036 | B.194 | C.14 |
| 1.3037 | B.195 | C.14 |
| 1.3038 | B.196 | C.14 |
| 1.3039 | B.197 | C.14 |
| 1.3040 | B.198 | C.14 |
| 1.3041 | B.199 | C.14 |
| 1.3042 | B.200 | C.14 |
| 1.3043 | B.201 | C.14 |
| 1.3044 | B.202 | C.14 |
| 1.3045 | B.203 | C.14 |
| 1.3046 | B.1 | C.15 |
| 1.3047 | B.2 | C.15 |
| 1.3048 | B.3 | C.15 |
| 1.3049 | B.4 | C.15 |
| 1.3050 | B.5 | C.15 |
| 1.3051 | B.6 | C.15 |
| 1.3052 | B.7 | C.15 |
| 1.3053 | B.8 | C.15 |
| 1.3054 | B.9 | C.15 |
| 1.3055 | B.10 | C.15 |
| 1.3056 | B.11 | C.15 |
| 1.3057 | B.12 | C.15 |
| 1.3058 | B.13 | C.15 |
| 1.3059 | B.14 | C.15 |
| 1.3060 | B.15 | C.15 |
| 1.3061 | B.16 | C.15 |
| 1.3062 | B.17 | C.15 |
| 1.3063 | B.18 | C.15 |
| 1.3064 | B.19 | C.15 |
| 1.3065 | B.20 | C.15 |
| 1.3066 | B.21 | C.15 |
| 1.3067 | B.22 | C.15 |
| 1.3068 | B.23 | C.15 |
| 1.3069 | B.24 | C.15 |
| 1.3070 | B.25 | C.15 |
| 1.3071 | B.26 | C.15 |
| 1.3072 | B.27 | C.15 |

TABLE 1-continued

| comp. no. | herbicide B | safener C |
|---|---|---|
| 1.3073 | B.28 | C.15 |
| 1.3074 | B.29 | C.15 |
| 1.3075 | B.30 | C.15 |
| 1.3076 | B.31 | C.15 |
| 1.3077 | B.32 | C.15 |
| 1.3078 | B.33 | C.15 |
| 1.3079 | B.34 | C.15 |
| 1.3080 | B.35 | C.15 |
| 1.3081 | B.36 | C.15 |
| 1.3082 | B.37 | C.15 |
| 1.3083 | B.38 | C.15 |
| 1.3084 | B.39 | C.15 |
| 1.3085 | B.40 | C.15 |
| 1.3086 | B.41 | C.15 |
| 1.3087 | B.42 | C.15 |
| 1.3088 | B.43 | C.15 |
| 1.3089 | B.44 | C.15 |
| 1.3090 | B.45 | C.15 |
| 1.3091 | B.46 | C.15 |
| 1.3092 | B.47 | C.15 |
| 1.3093 | B.48 | C.15 |
| 1.3094 | B.49 | C.15 |
| 1.3095 | B.50 | C.15 |
| 1.3096 | B.51 | C.15 |
| 1.3097 | B.52 | C.15 |
| 1.3098 | B.53 | C.15 |
| 1.3099 | B.54 | C.15 |
| 1.3100 | B.55 | C.15 |
| 1.3101 | B.56 | C.15 |
| 1.3102 | B.57 | C.15 |
| 1.3103 | B.58. | C.15 |
| 1.3104 | B.59 | C.15 |
| 1.3105 | B.60 | C.15 |
| 1.3106 | B.61 | C.15 |
| 1.3107 | B.62 | C.15 |
| 1.3108 | B.63 | C.15 |
| 1.3109 | B.64 | C.15 |
| 1.3110 | B.65 | C.15 |
| 1.3111 | B.66 | C.15 |
| 1.3112 | B.67 | C.15 |
| 1.3113 | B.68 | C.15 |
| 1.3114 | B.69 | C.15 |
| 1.3115 | B.70 | C.15 |
| 1.3116 | B.71 | C.15 |
| 1.3117 | B.72 | C.15 |
| 1.3118 | B.73 | C.15 |
| 1.3119 | B.74 | C.15 |
| 1.3120 | B.75 | C.15 |
| 1.3121 | B.76 | C.15 |
| 1.3122 | B.77 | C.15 |
| 1.3123 | B.78 | C.15 |
| 1.3124 | B.79 | C.15 |
| 1.3125 | B.80 | C.15 |
| 1.3126 | B.81 | C.15 |
| 1.3127 | B.82 | C.15 |
| 1.3128 | B.83 | C.15 |
| 1.3129 | B.84 | C.15 |
| 1.3130 | B.85 | C.15 |
| 1.3131 | B.86 | C.15 |
| 1.3132 | B.87 | C.15 |
| 1.3133 | B.88 | C.15 |
| 1.3134 | B.89 | C.15 |
| 1.3135 | B.90 | C.15 |
| 1.3136 | B.91 | C.15 |
| 1.3137 | B.92 | C.15 |
| 1.3138 | B.93 | C.15 |
| 1.3139 | B.94 | C.15 |
| 1.3140 | B.95 | C.15 |
| 1.3141 | B.96 | C.15 |
| 1.3142 | B.97 | C.15 |
| 1.3143 | B.98 | C.15 |
| 1.3144 | B.99 | C.15 |
| 1.3145 | B.100 | C.15 |
| 1.3146 | B.101 | C.15 |
| 1.3147 | B.102 | C.15 |
| 1.3148 | B.103 | C.15 |
| 1.3149 | B.104 | C.15 |
| 1.3150 | B.105 | C.15 |
| 1.3151 | B.106 | C.15 |
| 1.3152 | B.107 | C.15 |
| 1.3153 | B.108 | C.15 |
| 1.3154 | B.109 | C.15 |
| 1.3155 | B.110 | C.15 |
| 1.3156 | B.111 | C.15 |
| 1.3157 | B.112 | C.15 |
| 1.3158 | B.113 | C.15 |
| 1.3159 | B.114 | C.15 |
| 1.3160 | B.115 | C.15 |
| 1.3161 | B.116 | C.15 |
| 1.3162 | B.117 | C.15 |
| 1.3163 | B.118 | C.15 |
| 1.3164 | B.119 | C.15 |
| 1.3165 | B.120 | C.15 |
| 1.3166 | B.121 | C.15 |
| 1.3167 | B.122 | C.15 |
| 1.3168 | B.123 | C.15 |
| 1.3169 | B.124 | C.15 |
| 1.3170 | B.125 | C.15 |
| 1.3171 | B.126 | C.15 |
| 1.3172 | B.127 | C.15 |
| 1.3173 | B.128 | C.15 |
| 1.3174 | B.129 | C.15 |
| 1.3175 | B.130 | C.15 |
| 1.3176 | B.131 | C.15 |
| 1.3177 | B.132 | C.15 |
| 1.3178 | B.133 | C.15 |
| 1.3179 | B.134 | C.15 |
| 1.3180 | B.135 | C.15 |
| 1.3181 | B.136 | C.15 |
| 1.3182 | B.137 | C.15 |
| 1.3183 | B.138 | C.15 |
| 1.3184 | B.139 | C.15 |
| 1.3185 | B.140 | C.15 |
| 1.3186 | B.141 | C.15 |
| 1.3187 | B.142 | C.15 |
| 1.3188 | B.143 | C.15 |
| 1.3189 | B.144 | C.15 |
| 1.3190 | B.145 | C.15 |
| 1.3191 | B.146 | C.15 |
| 1.3192 | B.147 | C.15 |
| 1.3193 | B.148 | C.15 |
| 1.3194 | B.149 | C.15 |
| 1.3195 | B.150 | C.15 |
| 1.3196 | B.151 | C.15 |
| 1.3197 | B.152 | C.15 |
| 1.3198 | B.153 | C.15 |
| 1.3199 | B.154 | C.15 |
| 1.3200 | B.155 | C.15 |
| 1.3201 | B.156 | C.15 |
| 1.3202 | B.157 | C.15 |
| 1.3203 | B.158 | C.15 |
| 1.3204 | B.159 | C.15 |
| 1.3205 | B.160 | C.15 |
| 1.3206 | B.161 | C.15 |
| 1.3207 | B.162 | C.15 |
| 1.3208 | B.163 | C.15 |
| 1.3209 | B.164 | C.15 |
| 1.3210 | B.165 | C.15 |
| 1.3211 | B.166 | C.15 |
| 1.3212 | B.167 | C.15 |
| 1.3213 | B.168 | C.15 |
| 1.3214 | B.169 | C.15 |
| 1.3215 | B.170 | C.15 |
| 1.3216 | B.171 | C.15 |
| 1.3217 | B.172 | C.15 |
| 1.3218 | B.173 | C.15 |
| 1.3219 | B.174 | C.15 |
| 1.3220 | B.175 | C.15 |
| 1.3221 | B.176 | C.15 |
| 1.3222 | B.177 | C.15 |
| 1.3223 | B.178 | C.15 |
| 1.3224 | B.179 | C.15 |
| 1.3225 | B.180 | C.15 |
| 1.3226 | B.181 | C.15 |
| 1.3227 | B.182 | C.15 |
| 1.3228 | B.183 | C.15 |

TABLE 1-continued

| comp. no. | herbicide B | safener C |
| --- | --- | --- |
| 1.3229 | B.184 | C.15 |
| 1.3230 | B.185 | C.15 |
| 1.3231 | B.186 | C.15 |
| 1.3232 | B.187 | C.15 |
| 1.3233 | B.188 | C.15 |
| 1.3234 | B.189 | C.15 |
| 1.3235 | B.190 | C.15 |
| 1.3236 | B.191 | C.15 |
| 1.3237 | B.192 | C.15 |
| 1.3238 | B.193 | C.15 |
| 1.3239 | B.194 | C.15 |
| 1.3240 | B.195 | C.15 |
| 1.3241 | B.196 | C.15 |
| 1.3242 | B.197 | C.15 |
| 1.3243 | B.198 | C.15 |
| 1.3244 | B.199 | C.15 |
| 1.3245 | B.200 | C.15 |
| 1.3246 | B.201 | C.15 |
| 1.3247 | B.202 | C.15 |
| 1.3248 | B.203 | C.15 |
| 1.3249 | B.1 | C.16 |
| 1.3250 | B.2 | C.16 |
| 1.3251 | B.3 | C.16 |
| 1.3252 | B.4 | C.16 |
| 1.3253 | B.5 | C.16 |
| 1.3254 | B.6 | C.16 |
| 1.3255 | B.7 | C.16 |
| 1.3256 | B.8 | C.16 |
| 1.3257 | B.9 | C.16 |
| 1.3258 | B.10 | C.16 |
| 1.3259 | B.11 | C.16 |
| 1.3260 | B.12 | C.16 |
| 1.3261 | B.13 | C.16 |
| 1.3262 | B.14 | C.16 |
| 1.3263 | B.15 | C.16 |
| 1.3264 | B.16 | C.16 |
| 1.3265 | B.17 | C.16 |
| 1.3266 | B.18 | C.16 |
| 1.3267 | B.19 | C.16 |
| 1.3268 | B.20 | C.16 |
| 1.3269 | B.21 | C.16 |
| 1.3270 | B.22 | C.16 |
| 1.3271 | B.23 | C.16 |
| 1.3272 | B.24 | C.16 |
| 1.3273 | B.25 | C.16 |
| 1.3274 | B.26 | C.16 |
| 1.3275 | B.27 | C.16 |
| 1.3276 | B.28 | C.16 |
| 1.3277 | B.29 | C.16 |
| 1.3278 | B.30 | C.16 |
| 1.3279 | B.31 | C.16 |
| 1.3280 | B.32 | C.16 |
| 1.3281 | B.33 | C.16 |
| 1.3282 | B.34 | C.16 |
| 1.3283 | B.35 | C.16 |
| 1.3284 | B.36 | C.16 |
| 1.3285 | B.37 | C.16 |
| 1.3286 | B.38 | C.16 |
| 1.3287 | B.39 | C.16 |
| 1.3288 | B.40 | C.16 |
| 1.3289 | B.41 | C.16 |
| 1.3290 | B.42 | C.16 |
| 1.3291 | B.43 | C.16 |
| 1.3292 | B.44 | C.16 |
| 1.3293 | B.45 | C.16 |
| 1.3294 | B.46 | C.16 |
| 1.3295 | B.47 | C.16 |
| 1.3296 | B.48 | C.16 |
| 1.3297 | B.49 | C.16 |
| 1.3298 | B.50 | C.16 |
| 1.3299 | B.51 | C.16 |
| 1.3300 | B.52 | C.16 |
| 1.3301 | B.53 | C.16 |
| 1.3302 | B.54 | C.16 |
| 1.3303 | B.55 | C.16 |
| 1.3304 | B.56 | C.16 |
| 1.3305 | B.57 | C.16 |
| 1.3306 | B.58. | C.16 |
| 1.3307 | B.59 | C.16 |
| 1.3308 | B.60 | C.16 |
| 1.3309 | B.61 | C.16 |
| 1.3310 | B.62 | C.16 |
| 1.3311 | B.63 | C.16 |
| 1.3312 | B.64 | C.16 |
| 1.3313 | B.65 | C.16 |
| 1.3314 | B.66 | C.16 |
| 1.3315 | B.67 | C.16 |
| 1.3316 | B.68 | C.16 |
| 1.3317 | B.69 | C.16 |
| 1.3318 | B.70 | C.16 |
| 1.3319 | B.71 | C.16 |
| 1.3320 | B.72 | C.16 |
| 1.3321 | B.73 | C.16 |
| 1.3322 | B.74 | C.16 |
| 1.3323 | B.75 | C.16 |
| 1.3324 | B.76 | C.16 |
| 1.3325 | B.77 | C.16 |
| 1.3326 | B.78 | C.16 |
| 1.3327 | B.79 | C.16 |
| 1.3328 | B.80 | C.16 |
| 1.3329 | B.81 | C.16 |
| 1.3330 | B.82 | C.16 |
| 1.3331 | B.83 | C.16 |
| 1.3332 | B.84 | C.16 |
| 1.3333 | B.85 | C.16 |
| 1.3334 | B.86 | C.16 |
| 1.3335 | B.87 | C.16 |
| 1.3336 | B.88 | C.16 |
| 1.3337 | B.89 | C.16 |
| 1.3338 | B.90 | C.16 |
| 1.3339 | B.91 | C.16 |
| 1.3340 | B.92 | C.16 |
| 1.3341 | B.93 | C.16 |
| 1.3342 | B.94 | C.16 |
| 1.3343 | B.95 | C.16 |
| 1.3344 | B.96 | C.16 |
| 1.3345 | B.97 | C.16 |
| 1.3346 | B.98 | C.16 |
| 1.3347 | B.99 | C.16 |
| 1.3348 | B.100 | C.16 |
| 1.3349 | B.101 | C.16 |
| 1.3350 | B.102 | C.16 |
| 1.3351 | B.103 | C.16 |
| 1.3352 | B.104 | C.16 |
| 1.3353 | B.105 | C.16 |
| 1.3354 | B.106 | C.16 |
| 1.3355 | B.107 | C.16 |
| 1.3356 | B.108 | C.16 |
| 1.3357 | B.109 | C.16 |
| 1.3358 | B.110 | C.16 |
| 1.3359 | B.111 | C.16 |
| 1.3360 | B.112 | C.16 |
| 1.3361 | B.113 | C.16 |
| 1.3362 | B.114 | C.16 |
| 1.3363 | B.115 | C.16 |
| 1.3364 | B.116 | C.16 |
| 1.3365 | B.117 | C.16 |
| 1.3366 | B.118 | C.16 |
| 1.3367 | B.119 | C.16 |
| 1.3368 | B.120 | C.16 |
| 1.3369 | B.121 | C.16 |
| 1.3370 | B.122 | C.16 |
| 1.3371 | B.123 | C.16 |
| 1.3372 | B.124 | C.16 |
| 1.3373 | B.125 | C.16 |
| 1.3374 | B.126 | C.16 |
| 1.3375 | B.127 | C.16 |
| 1.3376 | B.128 | C.16 |
| 1.3377 | B.129 | C.16 |
| 1.3378 | B.130 | C.16 |
| 1.3379 | B.131 | C.16 |
| 1.3380 | B.132 | C.16 |
| 1.3381 | B.133 | C.16 |
| 1.3382 | B.134 | C.16 |
| 1.3383 | B.135 | C.16 |
| 1.3384 | B.136 | C.16 |

TABLE 1-continued

| comp. no. | herbicide B | safener C |
|---|---|---|
| 1.3385 | B.137 | C.16 |
| 1.3386 | B.138 | C.16 |
| 1.3387 | B.139 | C.16 |
| 1.3388 | B.140 | C.16 |
| 1.3389 | B.141 | C.16 |
| 1.3390 | B.142 | C.16 |
| 1.3391 | B.143 | C.16 |
| 1.3392 | B.144 | C.16 |
| 1.3393 | B.145 | C.16 |
| 1.3394 | B.146 | C.16 |
| 1.3395 | B.147 | C.16 |
| 1.3396 | B.148 | C.16 |
| 1.3397 | B.149 | C.16 |
| 1.3398 | B.150 | C.16 |
| 1.3399 | B.151 | C.16 |
| 1.3400 | B.152 | C.16 |
| 1.3401 | B.153 | C.16 |
| 1.3402 | B.154 | C.16 |
| 1.3403 | B.155 | C.16 |
| 1.3404 | B.156 | C.16 |
| 1.3405 | B.157 | C.16 |
| 1.3406 | B.158 | C.16 |
| 1.3407 | B.159 | C.16 |
| 1.3408 | B.160 | C.16 |
| 1.3409 | B.161 | C.16 |
| 1.3410 | B.162 | C.16 |
| 1.3411 | B.163 | C.16 |
| 1.3412 | B.164 | C.16 |
| 1.3413 | B.165 | C.16 |
| 1.3414 | B.166 | C.16 |
| 1.3415 | B.167 | C.16 |
| 1.3416 | B.168 | C.16 |
| 1.3417 | B.169 | C.16 |
| 1.3418 | B.170 | C.16 |
| 1.3419 | B.171 | C.16 |
| 1.3420 | B.172 | C.16 |
| 1.3421 | B.173 | C.16 |
| 1.3422 | B.174 | C.16 |
| 1.3423 | B.175 | C.16 |
| 1.3424 | B.176 | C.16 |
| 1.3425 | B.177 | C.16 |
| 1.3426 | B.178 | C.16 |
| 1.3427 | B.179 | C.16 |
| 1.3428 | B.180 | C.16 |
| 1.3429 | B.181 | C.16 |
| 1.3430 | B.182 | C.16 |
| 1.3431 | B.183 | C.16 |
| 1.3432 | B.184 | C.16 |
| 1.3433 | B.185 | C.16 |
| 1.3434 | B.186 | C.16 |
| 1.3435 | B.187 | C.16 |
| 1.3436 | B.188 | C.16 |
| 1.3437 | B.189 | C.16 |
| 1.3438 | B.190 | C.16 |
| 1.3439 | B.191 | C.16 |
| 1.3440 | B.192 | C.16 |
| 1.3441 | B.193 | C.16 |
| 1.3442 | B.194 | C.16 |
| 1.3443 | B.195 | C.16 |
| 1.3444 | B.196 | C.16 |
| 1.3445 | B.197 | C.16 |
| 1.3446 | B.198 | C.16 |
| 1.3447 | B.199 | C.16 |
| 1.3448 | B.200 | C.16 |
| 1.3449 | B.201 | C.16 |
| 1.3450 | B.202 | C.16 |
| 1.3451 | B.203 | C.16 |
| 1.3452 | B.1 | C.17 |
| 1.3453 | B.2 | C.17 |
| 1.3454 | B.3 | C.17 |
| 1.3455 | B.4 | C.17 |
| 1.3456 | B.5 | C.17 |
| 1.3457 | B.6 | C.17 |
| 1.3458 | B.7 | C.17 |
| 1.3459 | B.8 | C.17 |
| 1.3460 | B.9 | C.17 |
| 1.3461 | B.10 | C.17 |
| 1.3462 | B.11 | C.17 |
| 1.3463 | B.12 | C.17 |
| 1.3464 | B.13 | C.17 |
| 1.3465 | B.14 | C.17 |
| 1.3466 | B.15 | C.17 |
| 1.3467 | B.16 | C.17 |
| 1.3468 | B.17 | C.17 |
| 1.3469 | B.18 | C.17 |
| 1.3470 | B.19 | C.17 |
| 1.3471 | B.20 | C.17 |
| 1.3472 | B.21 | C.17 |
| 1.3473 | B.22 | C.17 |
| 1.3474 | B.23 | C.17 |
| 1.3475 | B.24 | C.17 |
| 1.3476 | B.25 | C.17 |
| 1.3477 | B.26 | C.17 |
| 1.3478 | B.27 | C.17 |
| 1.3479 | B.28 | C.17 |
| 1.3480 | B.29 | C.17 |
| 1.3481 | B.30 | C.17 |
| 1.3482 | B.31 | C.17 |
| 1.3483 | B.32 | C.17 |
| 1.3484 | B.33 | C.17 |
| 1.3485 | B.34 | C.17 |
| 1.3486 | B.35 | C.17 |
| 1.3487 | B.36 | C.17 |
| 1.3488 | B.37 | C.17 |
| 1.3489 | B.38 | C.17 |
| 1.3490 | B.39 | C.17 |
| 1.3491 | B.40 | C.17 |
| 1.3492 | B.41 | C.17 |
| 1.3493 | B.42 | C.17 |
| 1.3494 | B.43 | C.17 |
| 1.3495 | B.44 | C.17 |
| 1.3496 | B.45 | C.17 |
| 1.3497 | B.46 | C.17 |
| 1.3498 | B.47 | C.17 |
| 1.3499 | B.48 | C.17 |
| 1.3500 | B.49 | C.17 |
| 1.3501 | B.50 | C.17 |
| 1.3502 | B.51 | C.17 |
| 1.3503 | B.52 | C.17 |
| 1.3504 | B.53 | C.17 |
| 1.3505 | B.54 | C.17 |
| 1.3506 | B.55 | C.17 |
| 1.3507 | B.56 | C.17 |
| 1.3508 | B.57 | C.17 |
| 1.3509 | B.58. | C.17 |
| 1.3510 | B.59 | C.17 |
| 1.3511 | B.60 | C.17 |
| 1.3512 | B.61 | C.17 |
| 1.3513 | B.62 | C.17 |
| 1.3514 | B.63 | C.17 |
| 1.3515 | B.64 | C.17 |
| 1.3516 | B.65 | C.17 |
| 1.3517 | B.66 | C.17 |
| 1.3518 | B.67 | C.17 |
| 1.3519 | B.68 | C.17 |
| 1.3520 | B.69 | C.17 |
| 1.3521 | B.70 | C.17 |
| 1.3522 | B.71 | C.17 |
| 1.3523 | B.72 | C.17 |
| 1.3524 | B.73 | C.17 |
| 1.3525 | B.74 | C.17 |
| 1.3526 | B.75 | C.17 |
| 1.3527 | B.76 | C.17 |
| 1.3528 | B.77 | C.17 |
| 1.3529 | B.78 | C.17 |
| 1.3530 | B.79 | C.17 |
| 1.3531 | B.80 | C.17 |
| 1.3532 | B.81 | C.17 |
| 1.3533 | B.82 | C.17 |
| 1.3534 | B.83 | C.17 |
| 1.3535 | B.84 | C.17 |
| 1.3536 | B.85 | C.17 |
| 1.3537 | B.86 | C.17 |
| 1.3538 | B.87 | C.17 |
| 1.3539 | B.88 | C.17 |
| 1.3540 | B.89 | C.17 |

TABLE 1-continued

| comp. no. | herbicide B | safener C |
|---|---|---|
| 1.3541 | B.90 | C.17 |
| 1.3542 | B.91 | C.17 |
| 1.3543 | B.92 | C.17 |
| 1.3544 | B.93 | C.17 |
| 1.3545 | B.94 | C.17 |
| 1.3546 | B.95 | C.17 |
| 1.3547 | B.96 | C.17 |
| 1.3548 | B.97 | C.17 |
| 1.3549 | B.98 | C.17 |
| 1.3550 | B.99 | C.17 |
| 1.3551 | B.100 | C.17 |
| 1.3552 | B.101 | C.17 |
| 1.3553 | B.102 | C.17 |
| 1.3554 | B.103 | C.17 |
| 1.3555 | B.104 | C.17 |
| 1.3556 | B.105 | C.17 |
| 1.3557 | B.106 | C.17 |
| 1.3558 | B.107 | C.17 |
| 1.3559 | B.108 | C.17 |
| 1.3560 | B.109 | C.17 |
| 1.3561 | B.110 | C.17 |
| 1.3562 | B.111 | C.17 |
| 1.3563 | B.112 | C.17 |
| 1.3564 | B.113 | C.17 |
| 1.3565 | B.114 | C.17 |
| 1.3566 | B.115 | C.17 |
| 1.3567 | B.116 | C.17 |
| 1.3568 | B.117 | C.17 |
| 1.3569 | B.118 | C.17 |
| 1.3570 | B.119 | C.17 |
| 1.3571 | B.120 | C.17 |
| 1.3572 | B.121 | C.17 |
| 1.3573 | B.122 | C.17 |
| 1.3574 | B.123 | C.17 |
| 1.3575 | B.124 | C.17 |
| 1.3576 | B.125 | C.17 |
| 1.3577 | B.126 | C.17 |
| 1.3578 | B.127 | C.17 |
| 1.3579 | B.128 | C.17 |
| 1.3580 | B.129 | C.17 |
| 1.3581 | B.130 | C.17 |
| 1.3582 | B.131 | C.17 |
| 1.3583 | B.132 | C.17 |
| 1.3584 | B.133 | C.17 |
| 1.3585 | B.134 | C.17 |
| 1.3586 | B.135 | C.17 |
| 1.3587 | B.136 | C.17 |
| 1.3588 | B.137 | C.17 |
| 1.3589 | B.138 | C.17 |
| 1.3590 | B.139 | C.17 |
| 1.3591 | B.140 | C.17 |
| 1.3592 | B.141 | C.17 |
| 1.3593 | B.142 | C.17 |
| 1.3594 | B.143 | C.17 |
| 1.3595 | B.144 | C.17 |
| 1.3596 | B.145 | C.17 |
| 1.3597 | B.146 | C.17 |
| 1.3598 | B.147 | C.17 |
| 1.3599 | B.148 | C.17 |
| 1.3600 | B.149 | C.17 |
| 1.3601 | B.150 | C.17 |
| 1.3602 | B.151 | C.17 |
| 1.3603 | B.152 | C.17 |
| 1.3604 | B.153 | C.17 |
| 1.3605 | B.154 | C.17 |
| 1.3606 | B.155 | C.17 |
| 1.3607 | B.156 | C.17 |
| 1.3608 | B.157 | C.17 |
| 1.3609 | B.158 | C.17 |
| 1.3610 | B.159 | C.17 |
| 1.3611 | B.160 | C.17 |
| 1.3612 | B.161 | C.17 |
| 1.3613 | B.162 | C.17 |
| 1.3614 | B.163 | C.17 |
| 1.3615 | B.164 | C.17 |
| 1.3616 | B.165 | C.17 |
| 1.3617 | B.166 | C.17 |
| 1.3618 | B.167 | C.17 |
| 1.3619 | B.168 | C.17 |
| 1.3620 | B.169 | C.17 |
| 1.3621 | B.170 | C.17 |
| 1.3622 | B.171 | C.17 |
| 1.3623 | B.172 | C.17 |
| 1.3624 | B.173 | C.17 |
| 1.3625 | B.174 | C.17 |
| 1.3626 | B.175 | C.17 |
| 1.3627 | B.176 | C.17 |
| 1.3628 | B.177 | C.17 |
| 1.3629 | B.178 | C.17 |
| 1.3630 | B.179 | C.17 |
| 1.3631 | B.180 | C.17 |
| 1.3632 | B.181 | C.17 |
| 1.3633 | B.182 | C.17 |
| 1.3634 | B.183 | C.17 |
| 1.3635 | B.184 | C.17 |
| 1.3636 | B.185 | C.17 |
| 1.3637 | B.186 | C.17 |
| 1.3638 | B.187 | C.17 |
| 1.3639 | B.188 | C.17 |
| 1.3640 | B.189 | C.17 |
| 1.3641 | B.190 | C.17 |
| 1.3642 | B.191 | C.17 |
| 1.3643 | B.192 | C.17 |
| 1.3644 | B.193 | C.17 |
| 1.3645 | B.194 | C.17 |
| 1.3646 | B.195 | C.17 |
| 1.3647 | B.196 | C.17 |
| 1.3648 | B.197 | C.17 |
| 1.3649 | B.198 | C.17 |
| 1.3650 | B.199 | C.17 |
| 1.3651 | B.200 | C.17 |
| 1.3652 | B.201 | C.17 |
| 1.3653 | B.202 | C.17 |
| 1.3654 | B.203 | C.17 |
| 1.3655 | — | C.1 |
| 1.3656 | — | C.2 |
| 1.3657 | — | C.3 |
| 1.3658 | — | C.4 |
| 1.3659 | — | C.5 |
| 1.3660 | — | C.6 |
| 1.3661 | — | C.7 |
| 1.3662 | — | C.8 |
| 1.3663 | — | C.9 |
| 1.3664 | — | C.10 |
| 1.3665 | — | C.11 |
| 1.3666 | — | C.12 |
| 1.3667 | — | C.13 |
| 1.3668 | — | C.14 |
| 1.3669 | — | C.15 |
| 1.3670 | — | C.16 |
| 1.3671 | — | C.17 |

It may furthermore be beneficial to apply the diaminotriazine compounds of formula (I) alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

The invention also relates to agrochemical compositions comprising at least an auxiliary and at least one diaminotriazine compound of formula (I) according to the invention.

An agrochemical composition comprises a pesticidally effective amount of a diaminotriazine compound of formula (I). The term "effective amount" denotes an amount of the composition or of the compounds I, which is sufficient for controlling unwanted plants, especially for controlling unwanted plants in cultivated plants and which does not result in a substantial damage to the treated plants. Such an amount can vary in a broad range and is dependent on various factors, such as the plants to be controlled, the treated cultivated plant or material, the climatic conditions and the specific diaminotriazine compound of formula (I) used.

The diaminotriazine compound of formula (I), their N-oxides or salts can be converted into customary types of agrochemical compositions, e. g. solutions, emulsions, suspensions, dusts, powders, pastes, granules, pressings, capsules, and mixtures thereof. Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, $6^{th}$ Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetaines and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneimines.

Suitable adjuvants are compounds, which have a neglectable or even no pesticidally activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for agrochemical composition types and their preparation are:

i) Water-soluble concentrates (SL, LS)

10-60 wt % of an diaminotriazine compound of formula (I) according to the invention and 5-278 wt % wetting agent (e.g. alcohol alkoxylates) are dissolved in water and/or in a water-soluble solvent (e.g. alcohols) ad 100 wt %. The active substance dissolves upon dilution with water.

ii) Dispersible concentrates (DC)

5-25 wt % of an diaminotriazine compound of formula (I) according to the invention and 1-10 wt % dispersant (e. g. polyvinylpyrrolidone) are dissolved in organic solvent (e.g. cyclohexanone) ad 100 wt %. Dilution with water gives a dispersion.

iii) Emulsifiable concentrates (EC)

278-70 wt % of an diaminotriazine compound of formula (I) according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of an diaminotriazine compound of formula (I) according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of an diaminotriazine compound of formula (I) according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-dispersible granules and water-soluble granules (WG, SG)

50-80 wt % of an diaminotriazine compound of formula (I) according to the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-dispersible powders and water-soluble powders (WP, SP, WS)

50-80 wt % of an diaminotriazine compound of formula (I) according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of an diaminotriazine compound of formula (I) according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of an diaminotriazine compound of formula (I) according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of an diaminotriazine compound of formula (I) according to the invention, 0-40 wt % water insoluble organic solvent (e.g. aromatic hydrocarbon), 2-278 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of an diaminotriazine compound of formula (I) according to the invention, 0-40 wt % water insoluble organic solvent (e.g. aromatic hydrocarbon), and an isocyanate monomer (e.g. diphenymethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable powders (DP, DS)

1-10 wt % of an diaminotriazine compound of formula (I) according to the invention are ground finely and mixed intimately with solid carrier (e.g. finely divided kaolin) ad 100 wt %.

x) Granules (GR, FG)

0.5-30 wt % of an diaminotriazine compound of formula (I) according to the invention is ground finely and associated with solid carrier (e.g. silicate) ad 100 wt %. Granulation is achieved by extrusion, spray-drying or the fluidized bed.

xi) Ultra-low volume liquids (UL)

1-50 wt % of an diaminotriazine compound of formula (I) according to the invention are dissolved in organic solvent (e.g. aromatic hydrocarbon) ad 100 wt %.

The agrochemical compositions types i) to xi) may optionally comprise further auxiliaries, such as 0.1-1 wt % bactericides, 5-278 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of the diaminotriazine compounds of formula (I). The diaminotriazine compounds of formula (I) are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The agrochemical compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying diaminotriazine compounds of formula (I) or agrochemical compositions thereof, on to plant propagation material, especially seeds, include dressing, coating, pelleting, dusting, soaking and in-furrow application methods of the propagation material. Preferably, compound I or the compositions thereof, respectively, are applied on to the plant propagation material by a method such that germination is not induced, e. g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the diaminotriazine compounds of formula (I) or the agrochemical compositions comprising them as premix or, if appropriate not until immediately prior to use (tank mix). These agents can be admixed with the agrochemical compositions according to the invention in a weight ratio of 1:100 to 100:1, preferably 1:10 to 10:1.

The user applies the diaminotriazine compounds of formula (I) according to the invention or the agrochemical compositions comprising them usually from a pre-dosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, either individual components of the agrochemical composition according to the invention or partially premixed components, e. g. components comprising azines of formula (I) may be mixed by the user in a spray tank and further auxiliaries and additives may be added, if appropriate.

In a further embodiment, individual components of the agrochemical composition according to the invention such as parts of a kit or parts of a binary or ternary mixture may be mixed by the user himself in a spray tank and further auxiliaries may be added, if appropriate.

In a further embodiment, either individual components of the agrochemical composition according to the invention or partially premixed components, e. g components comprising diaminotriazine compounds of formula (I), can be applied jointly (e.g. after tank mix) or consecutively.

The diaminotriazine compounds of formula (I), are suitable as herbicides. They are suitable as such or as an appropriately formulated composition (agrochemical composition).

The diaminotriazine compounds of formula (I), or the agrochemical compositions comprising the azines of formula (I), control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

The diaminotriazine compounds of formula (I), or the agrochemical compositions comprising them, are applied to the plants mainly by spraying the leaves or are applied to the soil in which the plant seeds have been sown. Here, the application can be carried out using, for example, water as carrier by customary spraying techniques using spray liquor amounts of from about 100 to 1000 I/ha (for example from 300 to 400 I/ha). The diaminotriazine compounds of formula (I), or the agrochemical compositions comprising them, may also be applied by the low-volume or the ultra-low-volume method, or in the form of microgranules.

Application of the diaminotriazine compounds of formula (I), or the agrochemical compositions comprising them, can be done before, during and/or after the emergence of the undesirable plants.

The diaminotriazine compounds of formula (I), or the agrochemical compositions comprising them, can be applied pre-, post-emergence or pre-plant, or together with the seed of a crop plant. It is also possible to apply the diaminotriazine compounds of formula (I), or the agrochemical compositions comprising them, by applying seed, pretreated with the diaminotriazine compounds of formula (I), or the agrochemical compositions comprising them, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the diaminotriazine compounds of formula (I), or the agrochemical compositions comprising them, can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the diaminotriazine compounds of formula (I), or the agrochemical compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

When employed in plant protection, the amounts of active substances applied, i.e. the diaminotriazine compounds of formula (I), without formulation auxiliaries, are, depending on the kind of effect desired, from 0.001 to 2 kg per ha, preferably from 0.005 to 2 kg per ha, more preferably from 0.005 to 0.9 kg per ha and in particular from 0.05 to 0.5 kg per ha.

In another embodiment of the invention, the application rate of the diaminotriazine compounds of formula (I) is from 0.001 to 3 kg/ha, preferably from 0.005 to 2.5 kg/ha, of active substance (a.s.).

In another preferred embodiment of the invention, the rates of application of the diaminotriazine compounds of formula (I) according to the present invention (total amount of diaminotriazine compounds of formula (I)) are from 0.1 g/ha to 3000 g/ha, preferably 10 g/ha to 1000 g/ha, depending on the control target, the season, the target plants and the growth stage.

In another preferred embodiment of the invention, the application rates of the diaminotriazine compounds of formula (I) are in the range from 0.1 g/ha to 5000 g/ha and preferably in the range from 1 g/ha to 2500 g/ha or from 5 g/ha to 2000 g/ha.

In another preferred embodiment of the invention, the application rate of the diaminotriazine compounds of formula (I) is 0.1 to 1000 g/ha, preferably 1 to 750 g/ha, more preferably 5 to 500 g/ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

In another embodiment of the invention, to treat the seed, the amounts of active substances applied, i.e. the diaminotriazine compounds of formula (I) are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Depending on the application method in question, the diaminotriazine compounds of formula (I), or the agrochemical compositions comprising them, can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor (s. vulgare), Theobroma cacao, Trifolium pratense, Triticum aestivum, Triticale, Triticum durum, Vicia faba, Vitis vinifera* and *Zea mays.*

Preferred crops are *Arachis hypogaea, Beta vulgaris* spec. *altissima, Brassica napus* var. *napus, Brassica oleracea, Citrus limon, Citrus sinensis, Coffea arabica (Coffea canephora, Coffea liberica), Cynodon dactylon, Glycine max, Gossypium hirsutum, (Gossypium arboreum, Gossypium herbaceum, Gossypium vitifolium), Helianthus annuus, Hordeum vulgare, Juglans regia, Lens culinaris, Linum usitatissimum, Lycopersicon lycopersicum, Malus* spec., *Medicago sativa, Nicotiana tabacum (N. rustica), Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor (s. vulgare), Triticale, Triticum aestivum, Triticum durum, Vicia faba, Vitis vinifera* and *Zea mays.*

Especially preferred crops are crops of cereals, corn, soybeans, rice, oilseed rape, cotton, potatoes, peanuts or permanent crops.

The diaminotriazine compounds of formula (I) according to the invention, or the agrochemical compositions comprising them, can also be used in genetically modified plants.

The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e. g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e. g., Clearfield® summer rape (Canola, BASF SE, Germany) being tolerant to imidazolinones, e. g., imazamox, or ExpressSun® sunflowers (DuPont, USA) being tolerant to sulfonyl ureas, e. g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as delta-endotoxins, e. g., CryIA(b), CryIA(c), CryIF, CryIF(a2), CryIIA(b), CryIIIA, CryIIIB(b) or Cry9c; vegetative insecticidal proteins (VIP), e. g., VIP1, VIP2, VIP3 or VIP3A; insecticidal proteins of bacteria colonizing nematodes, e. g., *Photorhabdus* spp. or *Xenorhabdus* spp.; toxins produced by animals, such as scorpion toxins, arachnid toxins, wasp toxins, or other insect-specific neurotoxins; toxins produced by fungi, such as Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e. g., WO 02/0278701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g., in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1 Ab toxin), YieldGard® Plus (corn cultivars producing Cry1Ab and Cry3Bb1 toxins), Starink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S. A., Belgium (corn cultivars producing the Cry3Bb1 toxin), IPC 531 from Monsanto Europe S. A., Belgium (cotton cultivars producing a modified version of the Cry1Ac toxin) and 27807 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e. g., potato culti-vars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modified plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e. g., oil crops that produce health-promoting long-chain omega-3 fatty acids or unsaturated omega-9 fatty acids (e. g., Nexera® rape, Dow Agro-Sciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

A further embodiment of the invention is a method of controlling undesired vegetation, which comprises allowing a herbicidally active amount of at least one compound of formula (I) and as defined above to act on plants, their environment or on seed.

The preparation of the diaminotriazine compounds of formula (I) is illustrated by examples; however, the subject matter of the present invention is not limited to the examples given.

The products shown below were characterized by the mass ([m/z]) or retention time (RT; [min.]) determined by HPLC-MS spectrometry.

HPLC-MS=high performance liquid chromatography-coupled mass spectrometry; HPLC column:

RP-18 column (Chromolith Speed ROD from Merck KgaA, Germany), 50*4.6 mm; mobile phase: acetonitrile+0.1% trifluoroacetic acid (TFA)/water+0.1% TFA using a gradient from 5:95 to 100:0 over 5 minutes at 40° C., flow rate 1.8 mVmin.

MS: quadrupole electrospray ionization, 80 V (positive mode).

The following abbreviations are used:

TFA: Trifluoroacetic acid

CH: Cyclohexane

EtOAc: Ethyl acetate

THF: Tetrahydrofurane

MeOH: Methanol

HPLC: High pressure chromatography

LC: Liquid chromatography

MS: Mass spectrometry

A PREPARATION EXAMPLES

Example 1: N4-(2-benzyloxy-6-fluoro-phenyl)-6-(1-methoxy-1-methyl-ethyl)-1,3,5-triazine-2,4-diamine Step 1: 1-Benzyloxy-3-fluoro-2-nitro-benzene

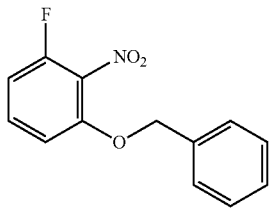 [SMILES: O=[N+]([O-])c1c(F)cccc1OCc1ccccc1]

K$_2$CO$_3$ (25.3 g, 183 mmol, 1.2 eq) was added to a solution of 3-fluoro-2-nitro-phenol (24.0 g, 153 mmol, 1.0 eq) in 100 ml DMF. Benzylbromide (26.1 g, 153 mmol, 1.0 eq) was added to the suspension at ambient temperature. The mixture was stirred for 18 h overnight. Water is added to the reaction mixture to dissolve any salts. The solution was extracted three times with 100 ml EtOAc. The combined organic layers were washed with water, dried with Na$_2$SO$_4$ and then evaporated. The solid residue was used without further purification in the following step.

LC/MS RT: 1.204. LC/MS (m/z): no ionization of the molecule observed $^1$H-NMR (400 MHz, CDCl$_3$) δ 5.2 (s, 2H), 6.8-6.9 (m, 2H), 7.3-7.4 (m, 6H)

Step 2: 2-Benzyloxy-6-fluoro-aniline

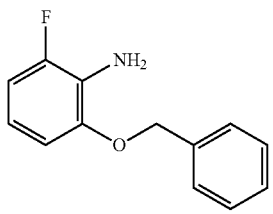 [SMILES: Nc1c(F)cccc1OCc1ccccc1]

Zinc powder (52.9 g, 809 mmol, 4.0 eq) was suspended in 400 ml acetic acid. 1-Benzyloxy-3-fluoro-2-nitro-benzene (50 g, 202 mmol, 1.0 eq) dissolved in 80 ml EtOAc was slowly added so that the temperature of the reaction mixture does not exceed 40° C. The mixture was stirred over the weekend at ambient temperature and then diluted with 300 ml EtOAc. After filtration, water was added. The organic layer was washed with a saturated NaHCO$_3$ solution and then evaporated. The crude material was purified over column chromatography (silica, cyclohexane/EtOAc) to obtain the desired product (29.7 g, 67% yield) as a light-yellow oil.

LC/MS RT: 1.051. LC/MS (m/z): 217.9 [M+H$^+$]

$^1$H-NMR (400 MHz, CDCl$_3$) δ 3.2-4.1 (br, 2H), 5.08 (s, 2H), 6.55-6.75 (m, 3H), 7.3-7.5 (m, 5H)

Step 3: 4-(1-methoxy-1-methyl-ethyl)-6-methylsulfanyl-1,3,5-triazin-2-amine

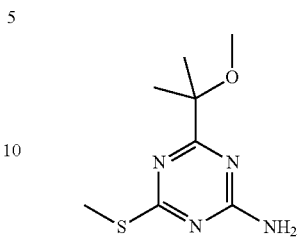

2-Methoxy-2-methyl-propanoic acid (5.4 g, 45.7 mmol, 1.01 eq) was dissolved in 10 ml CH$_2$C$_2$. After adding 3 drops of DMF, oxalyl dichloride 5.8 g, 45.7 mmol, 1.01 eq) was added at ambient temperature. After 1 h, when gas evolution is no longer observed, the solution is added slowly to a solution of 1-carbamimidoyl-2-methyl-isothiourea hydroiodide (11.8 g, 45.4 mmol, 1.0 eq) and triethylamine (13.78 g, 136 mmol, 3.0 eq) in 70 ml dioxane. After stirring at 60° C. for 4 h water and EtOAc were added. The organic phase was separated, dried over Na$_2$SO$_4$ and evaporated to give 9.4 g of crude product, which was used without further purification in the next step.

LC/MS RT: 0.742. LC/MS (m/z): 215.1 [M+H$^+$]

$^1$H-NMR (400 MHz, DMSO-d6) δ1.41 (d, 6H), 2.44 (s, 3H), 3.05 (s, 3H), 7.53 (d, 2H)

Step 4: 4-chloro-6-(1-methoxy-1-methyl-ethyl)-1,3,5-triazin-2-amine

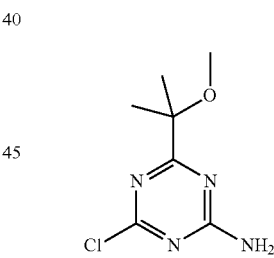

To a solution of 4-(1-methoxy-1-methyl-ethyl)-6-methylsulfanyl-1,3,5-triazin-2-amine (9.4 g, 43.9 mmol, 1.0 eq) in 100 ml EtOAc/CHCl$_3$, chlorine gas was introduced for 30 min at ambient temperature. Due to incomplete conversion of the starting material, chlorine gas was introduced for additional 30 minutes. After this period the solution was purged with N$_2$ gas and concentrated. The solid residue is treated with water and the precipitated solid was filtered and dried to give 5.7 g of the crude product that was used in the next step.

LC/MS RT: 0.736. LC/MS (m/z): 203.0 [M+H$^+$] 1.40 (s, 6H), 3.07 (s, 3H), 8.12, (d, 2H)

$^1$H-NMR (400 MHz, DMSO-d6) δ

Step 5: N4-(2-benzyloxy-6-fluoro-phenyl)-6-(1-methoxy-1-methyl-ethyl)-1,3,5-triazine-2,4-diamine

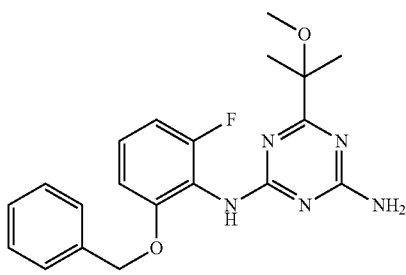 [SMILES: COC(C)(C)c1nc(N)nc(Nc2c(F)cccc2OCc2ccccc2)n1]

2-Benzyloxy-6-fluoro-aniline (400 mg, 1.8 mmol, 1.0 eq) and 4-chloro-6-(1-methoxy-1-methyl-ethyl)-1,3,5-triazin-2-amine (373 mg, 1.8 mmol, 1.0 eq) were suspended in 5 ml dioxane. Hydrogen chloride in dioxane (4.1 ml, 4.0 molar solution, 3.0 eq) was added and the mixture was heated to 90° C. for 2 h and then cooled to ambient temperature. After adding water and EtOAc the organic phase was separated, dried over $Na_2SO_4$ and evaporated to give the crude product, which was purified over column chromatography (silica, cyclohexane/EtOAc) to obtain the desired product (163 mg, 23% yield).

LC/MS RT: 0.921. LC/MS (m/z): 384.0 [M+H$^+$]
$^1$H-NMR (400 MHz, DMSO-d6) δ 2.5 (s, 6H), 3.3 (s, 3H), 5.1 (s, 2H), 6.75-6.9 (m, 3H), 6.93 (d, 1H), 7.15-7.35 (m, 6H)

Example 2: N4-(2-benzyloxy-6-fluoro-phenyl)-6-(1-fluoro-2-methyl-propyl)-1,3,5-triazine-2,4-diamine Step 1: 1-(2-Benzyloxy-6-fluoro-phenyl)-3-carbamimidoyl-guanidine hydrochloride

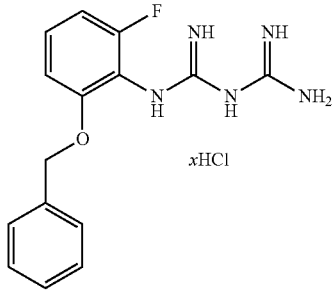 [SMILES: N=C(N)NC(=N)Nc1c(F)cccc1OCc1ccccc1]

2-Benzyloxy-6-fluoro-aniline (20 g, 92 mmol, 1.0 eq) and 1-cyanoguanidine (9.3 g, 110.5 mmol, 1.2 eq) were mixed in 150 ml acetonitrile. Hydrochloric acid (10.7 g, 37.5 wt-%, 1.2 eq) was added and the mixture was heated to 75° C. for 6 h. After cooling to ambient temperature, the precipitated solid was filtered and washed with acetonitrile and pentane. The solid was dried under vacuum to obtain 23.7 g of the HCl salt. The free base can be obtained by treatment with a sodium hydroxide solution and EtOAc extraction of the aqueous mixture.

LC/MS RT: 0.761. LC/MS (m/z): 301.9 [M+H$^+$]

Step 2: N4-(2-benzyloxy-6-fluoro-phenyl)-6-(1-fluoro-2-methyl-propyl)-1,3,5-triazine-2,4-diamine

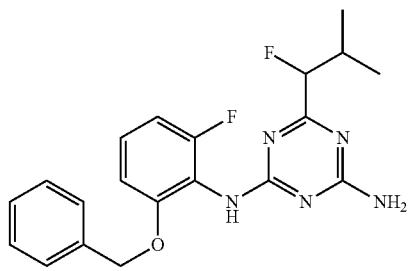 [SMILES: CC(C)C(F)c1nc(N)nc(Nc2c(F)cccc2OCc2ccccc2)n1]

2-Fluoro-3-methyl-butanoic acid (1.1 g, 9.31 mmol, 1.0 eq) was dissolved in 30 ml $CH_2Cl_2$. At −78° C. DAST (3.0 g, 18.6 mmol, 2.0 eq) was slowly added. After self-heating to ambient temperature overnight the mixture was added to a solution of 1-(2-benzyloxy-6-fluoro-phenyl)-3-carbamimidoyl-guanidine and triethylamine in 60 ml dioxane. The reaction mixture was stirred at 50° C. for 3 h. After cooling to ambient temperature, the mixture is poured onto water and extracted with additional $CH_2Cl_2$. After solvent evaporation, the crude product was purified over column chromatography (silica, cyclohexane/EtOAc) to obtain the desired product (45 mg, 1.3% yield) as a white solid.

LC/MS RT: 1.061. LC/MS (m/z): 385.9 [M+H$^+$]
$^1$H-NMR (500 MHz, DMSO-d6) 0.85 (b, 6H), 2.1-2.3 (b, 1H), 4.6-4.85 (d, 1H), 5.1 (s, 2H), 6.8-7.4 (m, 10H), 8.75 (b, 1H)

The compounds listed below in table 3 (examples 3 to 263) have been prepared similarly to the examples mentioned above:

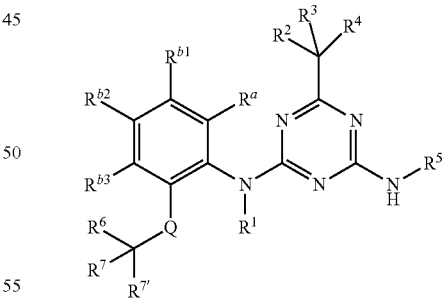

TABLE 3

| ex. no. | $R^2R^3R^4$ | $R^a$ | $R^{b1}$ | $R^{b2}$ | $R^{b3}$ | $R^6R^7R^{7'}$ | MS | HPLC |
|---|---|---|---|---|---|---|---|---|
| 3. | CFMe$_2$ | F | H | H | H | (3,5-dimethylphenyl)methyl | 1.131 | 399.9 |
| 4. | CFMe$_2$ | F | H | H | H | benzyl | 0.997 | 372.2 |
| 5. | 1-fluorocyclopentyl | F | H | H | H | benzyl | 1.051 | 398.1 |
| 6. | CFMe$_2$ | F | H | H | H | (4-fluorophenyl)methyl | 1.000 | 390.1 |
| 7. | CFMe$_2$ | F | H | H | H | (4-nitrophenyl)methyl | 0.979 | 417.1 |
| 8. | CFMe$_2$ | F | H | H | H | [4-(trifluoromethyl)phenyl]methyl | 1.082 | 440.1 |

TABLE 3-continued

| ex.no. | R²R³R⁴ | Rᵃ | R^{b1} | R^{b2} | R^{b3} | R⁶R⁷R⁷ | MS | HPLC |
|---|---|---|---|---|---|---|---|---|
| 9. | CFMe₂ | F | H | H | H | p-tolylmethyl | 1.04 | 386.1 |
| 10. | CFMe₂ | F | H | H | H | (3-methoxyphenyl)methyl | 0.993 | 402.1 |
| 11. | CFMe₂ | F | H | H | H | (3-fluorophenyl)methyl | 0.999 | 390.1 |
| 12. | 1-fluorocyclopentyl | F | H | H | H | (4-fluorophenyl)methyl | 1.035 | 416.1 |
| 13. | 1-fluorocyclopentyl | F | H | H | H | (4-nitrophenyl)methyl | 1.022 | 443.0 |
| 14. | 1-fluorocyclopentyl | F | H | H | H | (3-methoxyphenyl)methyl | 1.074 | 412.1 |
| 15. | 1-fluorocyclopentyl | F | H | H | H | p-tolylmethyl | 1.028 | 428.1 |
| 16. | 1-fluorocyclopentyl | F | H | H | H | (4-methoxyphenyl)methyl | 1.025 | 428.1 |
| 17. | 1-fluorocyclopentyl | F | H | H | H | [4-(trifluoromethyl)phenyl]methyl | 1.114 | 466.1 |
| 18. | 1-fluorocyclopentyl | F | H | H | H | (3-fluorophenyl)methyl | 1.035 | 416.1 |
| 19. | 1-fluorocyclopentyl | F | H | H | H | (2-fluorophenyl)methyl | 1.034 | 416.1 |
| 20. | CFMe₂ | F | H | H | H | (4-methoxyphenyl)methyl | 0.989 | 402.1 |
| 21. | CFMe₂ | F | H | H | H | 3-pyridylmethyl | 0.707 | 373.1 |
| 22. | CFMe₂ | F | H | H | H | 3-thienylmethyl | 0.961 | 378.1 |
| 23. | CFMe₂ | F | H | H | H | 1-phenylethyl | 1.023 | 386.2 |
| 24. | CFMe₂ | F | H | H | H | [3-(trifluoromethyl)phenyl]methyl | 1.061 | 440.1 |
| 25. | CFMe₂ | F | H | H | H | (3-nitrophenyl)methyl | 0.981 | 417.1 |
| 26. | CFMe₂ | F | H | H | H | m-tolylmethyl | 1.052 | 386.1 |
| 27. | CFMe₂ | F | H | H | H | (2-fluorophenyl)methyl | 1.007 | 390.0 |
| 28. | CFMe₂ | F | H | H | H | (2-nitrophenyl)methyl | 0.994 | 417.1 |
| 29. | CFMe₂ | F | H | H | H | [2-(trifluoromethyl)phenyl]methyl | 1.093 | 440.0 |
| 30. | CFMe₂ | F | H | H | H | o-tolylmethyl | 1.038 | 386.1 |
| 31. | 1-fluorocyclohexyl | F | H | H | H | benzyl | 1.092 | 412.1 |
| 32. | 1-methylcyclohexyl | F | H | H | H | benzyl | 1.064 | 408.1 |
| 33. | t-Bu | F | H | H | H | benzyl | 0.976 | 368.0 |
| 34. | 1-hydroxypropyl | F | H | H | H | benzyl | 0.882 | 370.0 |
| 35. | 1-fluoropropyl | F | H | H | H | benzyl | 1.013 | 372.0 |
| 36. | CFMe₂ | F | H | H | H | thiazol-2-ylmethyl | 0.862 | 379.0 |
| 37. | CFMe₂ | F | H | H | H | (2-methylthiazol-5-yl)methyl | 0.823 | 393.0 |
| 38. | CFMe₂ | F | H | H | H | (5-methoxycarbonyl-2-furyl)methyl | 0.912 | 420.0 |
| 39. | CFMe₂ | F | H | H | H | (2-chlorothiazol-5-yl)methyl | 1.035 | 412.0 |
| 40. | CFMe₂ | F | H | H | H | (3-methylisoxazol-5-yl)methyl | 0.871 | 377.0 |
| 41. | CFMe₂ | F | H | H | H | 1,3,4-oxadiazol-2-ylmethyl | 0.76 | 364 |
| 42. | CFMe₂ | F | H | H | H | (3-cyclopropyl-1,2,4-oxadiazol-5-yl)methyl | 0.926 | 404 |
| 43. | CFMe₂ | F | H | H | H | (3,5-difluorophenyl)methyl | 1.048 | 408 |
| 44. | CFMe₂ | F | H | H | H | (3-bromophenyl)methyl | 1.081 | 449.9 |
| 45. | CFMe₂ | F | H | H | H | (3,4-difluorophenyl)methyl | 1.008 | 408 |
| 46. | CFMe₂ | F | H | H | H | (3-iodophenyl)methyl | 1.058 | 497.9 |
| 47. | CFMe₂ | F | H | H | H | (3-chlorophenyl)methyl | 1.029 | 406 |
| 48. | CFMe₂ | F | H | H | H | (3-chloro-4-methoxy-phenyl)methyl | 1.056 | 435.9 |
| 49. | CFMe₂ | F | H | H | H | (3-chloro-5-fluoro-phenyl)methyl | 1.095 | 424 |
| 50. | CFMe₂ | F | H | H | H | (4-methoxycarbonyloxazol-2-yl)methyl | 0.847 | 421.1 |
| 51. | CFMe₂ | F | H | H | H | (5-methyl-1,3,4-oxadiazol-2-yl)methyl | 0.784 | 378 |
| 52. | 1-methylcyclobutyl | F | H | H | H | benzyl | 1.008 | 380.1 |
| 53. | CFMe₂ | F | H | H | H | (3-chloro-5-methoxy-phenyl)methyl | 1.082 | 435.9 |
| 54. | CFMe₂ | F | H | H | H | (3-fluoro-5-methoxy-phenyl)methyl | 1.039 | 420.0 |
| 55. | CFMe₂ | F | H | H | H | (3-chloro-4-fluoro-phenyl)methyl | 1.070 | 424.0 |
| 56. | CFMe₂ | F | H | H | H | (3-fluoro-4-methyl-phenyl)methyl | 1.070 | 404.0 |
| 57. | CFMe₂ | F | H | H | H | (3,5-dichlorophenyl)methyl | 1.090 | 440.0 |
| 58. | CFMe₂ | F | H | H | H | [3-(difluoromethoxy)phenyl]methyl | 1.016 | 438.1 |
| 59. | CFMe₂ | F | H | H | H | (3-methylsulfonylphenyl)methyl | 0.888 | 449.9 |
| 60. | CFMe₂ | F | H | F | H | benzyl | 1.008 | 390.0 |
| 61. | CFMe₂ | F | Br | H | H | benzyl | 1.008 | 380.1 |
| 62. | CFMe₂ | F | H | H | H | (3-fluoro-4-methoxy-phenyl)methyl | 1.001 | 420.0 |
| 63. | CFMe₂ | F | H | H | H | [3-(difluoromethoxy)-5-fluoro-phenyl]methyl | 1.061 | 456.1 |
| 64. | CFMe₂ | F | H | H | H | thiazol-5-ylmethyl | 0.816 | 378.9 |
| 65. | 1-fluoro-2-methyl-propyl | F | H | H | H | benzyl | 1.061 | 385.9 |
| 66. | CFMe₂ | F | H | H | H | (3-methyl-1,2,4-oxadiazol-5-yl)methyl | 0.842 | 378 |
| 67. | 1-fluorocyclopent-3-en-1-yl | F | H | H | H | benzyl | 1.037 | 396.0 |
| 68. | CFMe₂ | F | H | H | H | (3-chloro-4-methylsulfanyl-phenyl)methyl | 1.100 | 452.0 |
| 69. | CFMe₂ | F | F | F | H | benzyl | 1.096 | 408.0 |
| 70. | CFMe₂ | F | H | H | H | oxazol-2-ylmethyl | 0.819 | 363 |
| 71. | CFMe₂ | F | H | H | H | (4-methoxycarbonylthiazol-2-yl)methyl | 0.877 | 437.0 |
| 72. | CFMe₂ | F | H | H | F | benzyl | 1.041 | 390.0 |
| 73. | CFMe₂ | F | H | H | H | (3,5-difluoro-4-methoxy-phenyl)methyl | 1.046 | 438.1 |
| 74. | CFMe₂ | F | H | H | H | (2,3,5-trifluorophenyl)methyl | 1.042 | 426.0 |
| 75. | CFMe₂ | F | H | H | H | (3,5-dimethoxyphenyl)methyl | 1.012 | 432.0 |
| 76. | 1-(fluoromethyl)cyclopropyl | F | H | H | H | benzyl | 0.961 | 383.9 |
| 77. | 1-fluorobutyl | F | H | H | H | benzyl | 1.091 | 386.0 |
| 78. | CFMe₂ | F | H | H | H | (2,6-dichlorophenyl)methyl | 1.067 | 440.0 |
| 79. | CFMe₂ | F | H | H | H | (3-chloro-4-ethoxy-phenyl)methyl | 1.103 | 450.1 |
| 80. | CFMe₂ | F | H | H | H | (3-isopropylphenyl)methyl | 1.152 | 414.1 |
| 81. | CFMe₂ | Br | H | H | H | benzyl | 1.01 | 433.9 |
| 82. | CFMe₂ | H | H | H | H | benzyl | 1.060 | 354.0 |
| 83. | CFMe₂ | F | H | H | H | difluoro(phenyl)methyl | 1.098 | 408.4 |
| 84. | CFMe₂ | F | H | H | H | (3-cyanophenyl)methyl | 0.961 | 397.0 |
| 85. | CFMe₂ | Cl | H | H | H | benzyl | 1.035 | 388.4 |
| 86. | CFMe₂ | F | H | H | H | (4-vinylphenyl)methyl | 1.084 | 398.4 |

TABLE 3-continued

| ex.no. | $R^2R^3R^4$ | $R^a$ | $R^{b1}$ | $R^{b2}$ | $R^{b3}$ | $R^6R^7R^7$ | MS | HPLC |
|---|---|---|---|---|---|---|---|---|
| 87. | CFMe$_2$ | F | H | H | H | [4-(methylcarbamoyl)phenyl]methyl | 0.84 | 429.0 |
| 88. | CFMe$_2$ | F | H | H | H | (4-methoxycarbonylphenyl)methyl | 0.986 | 430.1 |
| 89. | CFMe$_2$ | F | H | H | H | (3-methoxycarbonylphenyl)methyl | 0.984 | 430.1 |
| 90. | CFMe$_2$ | F | H | H | H | 2-pyridylmethyl | 0.739 | 373.0 |
| 91. | CMe2OMe | F | H | H | H | benzyl | 0.943 | 384.1 |
| 92. | CFMe$_2$ | F | H | H | H | 4-pyridylmethyl | 0.675 | 372.9 |
| 93. | CFMe$_2$ | F | H | H | H | (3-carboxyphenyl)methyl | 0.880 | 416.0 |
| 94. | CFMe$_2$ | F | H | H | H | (4-ethylphenyl)methyl | 1.114 | 400 |
| 95. | CFMe$_2$ | F | H | H | H | (3,4-dimethylphenyl)methyl | 1.087 | 400.0 |
| 96. | CF$_2$Me | F | H | H | H | benzyl | 1.088 | 376.0 |
| 97. | CFMe$_2$ | F | F | F | H | (3-fluorophenyl)methyl | 1.067 | 425.9 |
| 98. | CFMe$_2$ | F | F | F | H | (3-methoxyphenyl)methyl | 1.063 | 438.0 |
| 99. | CFMe$_2$ | F | H | H | H | (2,6-difluorophenyl)methyl | 1.067 | 425.9 |
| 100. | CFMe$_2$ | F | H | H | H | (2-methoxyphenyl)methyl | 0.999 | 402.0 |
| 101. | CFMe$_2$ | F | H | H | H | [4-(difluoromethyl)phenyl]-difluoro-methyl | 1.087 | 457.9 |
| 102. | CFMe$_2$ | F | H | H | H | (3-fluoro-2-methyl-phenyl)methyl | 1.023 | 403.9 |
| 103. | CFMe$_2$ | F | H | H | H | (4-carboxyphenyl)methyl | 0.886 | 416.0 |
| 104. | CFMe$_2$ | F | H | H | H | (4-chlorophenyl)-difluoro-methyl | 1.15 | 442.0 |
| 105. | CFMe$_2$ | F | H | H | H | (5-methoxycarbonyl-3-thienyl)methyl | 0.977 | 436.0 |
| 106. | CFMe$_2$ | F | H | H | H | (5-methyl-3-thienyl)methyl | 1.033 | 392.0 |
| 107. | CFMe$_2$ | F | H | H | H | (2-chloro-3-thienyl)methyl | 1.047 | 412.0 |
| 108. | CFMe$_2$ | F | F | H | H | benzyl | 1.056 | 390.0 |
| 109. | CFMe$_2$ | F | H | H | H | (3-fluoro-2-methoxycarbonyl-phenyl)methyl | 1.027 | 448.0 |
| 110. | CFMe$_2$ | F | H | H | H | (5-chloro-3-thienyl)methyl | 1.073 | 411.9 |
| 111. | CFMe$_2$ | F | H | H | H | (4-methyl-3-thienyl)methyl | 1.045 | 391.9 |
| 112. | CFMe$_2$ | F | H | H | H | (2,5-dichloro-3-thienyl)methyl | 1.158 | 445.9 |
| 113. | CFMe$_2$ | F | H | H | H | benzyl | 1.063 | 388.0 |
| 114. | CMe$_2$OMe | F | H | H | H | (3-fluorophenyl)methyl | 0.926 | 401.9 |
| 115. | CMe$_2$OMe | F | H | H | H | (3-methoxyphenyl)methyl | 0.924 | 414.0 |
| 116. | CFMe$_2$ | F | F | F | H | difluoro(phenyl)methyl | 1.171 | 444.0 |
| 117. | CMe$_2$OMe | F | H | H | H | difluoro(phenyl)methyl | 0.971 | 420.1 |
| 118. | CFMe$_2$ | F | H | H | H | benzyl | 0.969 | 420 |
| 119. | CFMe$_2$ | F | H | H | H | (5-acetyl-3-thienyl)methyl | 0.898 | 420.0 |
| 120. | CFMe$_2$ | F | H | H | H | (5-chloro-2-thienyl)methyl | 1.046 | 411.9 |
| 121. | CFMe$_2$ | F | H | H | H | (2-cyano-3-thienyl)methyl | 0.942 | 402.9 |
| 122. | CFMe$_2$ | F | H | H | H | (2-cyano-3-fluoro-phenyl)methyl | 0.977 | 414.9 |
| 123. | CFMe$_2$ | F | H | H | H | benzyl | 0.909 | 403.9 |
| 124. | CFMe$_2$ | F | H | H | H | (5-cyano-3-thienyl)methyl | 0.939 | 402.9 |
| 125. | CFMe$_2$ | F | H | H | H | (2,5-dimethyl-3-thienyl)methyl | 1.068 | 405.9 |
| 126. | CFMe$_2$ | F | H | H | H | (4-cyano-3-thienyl)methyl | 0.903 | 402.9 |
| 127. | CFMe$_2$ | H | F | H | H | benzyl | 1.153 | 371.9 |
| 128. | CFMe$_2$ | CN | H | H | H | benzyl | 0.98 | 379 |
| 129. | CFMe$_2$ | F | F | F | H | difluoro-(3-fluorophenyl)methyl | 1.193 | 461.9 |
| 130. | CFMe$_2$ | F | H | H | H | difluoro-(3-fluorophenyl)methyl | 1.098 | 425.9 |
| 131. | CMe$_2$OMe | F | H | H | H | difluoro-(3-fluorophenyl)methyl | 0.998 | 437.9 |
| 132. | CFMe$_2$ | F | H | H | H | (3-isopropoxyphenyl)methyl | 1.101 | 430.0 |
| 133. | CFMe$_2$ | F | H | H | H | (3-isobutoxyphenyl)methyl | 1.182 | 444.1 |
| 134. | CFMe$_2$ | F | H | H | H | [3-(2,2,2-trifluoroethoxy)phenyl]methyl | 1.096 | 470.0 |
| 135. | CMe$_2$OMe | F | H | H | F | benzyl | 0.970 | 402.0 |
| 136. | CFMe$_2$ | F | H | H | H | [3-(trifluoromethoxy)phenyl]methyl | 1.108 | 456.0 |
| 137. | CFMe$_2$ | F | H | H | H | (4-cyanophenyl)methyl | 0.970 | 397.0 |
| 138. | CFMe$_2$ | F | H | H | H | (4-chlorophenyl)methyl | 1.064 | 405.9 |
| 139. | CFMe$_2$ | F | H | H | F | (3-methoxyphenyl)methyl | 1.038 | 420.0 |
| 140. | CFMe$_2$ | F | H | H | F | (4-ethylphenyl)methyl | 1.148 | 418.0 |
| 141. | CFMe$_2$ | F | H | H | F | p-tolylmethyl | 1.053 | 404.0 |
| 142. | CFMe$_2$ | F | H | H | F | difluoro(phenyl)methyl | 1.068 | 426.0 |
| 143. | CFMe$_2$ | F | H | H | H | (4-isopropylphenyl)methyl | 1.147 | 414.1 |
| 144. | CFMe$_2$ | F | H | H | F | (2-chlorothiazol-5-yl)methyl | 0.985 | 430.8 |
| 145. | CFMe$_2$ | F | H | H | H | [3-(cyclopropylmethoxy)phenyl]methyl | 1.109 | 442.0 |
| 146. | CFMe$_2$ | F | H | H | H | (3-~{tert}-butoxyphenyl)methyl | 1.128 | 488.1 |
| 147. | CFMe$_2$ | F | H | H | H | [3-(2,2-difluoroethoxy)phenyl]methyl | 1.047 | 452.1 |
| 148. | CFMe$_2$ | F | H | H | Cl | benzyl | 1.088 | 405.9 |
| 149. | CFMe$_2$ | F | H | H | H | (3-ethoxyphenyl)methyl | 1.056 | 416.1 |
| 150. | CFMe$_2$ | F | H | H | H | [3-(2-methoxy-2-oxo-ethoxy)phenyl]methyl | 1.070 | no ionization |
| 151. | CFMe$_2$ | F | H | H | H | (3-acetoxyphenyl)methyl | 0.981 | 429.9 |
| 152. | 1-fluoro-2-methyl-prop-1-enyl | F | H | H | H | benzyl | 1.022 | 383.9 |
| 153. | CFMe$_2$ | F | H | H | H | (1-methylimidazol-2-yl)methyl | 0.659 | 375.9 |
| 154. | CFMe$_2$ | F | H | H | H | 2-thienylmethyl | 0.946 | 377.9 |
| 155. | CFMe$_2$ | F | F | H | F | benzyl | 1.086 | 408.0 |
| 156. | CF$_2$Me | F | F | F | H | benzyl | 1.154 | 411.9 |
| 157. | CFMe$_2$ | F | H | H | H | [3-(cyclopropoxy)phenyl]methyl | 1.059 | 428.3 |
| 158. | (~{E})-1-fluoro-3-methyl-but-1-enyl | F | H | H | H | benzyl | 1.179 | 397.9 |
| 159. | 1-fluoro-2-methyl-prop-1-enyl | F | F | F | H | benzyl | 1.098 | 419.9 |
| 160. | 1-fluoro-2-methyl-prop-1-enyl | F | H | H | F | benzyl | 1.038 | 401.9 |
| 161. | CHFMe | F | H | H | H | benzyl | 0.989 | 357.9 |
| 162. | CFMe2 | F | H | H | H | (4-cyclopropylphenyl)methyl | 1.119 | 412 |
| 163. | CFMe2 | F | Br | H | F | benzyl | 1.166 | 469.7 |

TABLE 3-continued

| ex.no. | R²R³R⁴ | Rᵃ | R^{b1} | R^{b2} | R^{b3} | R⁶R⁷R⁷ | MS | HPLC |
|---|---|---|---|---|---|---|---|---|
| 164. | CFMe2 | F | F | H | F | (3-methoxyphenyl)methyl | 1.086 | 437.9 |
| 165. | CFMe2 | F | F | H | F | (2,6-difluorophenyl)methyl | 1.093 | 443.9 |
| 166. | CFMe2 | F | H | H | F | (4-cyclopropylphenyl)methyl | 1.131 | 430.0 |
| 167. | CFMe2 | F | H | H | F | (2,6-difluorophenyl)methyl | 1.032 | 425.9 |
| 168. | 1-fluorovinyl | F | H | H | H | benzyl | 1.089 | 356.2 |
| 169. | 1-fluorobutyl | F | F | F | H | benzyl | 1.179 | 422.0 |
| 170. | 1-fluorobutyl | F | H | H | H | benzyl | 1.133 | 404.0 |
| 171. | CHFMe | F | H | H | H | difluoro(phenyl)methyl | 1.054 | 393.9 |
| 172. | CFMe2 | F | H | H | F | (2-fluorophenyl)methyl | 1.040 | 408.0 |
| 173. | CFMe2 | F | H | H | F | (2-methoxyphenyl)methyl | 1.066 | 420.0 |
| 174. | CFMe2 | F | H | H | F | 3-thienylmethyl | 1.017 | 396.0 |
| 175. | CFMe2 | F | H | H | Me | benzyl | 1.029 | 385.9 |
| 176. | CFMe2 | F | F | H | H | (2-chloro-6-fluoro-phenyl)methyl | 1.087 | 441.8 |
| 177. | CFMe2 | F | H | H | H | (2-chloro-6-fluoro-phenyl)methyl | 1.036 | 423.9 |
| 178. | CFMe2 | F | F | H | H | (2-methoxyphenyl)methyl | 1.124 | 438.0 |
| 179. | 1-fluorobutyl | F | H | H | H | difluoro(phenyl)methyl | 1.160 | 421.9 |
| 180. | CFMe2 | F | F | H | F | (4-methoxyphenyl)methyl | 1.089 | 438.1 |
| 181. | CFMe2 | F | F | H | F | o-tolylmethyl | 1.122 | 422.0 |
| 182. | CFMe2 | F | F | H | F | m-tolylmethyl | 1.142 | 422.0 |
| 183. | CFMe2 | F | F | H | F | p-tolylmethyl | 1.133 | 422.1 |
| 184. | 1-F-cPr | F | H | H | H | benzyl | 1.016 | 369.9 |
| 185. | CFMe2 | F | F | H | H | (3-methoxyphenyl)methyl | 1.047 | 419.9 |
| 186. | CFMe2 | F | F | H | H | (4-methoxyphenyl)methyl | 1.043 | 420.0 |
| 187. | 1-F-cPr | F | H | H | F | benzyl | 1.042 | 387.9 |
| 188. | CFMe2 | F | H | F | F | benzyl | 1.083 | 407.9 |
| 189. | cyclopropyl(fluoro)methyl | F | H | H | F | benzyl | 1.070 | 401.9 |
| 190. | 1-methoxyethyl | F | H | H | H | benzyl | 0.926 | 369.9 |
| 191. | 1-methoxyethyl | F | H | H | F | benzyl | 0.940 | 387.9 |
| 192. | CFMe2 | F | H | H | F | (4-methoxyphenyl)methyl | 1.039 | 419.9 |
| 193. | CFMe2 | F | H | H | F | (4-ethoxyphenyl)methyl | 1.100 | 433.9 |
| 194. | i-Pr | F | H | H | H | benzyl | 0.958 | 354.0 |
| 195. | 1-chloroethyl | F | H | H | H | benzyl | 1.069 | 374.0 |
| 196. | CHFMe | F | H | H | F | benzyl | 1.001 | 375.9 |
| 197. | 1-fluoro-2-methyl-prop-1-enyl | F | H | H | H | difluoro(phenyl)methyl | 1.107 | 419.9 |
| 198. | CFMe2 | F | F | H | H | (2-methoxyphenyl)methyl | 1.077 | 419.9 |
| 199. | 1-fluorocyclopentyl | F | H | H | F | benzyl | 1.141 | 423.9 |
| 200. | t-Bu | F | F | H | F | benzyl | 1.074 | 403.9 |
| 201. | 1-methylcyclobutyl | F | F | H | F | benzyl | 1.063 | 416.0 |
| 202. | cyclopentyl(fluoro)methyl | F | H | H | H | benzyl | 1.144 | 412.0 |
| 203. | CFMe2 | F | F | H | F | (2-fluorophenyl)methyl | 1.089 | 425.9 |
| 204. | CFMe2 | F | F | H | F | (3-fluorophenyl)methyl | 1.094 | 426.0 |
| 205. | CFMe2 | F | F | H | F | (4-fluorophenyl)methyl | 1.096 | 426.0 |
| 206. | CFMe2 | F | F | H | F | (2-chlorophenyl)methyl | 1.136 | 441.8 |
| 207. | CFMe2 | F | F | H | F | (4-chlorophenyl)methyl | 1.142 | 441.8 |
| 208. | CFMe2 | F | F | H | F | (2-isopropylphenyl)methyl | 1.227 | 449.9 |
| 209. | CHFMe | F | F | H | F | benzyl | 1.054 | 394.0 |
| 210. | CHFMe | F | F | H | F | (2-methoxyphenyl)methyl | 1.090 | 424.0 |
| 211. | CHFMe | F | F | H | F | (3-methoxyphenyl)methyl | 1.056 | 424.0 |
| 212. | CHFMe | F | F | H | F | (4-methoxyphenyl)methyl | 1.054 | 424.0 |
| 213. | CMe2OMe | F | F | H | F | benzyl | 1.001 | 420.0 |
| 214. | CMe2OMe | F | F | H | F | (2-methoxyphenyl)methyl | 1.027 | 450.1 |
| 215. | CMe2OMe | F | F | H | F | (3-methoxyphenyl)methyl | 1.006 | 450.1 |
| 216. | CFMe2 | F | F | H | F | (4-ethylphenyl)methyl | 1.204 | 435.9 |
| 217. | CFMe2 | F | F | H | F | (3-chlorophenyl)methyl | 1.148 | 441.8 |
| 218. | CFMe2 | F | F | H | F | (2-cyclopropylphenyl)methyl | 1.196 | 447.9 |
| 219. | CFMe2 | F | F | H | F | [3-(methoxymethyl)phenyl]methyl | 1.096 | 451.9 |
| 220. | CFMe2 | F | F | H | F | [4-(methoxymethyl)phenyl]methyl | 1.089 | 451.9 |
| 221. | CFMe2 | F | H | H | H | [4-(methoxymethyl)phenyl]methyl | 1.000 | 416.0 |
| 222. | CFMe2 | F | F | H | Br | benzyl | 1.157 | 468.0 |
| 223. | CFMe2 | F | H | H | Br | benzyl | 1.102 | 452.0 |
| 224. | CFMe2 | F | F | H | F | [2-(methoxymethyl)phenyl]methyl | 1.095 | 451.9 |
| 225. | CMe2OMe | F | F | H | F | (4-methoxyphenyl)methyl | 1.013 | 449.9 |
| 226. | CMe2OMe | F | F | H | F | o-tolylmethyl | 1.040 | 433.9 |
| 227. | CMe2OMe | F | F | H | F | m-tolylmethyl | 1.051 | 433.9 |
| 228. | CMe2OMe | F | F | H | F | p-tolylmethyl | 1.057 | 433.9 |
| 229. | CHFMe | F | F | H | F | o-tolylmethyl | 1.092 | 407.9 |
| 230. | CHFMe | F | F | H | F | m-tolylmethyl | 1.104 | 407.9 |
| 231. | CHFMe | F | F | H | F | p-tolylmethyl | 1.109 | 407.8 |
| 232. | CFMe2 | F | F | H | F | (2-bromophenyl)methyl | 1.150 | 486.0 |
| 233. | 1-fluoro-3-methyl-butyl | F | H | H | H | benzyl | 1.141 | 400.0 |
| 234. | CFMe2 | F | F | H | Cl | benzyl | 1.140 | 424.0 |
| 235. | CFMe2 | F | Br | H | Br | benzyl | 1.209 | 529.9 |
| 236. | CFMe2 | F | F | F | F | benzyl | 1.138 | 426.0 |
| 237. | 1-methoxyethyl | F | F | H | F | o-tolylmethyl | 0.986 | 419.9 |
| 238. | 1-methoxyethyl | F | F | H | F | m-tolylmethyl | 1.009 | 419.9 |
| 239. | 1-methoxyethyl | F | F | H | F | p-tolylmethyl | 0.997 | 419.9 |
| 240. | 1-methoxyethyl | F | F | H | F | (2-fluorophenyl)methyl | 0.981 | 424.0 |
| 241. | 1-methoxyethyl | F | F | H | F | (3-fluorophenyl)methyl | 0.993 | 424.0 |

TABLE 3-continued

| ex.no. | R²R³R⁴ | Rᵃ | R^{b1} | R^{b2} | R^{b3} | R⁶R⁷R⁷ | MS | HPLC |
|---|---|---|---|---|---|---|---|---|
| 242. | 1-methoxyethyl | F | F | H | F | (4-fluorophenyl)methyl | 0.991 | 424.0 |
| 243. | 1-methoxyethyl | F | F | H | F | (2-chlorophenyl)methyl | 1.022 | 440.0 |
| 244. | 1-methoxyethyl | F | F | H | F | (3-chlorophenyl)methyl | 1.030 | 440.0 |
| 245. | 1-methoxyethyl | F | F | H | F | (4-chlorophenyl)methyl | 1.028 | 440.0 |
| 246. | 1-chloro-1-methyl-ethyl | F | F | H | F | benzyl | 1.215 | 423.9 |
| 247. | 1-fluoro-1-methyl-propyl | F | F | H | F | benzyl | 1.128 | 421.9 |
| 248. | CMe2OMe | F | F | H | F | (2-fluorophenyl)methyl | 1.015 | 438.0 |
| 249. | CMe2OMe | F | F | H | F | (3-fluorophenyl)methyl | 1.023 | 438.0 |
| 250. | CMe2OMe | F | F | H | F | (4-fluorophenyl)methyl | 1.023 | 438.0 |
| 251. | CMe2OMe | F | F | H | F | (2-chlorophenyl)methyl | 1.050 | 454.0 |
| 252. | CMe2OMe | F | F | H | F | (3-chlorophenyl)methyl | 1.060 | 454.1 |
| 253. | CMe2OMe | F | F | H | F | (4-chlorophenyl)methyl | 1.058 | 454.0 |
| 254. | i-Pr | F | F | H | F | benzyl | 0.973 | 389.9 |
| 255. | CHFMe | F | F | H | F | (2,6-dimethylphenyl)methyl | 1.135 | 421.9 |
| 256. | 1-fluorocyclohexyl | F | F | H | F | benzyl | 1.208 | 448.1 |
| 257. | CFMe2 | F | H | H | H | benzyl | 1.046 | 369.9 |
| 258. | 1-fluorocyclohexyl | F | H | H | CN | benzyl | 1.093 | 436.9 |
| 259. | CFMe2 | F | H | H | CN | benzyl | 1.000 | 397.1 |
| 260. | 1-fluorocyclopentyl | Cl | H | H | Br | benzyl | 1.186 | 494.0 |
| 261. | CFMe2 | Cl | H | H | Br | benzyl | 1.143 | 468.0 |

B USE EXAMPLES

The herbicidal activity of the azines of formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this had been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C., respectively.

The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A moderate herbicidal activity is given at values of at least 60, a good herbicidal activity is given at values of at least 70, and a very good herbicidal activity is given at values of at least 85.

The plants used in the greenhouse experiments were of the following species:

| Bayer code | Scientific name |
|---|---|
| ABUTH | *Abutilon theophrasti* |
| ALOMY | *Alopercurus myosuroides* |
| AMARE | *Amaranthus retroflexus* |
| APESV | *Apera spica-venti* |
| CAPBP | *Capsella bursa-pastoris* |
| CHEAL | *Chenopodium album* |
| ECHCG | *Echinocloa crus-galli* |
| GERDI | *Geranium dissectum* |
| LAMPU | *Lamium purpureum* |
| LOLMU | *Lolium multiflorum* |
| MATIN | *Matricaria maritima* |
| POAAN | *Poa annua* |
| POLCO | *Polygonum convolvulus* |
| SETFA | *Setaria faberi* |
| SETVI | *Setaria viridis* |
| STEME | *Stellaria media* |
| THLAR | *Thlaspi arvense* |
| VIOAR | *Viola arvensis* |

Example 4 applied by pre-emergence method at an application rate of 250 g/ha, showed 100% herbicidal activity against *Alopercurus myosuroides, Amaranthus retroflexus, Echinocloa crus-galli* and *Setaria faber.*

Example 5 applied by pre-emergence method at an application rate of 250 g/ha, showed 85%, 98%, 100% and 98% herbicidal activity against *Alopercurus myosuroides, Amaranthus retroflexus, Echinocloa crus-galli* and *Setaria faber* respectively.

Example 6 applied by pre-emergence method at an application rate of 250 g/ha, showed 100% herbicidal activity against *Amaranthus retroflexus, Echinocloa crus-galli* and *Setaria faber.*

Example 9 applied by pre-emergence method at an application rate of 250 g/ha, showed 80%, 95%, 100% and 100% herbicidal activity against *Alopercurus myosuroides, Amaranthus retroflexus, Echinocloa crus-galli* and *Setaria faber* respectively.

Example 10 applied by pre-emergence method at an application rate of 250 g/ha, showed 100% herbicidal activity against *Alopercurus myosuroides, Amaranthus retroflexus, Echinocloa crus-galli* and *Setaria faber.*

Example 11 applied by pre-emergence method at an application rate of 250 g/ha, showed 100% herbicidal activity against *Alopercurus myosuroides, Amaranthus retroflexus, Echinocloa crus-galli* and *Setaria faber.*

Example 14 applied by pre-emergence method at an application rate of 250 g/ha, showed 85%, 90% and 80% herbicidal activity against *Alopercurus myosuroides, Echinocloa crus-galli* and *Setaria faber* respectively.

Example 18 applied by pre-emergence method at an application rate of 250 g/ha, showed 70%, 70%, 70% and 85% herbicidal activity against *Alopercurus myosuroides, Amaranthus retroflexus, Echinocloa crus-galli* and *Setaria faber* respectively.

Example 19 applied by pre-emergence method at an application rate of 250 g/ha, showed 70%, 80% and 85% herbicidal activity against *Alopercurus myosuroides, Amaranthus retroflexus* and *Setaria faber* respectively.

Example 20 applied by pre-emergence method at an application rate of 250 g/ha, showed 100%, 98%, 100% and 95% herbicidal activity against *Alopercurus myosuroides, Amaranthus retroflexus, Echinocloa crus-galli* and *Setaria faber* respectively.

Example 22 applied by pre-emergence method at an application rate of 250 g/ha, showed 100% herbicidal activity against *Abutilon theophrasti, Amaranthus retroflexus, Echinocloa crus-galli* and *Setaria faberi*.

Example 23 applied by pre-emergence method at an application rate of 250 g/ha, showed 100% and 75% herbicidal activity against *Echinocloa crus-galli* and *Setaria faberi* respectively.

Example 26 applied by pre-emergence method at an application rate of 250 g/ha, showed 85%, 80% and 70% herbicidal activity against *Abutilon theophrasti, Echinocloa crus-galli* and *Setaria faberi* respectively.

Example 27 applied by pre-emergence method at an application rate of 250 g/ha, showed 100% herbicidal activity against *Abutilon theophrasti, Echinocloa crus-galli* and *Setaria faberi*.

Example 28 applied by post-emergence method at an application rate of 125 g/ha, showed 75%, 85% and 75% herbicidal activity against *Abutilon theophrasti, Echinocloa crus-galli* and *Setaria viridis* respectively.

Example 30 applied by pre-emergence method at an application rate of 250 g/ha, showed 100% herbicidal activity against *Abutilon theophrasti, Amaranthus retroflexus, Echinocloa crus-galli* and *Setaria faberi*.

Example 31 applied by pre-emergence method at an application rate of 250 g/ha, showed 85%, 75% and 100% herbicidal activity against *Abutilon theophrasti, Amaranthus retroflexus* and *Echinocloa crus-galli* respectively.

Example 33 applied by pre-emergence method at an application rate of 250 g/ha, showed 75% and 60% herbicidal activity against *Alopercurus myosuroides* and *Echinocloa crus-galli* respectively.

Example 35 applied by pre-emergence method at an application rate of 250 g/ha, showed 100% herbicidal activity against *Abutilon theophrasti, Amaranthus retroflexus, Echinocloa crus-galli* and *Setaria faberi*.

Example 36 applied by pre-emergence method at an application rate of 250 g/ha, showed 100% and 75% herbicidal activity against *Amaranthus retroflexus* and *Echinocloa crus-galli* respectively.

Example 39 applied by pre-emergence method at an application rate of 250 g/ha, showed 90%, 80%, 100% and 90% herbicidal activity against *Alopercurus myosuroides, Amaranthus retroflexus, Echinocloa crus-galli* and *Setaria faberi* respectively.

Example 42 applied by pre-emergence method at an application rate of 250 g/ha, showed 100% and 80% herbicidal activity against *Amaranthus retroflexus* and *Abutilon theophrasti* respectively.

Example 43 applied by pre-emergence method at an application rate of 250 g/ha, showed 100% herbicidal activity against *Amaranthus retroflexus, Abutilon theophrasti* and *Echincloa crus-galli*.

Example 44 applied by pre-emergence method at an application rate of 250 g/ha, showed 70% and 70% herbicidal activity against *Setaria faberi* and *Abutilon theophrasti* respectively.

Example 45 applied by pre-emergence method at an application rate of 250 g/ha, showed 80%, 70% and 80% herbicidal activity against *Alopercurus myosuroides, Setaria faberi* and *Echinocloa crus-galli* respectively.

Example 47 applied by pre-emergence method at an application rate of 250 g/ha, showed 100%, 100% and 80% herbicidal activity against *Abutilon theophrasti, Amaranthus retroflexus* and *Echinocloa crus-galli* respectively.

Example 52 applied by pre-emergence method at an application rate of 250 g/ha, showed 90% and 85% herbicidal activity against *Echinocloa crus-galli* and *Setaria faberi*.

Example 54 applied by pre-emergence method at an application rate of 250 g/ha, showed 90% and 100% herbicidal activity against *Alopercurus myosuroides* and *Echinocloa crus-galli*.

Example 56 applied by pre-emergence method at an application rate of 250 g/ha, showed 100% and 95% herbicidal activity against *Lolium multiflorum* and *Echinocloa crus-galli*.

Example 58 applied by pre-emergence method at an application rate of 250 g/ha, showed 100%, 90% and 100% herbicidal activity against *Amaranthus retroflexus, Echinocloa crus-galli* and *Setaria faberi* respectively.

Example 60 applied by pre-emergence method at an application rate of 250 g/ha, showed 98%, 100%, 100% and 100% herbicidal activity against *Alopercurus myosuroides, Amaranthus retroflexus, Echinocloa crus-galli* and *Setaria faberi* respectively.

Example 61 applied by pre-emergence method at an application rate of 250 g/ha, showed 80%, 100% and 100% herbicidal activity against *Amaranthus retroflexus, Echinocloa crus-galli* and *Setaria faberi* respectively.

Example 65 applied by pre-emergence method at an application rate of 250 g/ha, showed 95% and 95% herbicidal activity against *Alopercurus myosuroides* and *Echinocloa crus-galli* respectively.

Example 69 applied by pre-emergence method at an application rate of 250 g/ha, showed 100% herbicidal activity against *Alopercurus myosuroides, Amaranthus retroflexus, Echinocloa crus-galli* and *Setaria faberi*.

Example 70 applied by pre-emergence method at an application rate of 250 g/ha, showed 100% herbicidal activity against *Abutilon theophrasti, Amaranthus retroflexus* and *Echinocloa crus-galli*.

Example 72 applied by pre-emergence method at an application rate of 250 g/ha, showed 100% herbicidal activity against *Amaranthus retroflexus, Echinocloa crus-galli* and *Setaria faberi*.

Example 73 applied by pre-emergence method at an application rate of 250 g/ha, showed 70% and 75% herbicidal activity against *Amaranthus retroflexus* and *Echinocloa crus-galli* respectively.

Example 74 applied by pre-emergence method at an application rate of 250 g/ha, showed 80% and 85% herbicidal activity against *Amaranthus retroflexus* and *Echinocloa crus-galli* respectively.

Example 77 applied by pre-emergence method at an application rate of 250 g/ha, showed 80%, 100% and 100% herbicidal activity against *Abutilon theophrasti, Setaria faberi* and *Echinocloa crus-galli* respectively.

Example 78 applied by pre-emergence method at an application rate of 250 g/ha, showed 100%, 100% and 75% herbicidal activity against *Alopercurus myosuroides, Echinocloa crus-galli* and *Setaria faberi* respectively.

Example 83 applied by pre-emergence method at an application rate of 250 g/ha, showed 100% herbicidal activity against *Alopercurus myosuroides, Echinocloa crus-galli* and *Setaria faberi*.

Example 85 applied by pre-emergence method at an application rate of 250 g/ha, showed 70%, 70% and 90% herbicidal activity against *Setaria faberi, Alopercurus myosuroides* and *Abutilon theophrasti* respectively.

Example 91 applied by pre-emergence method at an application rate of 250 g/ha, showed 100% herbicidal activity against *Alopercurus myosuroides, Amaranthus retroflexus, Echinocloa crus-galli* and *Setaria faberi*.

Example 94 applied by pre-emergence method at an application rate of 250 g/ha, showed 100% and 70% herbicidal activity against *Alopercurus myosuroides* and *Amaranthus retroflexus* respectively.

Example 96 applied by pre-emergence method at an application rate of 250 g/ha, showed 80%, 100%, 100% and 95% herbicidal activity against *Alopercurus myosuroides, Amaranthus retroflexus, Echinocloa crus-galli* and *Setaria faberi* respectively.

Example 97 applied by pre-emergence method at an application rate of 250 g/ha, showed 100% herbicidal activity against *Amaranthus retroflexus, Echinocloa crus-galli* and *Setaria faberi*.

Example 98 applied by pre-emergence method at an application rate of 250 g/ha, showed 80%, 90%, 100% and 100% herbicidal activity against *Alopercurus myosuroides, Amaranthus retroflexus, Echinocloa crus-galli* and *Setaria faberi* respectively.

Example 99 applied by pre-emergence method at an application rate of 250 g/ha, showed 100%, 100%, 90% and 100% herbicidal activity against *Alopercurus myosuroides, Amaranthus retroflexus, Echinocloa crus-galli* and *Setaria faberi* respectively.

Example 100 applied by pre-emergence method at an application rate of 250 g/ha, showed 100%, 100% and 80% herbicidal activity against *Amaranthus retroflexus, Echinocloa crus-galli* and *Abutilon theophrasti* respectively.

Example 102 applied by pre-emergence method at an application rate of 250 g/ha, showed 100%, 100% and 85% herbicidal activity against *Setaria faberi, Echinocloa crus-galli* and *Abutilon theophrasti* respectively.

Example 107 applied by pre-emergence method at an application rate of 250 g/ha, showed 75%, 75%, 100% and 100% herbicidal activity against *Alopercurus myosuroides, Amaranthus retroflexus, Echinocloa crus-galli* and *Setaria faberi* respectively.

Example 108 applied by pre-emergence method at an application rate of 250 g/ha, showed 100% herbicidal activity against *Alopercurus myosuroides, Amaranthus retroflexus, Echinocloa crus-galli* and *Setaria faberi*.

Example 110 applied by pre-emergence method at an application rate of 250 g/ha, showed 90% and 80% herbicidal activity against *Echinocloa crus-galli* and *Setaria faber* respectively.

Example 111 applied by post-emergence method at an application rate of 250 g/ha, showed 100% herbicidal activity against *Abutilon theophrasti* and *Amaranthus retroflexus*.

Example 111 applied by pre-emergence method at an application rate of 250 g/ha, showed 80% and 85% herbicidal activity against *Apera spica-venti* and *Echinocloa crus-galli* respectively.

Example 112 applied by post-emergence method at an application rate of 250 g/ha, showed 100% herbicidal activity against *Abutilon theophrasti* and *Amaranthus retroflexus*.

Example 112 applied by pre-emergence method at an application rate of 250 g/ha, showed 80% herbicidal activity against *Apera spica-venti* and *Echinocloa crus-galli*.

Example 114 applied by pre-emergence method at an application rate of 250 g/ha, showed 90% herbicidal activity against *Echinocloa crus-galli* and *Setaria faberi*.

Example 116 applied by pre-emergence method at an application rate of 250 g/ha, showed 100% herbicidal activity against *Amaranthus retroflexus, Echinocloa crus-galli* and *Setaria* faber.

Example 117 applied by pre-emergence method at an application rate of 250 g/ha, showed 100% herbicidal activity against *Amaranthus retroflexus, Echinocloa crus-galli* and *Setaria* faber.

Example 120 applied by pre-emergence method at an application rate of 250 g/ha, showed 75%, 100% and 90% herbicidal activity against *Alopercurus myosuroides, Echinocloa crus-galli* and *Setaria faber* respectively.

Example 121 applied by post-emergence method at an application rate of 250 g/ha, showed 100% herbicidal activity against *Abutilon theophrasti* and *Amaranthus retroflexus*.

Example 121 applied by pre-emergence method at an application rate of 250 g/ha, showed 80% herbicidal activity against *Amaranthus retroflexus*.

Example 125 applied by pre-emergence method at an application rate of 250 g/ha, showed 85% and 100% herbicidal activity against *Apera spica-venti* and *Echinocloa crus-galli* respectively.

Example 128 applied by pre-emergence method at an application rate of 250 g/ha, showed 100%, 90% and 90% herbicidal activity against *Amaranthus retroflexus, Setaria* faber and *Abutilon theophrasti* respectively.

Example 129 applied by pre-emergence method at an application rate of 250 g/ha, showed 100% herbicidal activity against *Amaranthus retroflexus, Echinocloa crus-galli* and *Setaria* faber.

Example 130 applied by pre-emergence method at an application rate of 250 g/ha, showed 100% herbicidal activity against *Abutilon theophrasti, Setaria* faber and *Echinocloa crus-galli*.

Example 131 applied by pre-emergence method at an application rate of 250 g/ha, showed 90%, 85% and 90% herbicidal activity against *Abutilon theophrasti, Amaranthus retroflexus* and *Setaria faber* respectively.

Example 132 applied by pre-emergence method at an application rate of 250 g/ha, showed 90%, 90% and 100% herbicidal activity against *Amaranthus retroflexus, Setaria* faber and *Echinocloa crus-galli* respectively.

Example 134 applied by pre-emergence method at an application rate of 250 g/ha, showed 95%, 90% and 90% herbicidal activity against *Apera spica-venti, Echinocloa crus-galli* and *Setaria faber* respectively.

Example 135 applied by pre-emergence method at an application rate of 250 g/ha, showed 100% herbicidal activity against *Amaranthus retroflexus, Setaria* faber and *Echinocloa crus-galli*.

Example 136 applied by pre-emergence method at an application rate of 250 g/ha, showed 80%, 85% and 80% herbicidal activity against *Apera spica-venti, Echinocloa crus-galli* and *Setaria faber* respectively.

Example 139 applied by pre-emergence method at an application rate of 250 g/ha, showed 100% herbicidal activity against *Abutilon theophrasti, Amaranthus retroflexus, Echinocloa crus-galli* and *Setaria faber.*

Example 140 applied by pre-emergence method at an application rate of 250 g/ha, showed 98% and 100% herbicidal activity against *Echinocloa crus-galli* and *Setaria faber* respectively.

Example 141 applied by pre-emergence method at an application rate of 250 g/ha, showed 98%, 100% and 100% herbicidal activity against *Abutilon theophrasti, Echinocloa crus-galli* and *Setaria faber* respectively.

Example 142 applied by pre-emergence method at an application rate of 250 g/ha, showed 100% herbicidal activity against *Amaranthus retroflexus, Echinocloa crus-galli* and *Setaria* faber.

Example 143 applied by pre-emergence method at an application rate of 250 g/ha, showed 90% and 100% herbicidal activity against *Alopercurus myosuroides* and *Amaranthus retroflexus* respectively.

Example 148 applied by pre-emergence method at an application rate of 250 g/ha, showed 100% herbicidal activity against *Amaranthus retroflexus, Echinocloa crus-galli* and *Setaria* faber.

Example 149 applied by pre-emergence method at an application rate of 250 g/ha, showed 85%, 90% and 75% herbicidal activity against *Alopercurus myosuroides, Setaria* faber and *Echinocloa crus-galli* respectively.

Example 152 applied by pre-emergence method at an application rate of 250 g/ha, showed 100% and 90% herbicidal activity against *Amaranthus retroflexus* and *Setaria faber* respectively.

Example 154 applied by pre-emergence method at an application rate of 250 g/ha, showed 100% herbicidal activity against *Amaranthus retroflexus, Echinocloa crus-galli* and *Setaria* faber.

Example 160 applied by pre-emergence method at an application rate of 250 g/ha, showed 85% and 75% herbicidal activity against *Alopercurus myosuroides* and *Setaria faber* respectively.

Example 161 applied by pre-emergence method at an application rate of 250 g/ha, showed 100% herbicidal activity against *Echinocloa crus-galli* and *Setaria faberi.*

Example 163 applied by pre-emergence method at an application rate of 250 g/ha, showed 100% herbicidal activity against *Alopercurus myosuroides, Echinocloa crus-galli* and *Setaria* faber.

Example 164 applied by pre-emergence method at an application rate of 250 g/ha, showed 100% herbicidal activity against *Alopercurus myosuroides, Echinocloa crus-galli* and *Setaria* faber.

Example 165 applied by pre-emergence method at an application rate of 250 g/ha, showed 100% herbicidal activity against *Abutilon theophrasti, Alopercurus myosuroides* and *Echinocloa crus-galli.*

Example 167 applied by pre-emergence method at an application rate of 250 g/ha, showed 100% herbicidal activity against *Abutilon theophrasti, Alopercurus myosuroides* and *Setaria* faber.

Example 169 applied by pre-emergence method at an application rate of 250 g/ha, showed 80% and 85% herbicidal activity against *Amaranthus retroflexus* and *Setaria faber* respectively.

Example 170 applied by pre-emergence method at an application rate of 250 g/ha, showed 90%, 100% and 90% herbicidal activity against *Amaranthus retroflexus, Echinocloa crus-galli* and *Setaria faber* respectively.

Example 171 applied by pre-emergence method at an application rate of 250 g/ha, showed 100%, 85% and 100% herbicidal activity against *Amaranthus retroflexus, Echinocloa crus-galli* and *Setaria faber* respectively.

Example 172 applied by pre-emergence method at an application rate of 250 g/ha, showed 100% herbicidal activity against *Abutilon theophrasti, Echinocloa crus-galli* and *Setaria faber.*

Example 173 applied by pre-emergence method at an application rate of 250 g/ha, showed 100% herbicidal activity against *Abutilon theophrasti, Amaranthus retroflexus* and *Echinocloa crus-galli.*

Example 174 applied by pre-emergence method at an application rate of 250 g/ha, showed 100% herbicidal activity against *Alopercurus myosuroides, Echinocloa crus-galli* and *Setaria* faber.

Example 175 applied by pre-emergence method at an application rate of 250 g/ha, showed 85%, 100% and 95% herbicidal activity against *Abutilon theophrasti, Echinocloa crus-galli* and *Setaria* faber respectively.

Example 176 applied by pre-emergence method at an application rate of 250 g/ha, showed 100%, 100% and 80% herbicidal activity against *Echinocloa crus-galli* and *Setaria faberi, Amaranthus retroflexus* respectively.

Example 177 applied by pre-emergence method at an application rate of 250 g/ha, showed 85%, 100% and 95% herbicidal activity against *Alopercurus myosuroides, Echinocloa crus-galli* and *Setaria faber* respectively.

Example 178 applied by pre-emergence method at an application rate of 250 g/ha, showed 98%, 100% and 100% herbicidal activity against *Alopercurus myosuroides, Echinocloa crus-galli* and *Setaria faber* respectively.

Example 180 applied by pre-emergence method at an application rate of 250 g/ha, showed 90%, 100% and 100% herbicidal activity against *Alopercurus myosuroides, Echinocloa crus-galli* and *Setaria faber* respectively.

Example 181 applied by pre-emergence method at an application rate of 250 g/ha, showed 98%, 100% and 100% herbicidal activity against *Alopercurus myosuroides, Echinocloa crus-galli* and *Setaria faber* respectively.

Example 182 applied by pre-emergence method at an application rate of 250 g/ha, showed 100%, 100% and 100% herbicidal activity against *Alopercurus myosuroides, Echinocloa crus-galli* and *Setaria faber* respectively.

Example 183 applied by pre-emergence method at an application rate of 250 g/ha, showed 100% herbicidal activity against *Abutilon theophrasti, Echinocloa crus-galli* and *Setaria faberi.*

Example 184 applied by pre-emergence method at an application rate of 250 g/ha, showed 85%, 95% and 98% herbicidal activity against *Alopercurus myosuroides, Amaranthus retroflexus* and *Echinocloa crus-galli* respectively.

Example 185 applied by pre-emergence method at an application rate of 250 g/ha, showed 98%, 100% and 100% herbicidal activity against *Alopercurus myosuroides, Echinocloa crus-galli* and *Setaria faber* respectively.

Example 186 applied by pre-emergence method at an application rate of 250 g/ha, showed 85% and 98% herbicidal activity against *Alopercurus myosuroides,* and *Echinocloa crus-galli* respectively.

Example 187 applied by pre-emergence method at an application rate of 250 g/ha, showed 85%, 100% and 100% herbicidal activity against *Alopercurus myosuroides, Echinocloa crus-galli* and *Setaria faber* respectively.

Example 188 applied by pre-emergence method at an application rate of 250 g/ha, showed 100% herbicidal activity against *Abutilon theophrasti, Alopercurus myosuroides* and *Echinocloa crus-galli*.

Example 189 applied by pre-emergence method at an application rate of 250 g/ha, showed 98%, 100% and 100% herbicidal activity against *Alopercurus myosuroides, Echinocloa crus-galli* and *Setaria faber* respectively.

Example 191 applied by pre-emergence method at an application rate of 250 g/ha, showed 95%, 100% and 100% herbicidal activity against *Amaranthus retroflexus, Echinocloa crus-galli* and *Setaria faber* respectively.

Example 192 applied by pre-emergence method at an application rate of 250 g/ha, showed 100% herbicidal activity against *Echinocloa crus-galli* and *Setaria faberi*.

Example 193 applied by pre-emergence method at an application rate of 250 g/ha, showed 80%, 95% and 100% herbicidal activity against *Alopercurus myosuroides, Echinocloa crus-galli* and *Setaria faber* respectively.

Example 194 applied by pre-emergence method at an application rate of 250 g/ha, showed 100% and 70% herbicidal activity against *Echinocloa crus-galli* and *Setaria faber* respectively.

Example 196 applied by pre-emergence method at an application rate of 250 g/ha, showed 98%, 100% and 100% herbicidal activity against *Alopercurus myosuroides, Echinocloa crus-galli* and *Setaria faber* respectively.

Example 198 applied by pre-emergence method at an application rate of 250 g/ha, showed 98%, 100% and 100% herbicidal activity against *Abutilon theophrasti, Echinocloa crus-galli* and *Setaria faber* respectively.

Example 199 applied by pre-emergence method at an application rate of 250 g/ha, showed 100% herbicidal activity against *Abutilon theophrasti, Alopercurus myosuroides* and *Echinocloa crus-galli*.

Example 200 applied by pre-emergence method at an application rate of 250 g/ha, showed 100% herbicidal activity against *Abutilon theophrasti, Echinocloa crus-galli* and *Setaria faberi*.

Example 201 applied by pre-emergence method at an application rate of 250 g/ha, showed 100% herbicidal activity against *Alopercurus myosuroides, Echinocloa crus-galli* and *Setaria* faber.

Example 202 applied by pre-emergence method at an application rate of 250 g/ha, showed 80%, 80% and 85% herbicidal activity against *Abutilon theophrasti, Echinocloa crus-galli* and *Setaria faber* respectively.

Example 203 applied by pre-emergence method at an application rate of 250 g/ha, showed 100% herbicidal activity against *Alopercurus myosuroides, Echinocloa crus-galli* and *Setaria faberi*.

Example 204 applied by pre-emergence method at an application rate of 250 g/ha, showed 100% herbicidal activity against *Abutilon theophrasti, Alopercurus myosuroides, Echinocloa crus-galli* and *Setaria faberi*.

Example 205 applied by pre-emergence method at an application rate of 250 g/ha, showed 100% herbicidal activity against *Alopercurus myosuroides, Echinocloa crus-galli* and *Setaria* faber.

Example 206 applied by pre-emergence method at an application rate of 250 g/ha, showed 100% herbicidal activity against *Abutilon theophrasti, Alopercurus myosuroides, Echinocloa crus-galli* and *Setaria faberi*.

Example 207 applied by pre-emergence method at an application rate of 250 g/ha, showed 90%, 100% and 100% herbicidal activity against *Abutilon theophrasti, Echinocloa crus-galli* and *Setaria faber* respectively.

Example 208 applied by pre-emergence method at an application rate of 250 g/ha, showed 90% and 80% herbicidal activity against *Abutilon theophrasti* and *Amaranthus retroflexus* respectively.

Example 209 applied by pre-emergence method at an application rate of 250 g/ha, showed 100% herbicidal activity against *Amaranthus retroflexus, Echinocloa crus-galli* and *Setaria* faber.

Example 210 applied by pre-emergence method at an application rate of 250 g/ha, showed 100% herbicidal activity against *Amaranthus retroflexus, Echinocloa crus-galli* and *Setaria* faber.

Example 211 applied by pre-emergence method at an application rate of 250 g/ha, showed 100% herbicidal activity against *Amaranthus retroflexus, Echinocloa crus-galli* and *Setaria* faber.

Example 212 applied by pre-emergence method at an application rate of 250 g/ha, showed 100% herbicidal activity against *Amaranthus retroflexus, Echinocloa crus-galli* and *Setaria* faber.

Example 213 applied by pre-emergence method at an application rate of 250 g/ha, showed 100% herbicidal activity against *Amaranthus retroflexus, Echinocloa crus-galli* and *Setaria* faber.

Example 214 applied by pre-emergence method at an application rate of 250 g/ha, showed 100%, 98% and 90% herbicidal activity against *Abutilon theophrasti, Alopercurus myosuroides* and *Setaria faber* respectively.

Example 215 applied by pre-emergence method at an application rate of 250 g/ha, showed 100%, 98% and 98% herbicidal activity against *Amaranthus retroflexus, Echinocloa crus-galli* and *Setaria faber* respectively.

Example 216 applied by pre-emergence method at an application rate of 250 g/ha, showed 100%, 98% and 100% herbicidal activity against *Abutilon theophrasti, Alopercurus myosuroides* and *Setaria faber* respectively.

Example 217 applied by pre-emergence method at an application rate of 250 g/ha, showed 98%, 100% and 100% herbicidal activity against *Abutilon theophrasti, Echinocloa crus-galli* and *Setaria faber* respectively.

Example 218 applied by pre-emergence method at an application rate of 250 g/ha, showed 95%, 85% and 100% herbicidal activity against *Alopercurus myosuroides, Echinocloa crus-galli* and *Setaria faber* respectively.

Example 219 applied by pre-emergence method at an application rate of 250 g/ha, showed 100%, 85% and 100% herbicidal activity against *Abutilon theophrasti, Echinocloa crus-galli* and *Setaria faber* respectively.

Example 220 applied by pre-emergence method at an application rate of 250 g/ha, showed 98%, 95% and 90% herbicidal activity against *Alopercurus myosuroides, Echinocloa crus-galli* and *Setaria faber* respectively.

Example 222 applied by pre-emergence method at an application rate of 250 g/ha, showed 98%, 100% and 100% herbicidal activity against *Abutilon theophrasti, Echinocloa crus-galli* and *Setaria faber* respectively.

Example 223 applied by pre-emergence method at an application rate of 250 g/ha, showed 100%, 95% and 100% herbicidal activity against *Abutilon theophrasti, Echinocloa crus-galli* and *Setaria faber* respectively.

Example 224 applied by pre-emergence method at an application rate of 250 g/ha, showed 100%, 90% and 100% herbicidal activity against *Abutilon theophrasti, Echinocloa crus-galli* and *Setaria faber* respectively.

Example 226 applied by pre-emergence method at an application rate of 250 g/ha, showed 90%, 100% and 100% herbicidal activity against *Abutilon theophrasti, Alopercurus myosuroides* and *Echinocloa crus-galli* respectively.

Example 227 applied by pre-emergence method at an application rate of 250 g/ha, showed 90%, 75% and 85% herbicidal activity against *Alopercurus myosuroides, Echinocloa crus-galli* and *Setaria faber* respectively.

Example 228 applied by pre-emergence method at an application rate of 250 g/ha, showed 100%, 100% and 90% herbicidal activity against *Abutilon theophrasti, Alopercurus myosuroides* and *Echinocloa crus-galli* respectively.

Example 229 applied by pre-emergence method at an application rate of 250 g/ha, showed 100% herbicidal activity against *Abutilon theophrasti, Alopercurus myosuroides* and *Echinocloa crus-galli*.

Example 230 applied by pre-emergence method at an application rate of 250 g/ha, showed 95%, 95% and 95% herbicidal activity against *Amaranthus retroflexus, Echinocloa crus-galli* and *Setaria faber* respectively.

Example 231 applied by pre-emergence method at an application rate of 250 g/ha, showed 98%, 98% and 98% herbicidal activity against *Abutilon theophrasti, Alopercurus myosuroides* and *Echinocloa crus-galli* respectively.

Example 232 applied by pre-emergence method at an application rate of 250 g/ha, showed 100% herbicidal activity against *Abutilon theophrasti, Echinocloa crus-galli* and *Setaria faberi*.

Example 233 applied by pre-emergence method at an application rate of 250 g/ha, showed 75%, 80% and 95% herbicidal activity against *Abutilon theophrasti, Alopercurus myosuroides* and *Echinocloa crus-galli* respectively.

Example 234 applied by pre-emergence method at an application rate of 250 g/ha, showed 100%, 90% and 100% herbicidal activity against *Abutilon theophrasti, Alopercurus myosuroides* and *Echinocloa crus-galli* respectively.

Example 235 applied by pre-emergence method at an application rate of 250 g/ha, showed 85%, 90% and 100% herbicidal activity against *Amaranthus retroflexus, Echinocloa crus-galli* and *Setaria faber* respectively.

Example 236 applied by pre-emergence method at an application rate of 250 g/ha, showed 100%, 95% and 100% herbicidal activity against *Abutilon theophrasti, Alopercurus myosuroides* and *Echinocloa crus-galli* respectively.

Example 237 applied by pre-emergence method at an application rate of 250 g/ha, showed 95%, 100% and 95% herbicidal activity against *Amaranthus retroflexus, Echinocloa crus-galli* and *Setaria faber* respectively.

Example 238 applied by pre-emergence method at an application rate of 250 g/ha, showed 80%, 98% and 100% herbicidal activity against *Amaranthus retroflexus, Echinocloa crus-galli* and *Setaria faber* respectively.

Example 240 applied by pre-emergence method at an application rate of 250 g/ha, showed 100%, 90% and 95% herbicidal activity against *Amaranthus retroflexus, Echinocloa crus-galli* and *Setaria faber* respectively.

Example 241 applied by pre-emergence method at an application rate of 250 g/ha, showed 100%, 85% and 85% herbicidal activity against *Amaranthus retroflexus, Echinocloa crus-galli* and *Setaria faber* respectively.

Example 243 applied by pre-emergence method at an application rate of 250 g/ha, showed 85%, 85% and 85% herbicidal activity against *Abutilon theophrasti, Echinocloa crus-galli* and *Setaria faber* respectively. Example 244 applied by pre-emergence method at an application rate of 250 g/ha, showed 85%, 75% and 75% herbicidal activity against *Abutilon theophrasti, Amaranthus retroflexus* and *Setaria faberi* respectively.

Example 246 applied by pre-emergence method at an application rate of 250 g/ha, showed 100% herbicidal activity against *Abutilon theophrasti, Amaranthus retroflexus,* and *Echinocloa crus-galli*.

Example 247 applied by pre-emergence method at an application rate of 250 g/ha, showed 100% herbicidal activity against *Amaranthus retroflexus, Echinocloa crus-galli* and *Setaria* faber.

Example 248 applied by pre-emergence method at an application rate of 250 g/ha, showed 100% herbicidal activity against *Abutilon theophrasti, Amaranthus retroflexus,* and *Echinocloa crus-galli*.

Example 249 applied by pre-emergence method at an application rate of 250 g/ha, showed 100% herbicidal activity against *Abutilon theophrasti, Echinocloa crus-galli* and *Setaria faberi*.

Example 250 applied by pre-emergence method at an application rate of 250 g/ha, showed 100% herbicidal activity against *Abutilon theophrasti, Amaranthus retroflexus,* and *Echinocloa crus-galli*.

Example 251 applied by pre-emergence method at an application rate of 250 g/ha, showed 98%, 95% and 100% herbicidal activity against *Abutilon theophrasti, Echinocloa crus-galli* and *Setaria faber* respectively.

Example 252 applied by pre-emergence method at an application rate of 250 g/ha, showed 100%, 95% and 100% herbicidal activity against *Abutilon theophrasti, Amaranthus retroflexus* and *Setaria faber* respectively.

Example 254 applied by pre-emergence method at an application rate of 250 g/ha, showed 100% herbicidal activity against *Abutilon theophrasti, Echinocloa crus-galli* and *Setaria faberi*.

Example 255 applied by pre-emergence method at an application rate of 250 g/ha, showed 90%, 95% and 90% herbicidal activity against *Alopercurus myosuroides, Echinocloa crus-galli* and *Setaria faber* respectively.

Example 256 applied by pre-emergence method at an application rate of 250 g/ha, showed 100% herbicidal activity against *Amaranthus retroflexus, Echinocloa crus-galli* and *Setaria* faber.

Example 257 applied by pre-emergence method at an application rate of 250 g/ha, showed 100% herbicidal activity against *Abutilon theophrasti, Echinocloa crus-galli* and *Setaria faberi*.

Example 259 applied by pre-emergence method at an application rate of 250 g/ha, showed 100% herbicidal activity against *Amaranthus retroflexus* and *Setaria faberi*.

The invention claimed is:
1. A diaminotriazine compound of formula (I)

wherein
q is 0, 1, 2, or 3
Q is O,
wherein
$R^a$ is selected from the group consisting of halogen, CN, $C_1$-$C_4$-alkyl, and $C_1$-$C_4$-alkoxy, where the radicals are unsubstituted, partly or completely halogenated;
$R^b$ is selected from the group consisting of halogen, CN, $C_1$-$C_4$-alkyl, and $C_1$-$C_4$-alkoxy, where the aliphatic parts of the radicals are unsubstituted, partly or completely halogenated,
for q=2 or 3 it being possible that $R^b$ are identical or different;
$R^1$ is selected from the group consisting of H and $C_1$-$C_6$-alkyl;
$R^2$ is selected from the group consisting of H, halogen, OH, CN, $C_1$-$C_6$-alkyl, ($C_1$-$C_6$-alkoxy)-$C_1$-$C_6$-alkyl, $C_3$-$C_6$-cycloalkyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy, ($C_3$-$C_6$-cycloalkyl)-$C_1$-$C_4$-alkoxy, where the aliphatic and cycloaliphatic parts of the radicals are unsubstituted, partly or completely halogenated;
$R^3$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy;
$R^4$ is selected from the group consisting of halogen, CN, $C_1$-$C_6$-alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the radicals are unsubstituted, partly or completely halogenated;
$R^3$ and $R^4$ together with the carbon atom to which they are attached form a moiety selected from the group consisting of carbonyl, $C_3$-$C_6$-cycloalkyl, $C_3$-$C_6$-cycloalkenyl, three- to six-membered saturated or partially unsaturated heterocyclyl, and the moiety $>C=CR^xR^y$, where $R^x$ and $R^y$ are hydrogen, $C_1$-$C_4$-alkyl, $C_1$-$C_4$-haloalkyl, $C_3$-$C_6$-cycloalkyl or $CR^xR^y$ form a 3 to 6 membered cycloalkyl;
$R^5$ is selected from the group consisting of H and $C_1$-$C_6$-alkyl;
$R^6$ is phenyl, which is unsubstituted or carries 1, 2, 3, 4, or 5 radicals $R^{6A}$ which are selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the radicals are unsubstituted, partly or completely halogenated and where the cycloaliphatic parts of the radicals may carry 1, 2, 3, 4, 5, or 6 methyl groups,
it being possible that $R^{6A}$ are identical or different;
$R^7$ and $R^{7'}$ are independently selected from the group consisting of hydrogen, halogen, $C_1$-$C_4$-alkyl, $C_2$-$C_6$-alkenyl, $C_2$-$C_6$-alkynyl, $C_1$-$C_6$-alkoxy, $C_1$-$C_6$-halogenoalkoxy, and $C_3$-$C_6$-cycloalkyl;
including their agriculturally acceptable salts.

2. The compound of claim 1, wherein $R^a$ is fluorine or chlorine.

3. The compound of claim 1, wherein $R^b$ is fluorine, chlorine, bromine, or methyl.

4. The compound of claim 1, wherein $R^t$ is.

5. The compound of claim 1, wherein
$R^2$ is selected from the group consisting of hydrogen, fluorine, $C_1$-$C_4$-alkyl and $C_1$-$C_4$-alkoxy;
$R^3$ is selected from the group consisting of hydrogen, fluorine, $C_1$-$C_4$-alkyl, $C_1$-$C_4$-haloalkyl, $C_1$-$C_4$-alkoxy and $C_1$-$C_6$-haloalkoxy;
$R^4$ is selected from the group consisting of $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, and $C_1$-$C_6$-alkoxy-$C_1$-$C_6$-alkyl; or
$R^3$ and $R^4$ together with the carbon atom to which they are attached form a moiety selected from the group consisting of $C_3$-$C_6$-cycloalkyl, $C_3$-$C_6$-cycloalkenyl and three- to six-membered saturated or partially unsaturated heterocyclyl.

6. The compound of claim 1, wherein $R^5$ is.

7. The compound of claim 1, wherein $R^{6A}$, if present, is selected from the group consisting of halogen, CN, $C_1$-$C_4$-alkyl, $C_1$-$C_4$-haloalkyl, $C_1$-$C_4$-alkoxy, $C_1$-$C_4$-haloalkoxy and $C_3$-$C_6$-cycloalkyl.

8. An agrochemical composition comprising a herbicidal active amount of at least one compound as claimed in claim 1 and at least one inert liquid and/or solid carrier and, optionally, at least one surface-active substance.

9. A method of controlling unwanted vegetation comprising applying a compound as claimed in claim 1 to a plant for desiccation/defoliation of the plant.

* * * * *

UNITED STATES PATENT AND TRADEMARK OFFICE
CERTIFICATE OF CORRECTION

| | | |
|---|---|---|
| PATENT NO. | : 11,992,012 B2 | Page 1 of 1 |
| APPLICATION NO. | : 17/270884 | |
| DATED | : May 28, 2024 | |
| INVENTOR(S) | : Danny Geerdink et al. | |

It is certified that error appears in the above-identified patent and that said Letters Patent is hereby corrected as shown below:

In the Claims

At Column 138, Line 21, "Rt is." should be -- R1 is H. --.

At Column 138, Line 27, "R5 is." should be -- R5 is H. --.

Signed and Sealed this
Tenth Day of December, 2024

Katherine Kelly Vidal
*Director of the United States Patent and Trademark Office*